(12) United States Patent
Beshore et al.

(10) Patent No.: US 9,139,576 B2
(45) Date of Patent: Sep. 22, 2015

(54) AMINOMETHYL BIARYL BENZOTRIAZOLE DERIVATIVES

(75) Inventors: Douglas C. Beshore, Lower Gwynedd, PA (US); Robert M. Garbaccio, Lansdale, PA (US); Scott D. Kuduk, Harleysville, PA (US); Adam W. Johnson, Philadelphia, PA (US); Jason W. Skudlarek, Audubon, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/115,123

(22) PCT Filed: Apr. 30, 2012

(86) PCT No.: PCT/US2012/035724
§ 371 (c)(1),
(2), (4) Date: Nov. 1, 2013

(87) PCT Pub. No.: WO2012/151136
PCT Pub. Date: Nov. 8, 2012

(65) Prior Publication Data
US 2014/0066443 A1    Mar. 6, 2014

Related U.S. Application Data

(60) Provisional application No. 61/481,821, filed on May 3, 2011.

(51) Int. Cl.
| C07D 413/12 | (2006.01) |
| C07D 401/14 | (2006.01) |
| C07D 403/10 | (2006.01) |
| C07D 249/18 | (2006.01) |
| C07D 401/10 | (2006.01) |
| C07D 401/12 | (2006.01) |
| C07D 413/10 | (2006.01) |

(52) U.S. Cl.
CPC ............ *C07D 413/12* (2013.01); *C07D 249/18* (2013.01); *C07D 401/10* (2013.01); *C07D 401/12* (2013.01); *C07D 401/14* (2013.01); *C07D 403/10* (2013.01); *C07D 413/10* (2013.01)

(58) Field of Classification Search
None
See application file for complete search history.

(56) References Cited

U.S. PATENT DOCUMENTS

| 5,444,038 | A  | 8/1995  | James et al. |
| 7,456,200 | B2 | 11/2008 | Arora et al. |
| 7,546,200 | B2 | 6/2009  | Justice |
| 7,960,417 | B2 | 6/2011  | Govek et al. |
| 8,765,784 | B2 | 7/2014  | Arrington et al. |
| 8,772,276 | B2 | 7/2014  | Kuduk et al. |
| 8,785,481 | B2 | 7/2014  | Beshore et al. |
| 8,952,005 | B2 | 2/2015  | Layton et al. |
| 2004/0127536 | A1 | 7/2004 | Bhagwat et al. |
| 2006/0122240 | A1 | 6/2006 | Semple et al. |
| 2006/0122397 | A1 | 6/2006 | Arora et al. |
| 2007/0265309 | A1 | 11/2007 | Eastwood et al. |
| 2008/0176904 | A1 | 7/2008 | Govek et al. |
| 2010/0137288 | A1 | 6/2010 | Schumacher et al. |
| 2011/0059947 | A1 | 3/2011 | Bencherif et al. |
| 2012/0135977 | A1 | 5/2012 | Beshore et al. |
| 2012/0149677 | A1 | 6/2012 | Dudkin et al. |
| 2013/0143880 | A1 | 6/2013 | Dudkin et al. |
| 2013/0158002 | A1 | 6/2013 | Layton et al. |
| 2013/0210768 | A1 | 8/2013 | Arrington et al. |
| 2014/0045829 | A1 | 2/2014 | Layton et al. |
| 2014/0088112 | A1 | 3/2014 | Kuduk et al. |
| 2014/0088150 | A1 | 3/2014 | Beshore et al. |
| 2014/0088151 | A1 | 3/2014 | Beshore et al. |
| 2014/0350002 | A1 | 11/2014 | Fiji et al. |

FOREIGN PATENT DOCUMENTS

| WO | WO 2010/010157 | * | 1/2010 |
| WO | WO2012151138 A1 | | 11/2012 |
| WO | WO2012151139 A1 | | 11/2012 |
| WO | WO2012151140 A1 | | 11/2012 |

OTHER PUBLICATIONS

NPL—International Search Report for PCT/US2012/035724.

* cited by examiner

*Primary Examiner* — Anna Pagonakis
(74) *Attorney, Agent, or Firm* — Keith D. MacMillan; John C. Todaro

(57) ABSTRACT

The present invention is directed to aminomethyl biaryl benzotriazole derivatives which are potentiators of metabotropic glutamate receptors, particularly the mGluR2 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

16 Claims, No Drawings

AMINOMETHYL BIARYL BENZOTRIAZOLE DERIVATIVES

BACKGROUND OF THE INVENTION

The excitatory amino acid L-glutamate (sometimes referred to herein simply as glutamate) through its many receptors mediates most of the excitatory neurotransmission within the mammalian central nervous system (CNS). The excitatory amino acids, including glutamate, are of great physiological importance, playing a role in a variety of physiological processes, such as long-term potentiation (learning and memory), the development of synaptic plasticity, motor control, respiration, cardiovascular regulation, and sensory perception.

Glutamate acts via at least two distinct classes of receptors. One class is composed of the ionotropic glutamate (iGlu) receptors that act as ligand-gated ionic channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGluR) receptor. Both types of receptors appear not only to mediate normal synaptic transmission along excitatory pathways, but also participate in the modification of synaptic connections during development and throughout life. Schoepp, Bockaert, and Sladeczek, Trends in Pharmacol. Sci., 11, 508 (1990); McDonald and Johnson, Brain Research Reviews, 15, 41 (1990).

The present invention relates to potentiators of mGlu receptors, in particular mGluR2 receptors. The mGluR receptors belong to the Type III G-protein coupled receptor (GPCR) superfamily. This superfamily of GPCR's including the calcium-sensing receptors, GABAB receptors and pheromone receptors, which are unique in that they are activated by binding of effectors to the amino-terminus portion of the receptor protein. The mGlu receptors are thought to mediate glutamate's demonstrated ability to modulate intracellular signal transduction pathways. Ozawa, Kamiya and Tsuzuski, Prog. Neurobio., 54, 581 (1998). They have been demonstrated to be localized both pre- and post-synaptically where they can regulate neurotransmitter release, either glutamate or other neurotransmitters, or modify the post-synaptic response of neurotransmitters, respectively.

At present, there are eight distinct mGlu receptors that have been positively identified, cloned, and their sequences reported. These are further subdivided based on their amino acid sequence homology, their ability to affect certain signal transduction mechanisms, and their known pharmacological properties. Ozawa, Kamiya and Tsuzuski, Prog. Neurobio., 54, 581 (1998). For instance, the Group I mGluR receptors, which include the mGluR1 and mGluR5, are known to activate phospholipase C (PLC) via G$\alpha$q-proteins thereby resulting in the increased hydrolysis of phosphoinositides and intracellular calcium mobilization. There are several compounds that are reported to activate the Group I mGlu receptors including DHPG, (R/S)-3,5-dihydroxyphenylglycine. Schoepp, Goldworthy, Johnson, Salhoff and Baker, J. Neurochem., 63, 769 (1994); Ito, et al., keurorep., 3, 1013 (1992). The Group II mGlu receptors consist of the two distinct receptors, mGluR2 and mGluR3 receptors. Both have been found to be negatively coupled to adenylate cyclase via activation of G$\alpha$i-protein. These receptors can be activated by a selective compound such as 1S,2S,SR,6S-2 aminobicyclo [3.1.0]hexane-2,6-dicarboxylate. Monn, et al., J. Med. Chem., 40, 528 (1997); Schoepp, et al., Neuropharmacol., 36, 1 (1997). This activation leads to inhibition of glutamate release in the synapse (Cartmell et al, J Neurochem 75, 889 (2000)). Similarly, the Group III mGlu receptors, including mGluR4, mGluR6, mGluR7 and mGluR8, are negatively coupled to adenylate cyclase via G$\alpha$i and are potently activated by L-AP4 (L-(+)-2-amino-4-phosphonobutyric acid). Schoepp, Neurochem. Int., 24, 439 (1994).

Nonselective mGluR2/mGluR3 receptor agonists (Monn, et al., J. Med. Chem., 43, 4893, (2000)) have shown efficacy in numerous animal models of anxiety and psychosis as well as human clinical trials in schizophrenia patients; Patil et al, Nature Medicine, 13, 1102 (2007). Recent reports indicate that mGluR2 but not the mGluR3 receptor mediates the actions of the dual mGluR2/mGluR3 agonist LY379268 in mouse models predictive of antipsychotic activity. Woolley et al, Psycopharmacology, 196, 431 (2008). Additionally, recent animal studies demonstrate that selective potentiation of the mGluR2 receptor has similar effects to such nonselective agonists (Galici et al, Journal of Pharmacology and Experimental Therapeutics, 315, 1181 (2005)) suggesting an alternative strategy concerning the discovery of selective, positive allosteric modulators (PAMs or allosteric potentiators) of mGluR2 (Johnson et al, J. Med. Chem. 46, 3189, (2003); Pinkerton et al., J. Med. Chem., 47, 4595 (2004). These potentiators act by enabling the receptor to produce an enhanced response to endogenous glutamate. Such allosteric potentiators do not bind at the glutamate binding site also known as the "orthosteric site", and may benefit by binding to a site other than the highly conserved orthosteric site. A potential advantage to this approach includes the opportunity to have a distinct pharmacological profile by enhancing the activity of the endogenous ligand upon its binding to the orthosteric site. The pharmacological distinctions include the potential for pharmacological specificity between related receptor types that share the same endogenous ligand. In addition, positive allosteric modulators of mGluR2 have been shown to potentiate the response of mGluR2 agonists such as LY379268 (Johnson et. Al. Biochemical Soc. Trans. 32, 881 (2004) and this represents an alternative strategy for treatment using mGluR2 selective PAMs.

It has become increasingly clear that there is a link between modulation of excitatory amino acid receptors, including the glutamatergic system, through changes in glutamate release or alteration in postsynaptic receptor activation, and a variety of neurological and psychiatric disorders. e.g. Monaghan, Bridges and Cotman, Ann. Rev. Pharmacol. Toxicol., 29, 365-402 (1989); Schoepp and Sacann, Neurobio. Aging, 15, 261-263 (1994); Meldrum and Garthwaite, Tr. Pharmacol. Sci., 11, 379-387 (1990). The medical consequences of such glutamate dysfunction make the abatement of these neurological processes an important therapeutic goal.

SUMMARY OF THE INVENTION

The present invention is directed to aminomethyl biaryl benzotriazole derivatives which are potentiators of metabotropic glutamate receptors, particularly the mGluR2 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

DETAILED DESCRIPTION OF THE INVENTION

The invention encompasses a genus of compounds of Formula I or Formula II

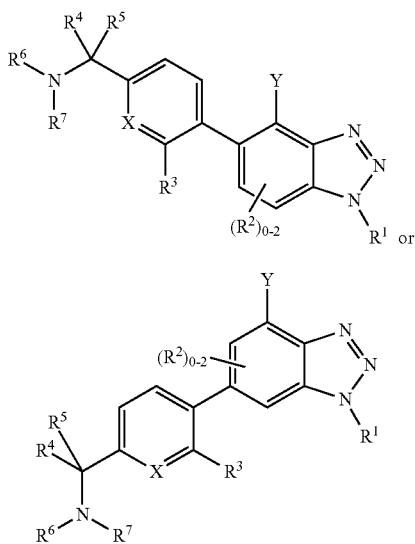

or a pharmaceutically acceptable salt thereof, wherein:

$R^1$ is selected from the group consisting of:
(1) $C_{2-8}$alkyl,
(2) $C_{2-8}$alkenyl,
(3) $C_{2-8}$alkynyl,
(4) $C_{3-6}$cycloalkyl-$(CH_2)_p$—, wherein p is 1, 2, 3 or 4, and
(5) benzyl, wherein groups (1) to (5) above are optionally substituted with 1 to 3 $R^a$ groups;

each $R^a$ and $R^2$ is independently selected from the group consisting of: halo, OH, $C_{1-4}$alkyl, $C_{1-4}$alkoxy, $CF_3$, —$OCF_3$ and —CN;

Y is selected from the group consisting of: H, halo, CN, $C_{1-4}$alkyl, $C_{2-4}$alkenyl and $CH_3$—$S(O)_q$—, wherein said $C_{1-4}$alkyl and $C_{2-4}$alkenyl are optionally substituted with hydroxy, oxo and one or more fluoro groups as allowed by valence;

X is $C(R^8)$ or N, or the N-oxide thereof;
$R^3$ is selected from H or halogen;
$R^4$ and $R^5$ are independently selected from H and $C_{1-4}$alkyl, optionally substituted with hydroxy, or $R^4$ and $R^5$ may be joined together to form carbonyl;
$R^6$ is selected from the group consisting of H, —C(O)—$R^9$ and —$S(O)_r$—$R^9$, and
$R^7$ is H or $C_{1-4}$alkyl,
or $R^6$ and $R^7$ and the nitrogen atom to which they are attached may be joined together to form a 5- or 6-membered non-aromatic ring optionally containing one or two additional heteroatoms selected from N, S or O, said ring optionally substituted with one or two oxo groups and one to three substituents independently selected from halo, CN, $R^9$, —O—$R^9$, —C(O)—$R^9$—C(O)—O—$R^9$ and —$S(O)_r$—$R^9$,
or $R^6$ and $R^7$ and the nitrogen atom to which they are attached may be joined together to form azide;
$R^8$ is selected from H and $C_{1-4}$alkyl;
each $R^9$ independently represents: (1) H, $C_{1-6}$alkyl, $C_{2-6}$alkenyl, $C_{2-6}$alkynyl, $C_{3-10}$cycloalkyl, $C_{3-10}$cycloalkyl$C_{1-4}$alkyl, $C_{3-10}$cycloalkenyl or $C_{3-10}$cycloalkenyl$C_{1-4}$alkyl, any of which except H optionally bear OH, CN, $CF_3$ and $C_{1-4}$alkoxy and up to 5 halogen atoms; (2) phenyl, benzyl or heteroaryl, optionally bridged with a methylene, any of which optionally bear up to 3 substituents independently selected from halogen, OH, oxo, CN, $CF_3$, $C_{1-4}$alkyl, $C_{1-4}$hydroxyalkyl, $C_{3-6}$cycloalkyl, phenyl, heteroaryl, $C_{1-4}$alkoxy, acetyl, amino, carbamoyl, $CO_2$—$C_{1-4}$alkyl, $C_{1-4}$alkylamino and di($C_{1-4}$alkyl)amino; and (3) Het, optionally bridged with a methylene and said Het optionally bearing up to 3 substituents independently selected from halogen, OH, oxo, CN, $CF_3$, $C_{1-4}$alkyl, $C_{1-4}$hydroxyalkyl, $C_{3-6}$cycloalkyl, phenyl, heteroaryl, $C_{1-4}$alkoxy, acetyl, amino, carbamoyl, $CO_2$—$C_{1-4}$alkyl, $C_{1-4}$alkylamino and di($C_{1-4}$alkyl)amino;

each "heteroaryl" independently refers to 5- or 6-membered aromatic monocyclic or 9- or 10-membered aromatic bicyclic ring systems, in which at least one ring atom is selected from N or N-oxide, O and S;

each "Het" independently refers to nonaromatic or partially aromatic mono- or bicyclic heterocyclic systems of up to 10 ring atoms, in which at least one ring atom is selected from N, O and S, where the sulfur atom may be in the form of the S-oxide or S,S-dioxide; and q, r and t are independently 0, 1 or 2.

Within the genus, the invention encompasses a first sub-genus of compounds of Formula I or Formula II, or a pharmaceutically acceptable salt thereof, wherein $R^1$ is cyclopropylmethyl, 2-methylpropyl or 2,2-dimethylpropyl.

Also within the genus, the invention encompasses a second sub-genus of compounds of Formula I or Formula II, or a pharmaceutically acceptable salt thereof, wherein $R^2$ is not present.

Also within the genus, the invention encompasses a third sub-genus of compounds of Formula I or Formula II, or a pharmaceutically acceptable salt thereof, wherein Y is hydrogen, chloro, bromo, methylsulfanyl, methylsulfinyl, methylsulfonyl, cyano, methyl, ethyl, propyl, isopropyl, prop-2-en-1-yl, formyl, hydroxymethyl, fluoromethyl, difluoromethyl and trifluoromethyl.

Also within the genus, the invention encompasses a fourth sub-genus of compounds of Formula I or Formula II, or a pharmaceutically acceptable salt thereof, wherein X is N. Within the fourth sub-genus, the invention encompasses a first class of compounds of Formula I or Formula II, or a pharmaceutically acceptable salt thereof, wherein $R^3$ is F.

Also within the genus, the invention encompasses a fifth sub-genus of compounds of Formula I or Formula II, or a pharmaceutically acceptable salt thereof, wherein X is $C(R^8)$, $R^3$ is H or F, and $R^8$ is H.

Also within the genus, the invention encompasses a sixth sub-genus of compounds of Formula I or Formula II, or a pharmaceutically acceptable salt thereof, wherein $R^6$ is selected from the group consisting of H, —C(O)—$R^9$ and —$S(O)_r$—$R^9$, and $R^7$ is H.

Also within the genus, the invention encompasses a seventh sub-genus of compounds of Formula I or Formula II, or a pharmaceutically acceptable salt thereof, wherein $R^6$ and $R^7$ and the nitrogen atom to which they are attached are joined together to form a 5- or 6-membered non-aromatic ring optionally containing one or two additional heteroatoms selected from N, S or O, said ring optionally substituted with one or two oxo groups and one to three substituents independently selected from halo, CN, $R^9$, —O—$R^9$, —C(O)—$R^9$, —C(O)—O—$R^9$ and —$S(O)_r$—$R^9$. Within the seventh sub-genus, the invention encompasses a second class of compounds of Formula I or Formula II, or a pharmaceutically acceptable salt thereof, wherein $R^6$ and $R^7$ and the nitrogen atom to which they are attached are joined together to form 3-methylimidazolidine-2,4-dione. Also within the seventh sub-genus, the invention encompasses a third class of compounds of Formula I or Formula II, or a pharmaceutically acceptable salt thereof, wherein $R^6$ and $R^7$ and the nitrogen atom to which they are attached are joined together to form pyrrolidine, piperidine, piperazine or morpholine, each of which is optionally substituted with one to three substituents independently selected from halo, CN, $R^9$, —O—$R^9$, —C(O)—$R^9$, —C(O)—O—$R^9$ and —S(O)$_r$—$R^9$.

Also within the genus, the invention encompasses an eighth sub-genus of compounds of Formula I or Formula II, or a pharmaceutically acceptable salt thereof, wherein $R^4$ and $R^5$ are H.

Also within the genus, the invention encompasses a ninth sub-genus of compounds having Formula I wherein:

$R^1$ is cyclopropylmethyl, 2-methylpropyl or 2,2-dimethylpropyl;

$R^2$ is not present;

Y is hydrogen, chloro, bromo, methylsulfanyl, methylsulfinyl, methylsulfonyl, cyano, methyl, ethyl, propyl, isopropyl, prop-2-en-1-yl, formyl, hydroxymethyl, fluoromethyl, difluoromethyl and trifluoromethyl;

$R^3$ is H or F;

$R^4$ and $R^5$ are H;

$R^6$ and $R^7$ and the nitrogen atom to which they are attached are joined together to form 3-methylimidazolidine-2,4-dione, or $R^6$ and $R^7$ and the nitrogen atom to which they are attached are joined together to form pyrrolidine, piperidine, piperazine or morpholine, each of which is optionally substituted with one to three substituents independently selected from halo, CN, $R^9$, —O—$R^9$, —C(O)—$R^9$, —C(O)—O—$R^9$ and —S(O)$_r$—$R^9$;

$R^8$ is H;

each $R^9$ independently represents: (1) $C_{1-4}$alkyl, cyclopropyl and cyclopropylmethyl, any of which optionally bear OH, CN and up to 5 halogen atoms, and (2) triazolyl, imidazolyl, isoxazolyl or pyridyl, each optionally bridged with a methylene, and each optionally substituted with methyl.

Also within the genus, the invention encompasses a tenth sub-genus of compounds having Formula I wherein:

$R^1$ is cyclopropylmethyl, 2-methylpropyl or 2,2-dimethylpropyl;

$R^2$ is not present;

Y is hydrogen, chloro, bromo, methylsulfanyl, methylsulfinyl, methylsulfonyl, cyano, methyl, ethyl, propyl, isopropyl, prop-2-en-1-yl, formyl, hydroxymethyl, fluoromethyl, difluoromethyl and trifluoromethyl;

$R^3$ is H or F;

$R^4$ and $R^5$ are H;

$R^6$ is selected from the group consisting of H, —C(O)—$R^9$ and —S(O)$_r$—$R^9$;

$R^7$ and $R^8$ are H;

each $R^9$ independently represents: (1) $C_{1-4}$alkyl, cyclopropyl and cyclopropylmethyl, any of which optionally bear OH, CN and up to 5 halogen atoms, and (2) triazolyl, imidazolyl, isoxazolyl or pyridyl, each optionally bridged with a methylene, and each optionally substituted with methyl.

The invention also encompasses the compounds that follow.

The invention also encompasses a pharmaceutical composition comprising a compound of the invention in combination with a pharmaceutically acceptable carrier.

The invention also encompasses a method for treating a neurological or psychiatric disorder associated with glutamate dysfunction in a patient in need thereof comprising administering to the patient a therapeutically effective amount of a compound of the invention. The invention also encompasses this method wherein the neurological or psychiatric disorder associated with glutamate dysfunction is schizophrenia.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono-, bi- or tri-cyclic structures, optionally combined with linear or branched structures, having the indicated number of carbon atoms. Examples of cycloalkyl groups include cyclopropyl, cyclopentyl, cycloheptyl, adamantyl, cyclododecylmethyl, 2-ethyl-1-bicyclo [4.4.0]decyl, and the like.

"Alkoxy" means alkoxy groups of a straight or branched having the indicated number of carbon atoms. $C_{1-6}$alkoxy, for example, includes methoxy, ethoxy, propoxy, isopropoxy, and the like.

"Halogen" and "halo" includes fluorine, chlorine, bromine and iodine.

The compounds of the present invention are potentiators of metabotropic glutamate (mGluR) receptor function, in particular they are potentiators of mGluR2 receptors. That is, the compounds of the present invention do not appear to bind at the glutamate recognition site on the mGluR receptor, but in the presence of glutamate or a glutamate agonist, the compounds of the present invention increase mGluR receptor response. The present potentiators are expected to have their effect at mGluR receptors by virtue of their ability to increase the response of such receptors to glutamate or glutamate agonists, enhancing the function of the receptors. It is recognized that the compounds of the present invention would be expected to increase the effectiveness of glutamate and glutamate agonists of the mGluR2 receptor. Thus, the potentiators of the present invention are expected to be useful in the treatment of various neurological and psychiatric disorders associated with glutamate dysfunction described to be treated herein and others that can be treated by such potentiators as are appreciated by those skilled in the art.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in substantially pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of generic Formula I or Formula II, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I or Formula II. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I or Formula II can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. A subgroup is the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. A subgroup is citric, hydrobromic, hydrochloric, maleic, phosphoric, sulfuric, fumaric, and tartaric acids. It will be understood that, as used herein, references to the compounds of Formula I or Formula II are meant to also include a pharmaceutically acceptable salts.

Exemplifying the invention are Examples 1 to 85, described herein. The subject compounds are useful in a method of potentiating metabotropic glutamate receptor activity in a patient such as a mammal in need of such inhibition comprising the administration of an effective amount of the compound. The present invention is directed to the use of the subject compounds disclosed herein as potentiators of metabotropic glutamate receptor activity. In addition to primates, especially humans, a variety of other mammals can be treated according to the method of the present invention.

The present invention is further directed to a method for the manufacture of a medicament for potentiating metabotropic glutamate receptor activity in humans and animals comprising combining a compound of the present invention with a pharmaceutical carrier or diluent.

The subject treated in the present methods is generally a mammal, preferably a human being, male or female, in whom potentiation of metabotropic glutamate receptor activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as potentiators or agonists of metabotropic glutamate receptor activity, in particular mGluR2 activity, may be demonstrated by methodology known in the art. Potencies are determined as follows. The compounds of the present invention may be tested in a fluorescence laser imaging plate reader (FLIPR) based assay. This assay is a common functional assay to monitor $Ca^{2+}$ mobilization in whole cells expressing recombinant receptor coupled with a promiscuous G-protein. CHO dhfr-cells stably expressing recombinant human mGluR2 and Gα16 loaded with Fluo-4 AM (Invitrogen, Carlsbad Calif.) are treated with varying concentrations of compounds and the $Ca^{2+}$ response is monitored on a FLIPR384 (Molecular Devices, Sunnydale Calif.) for agonist activity. The potentiation response is monitored after a subsequent addition of an $EC_{20}$ concentration of glutamate (900 nM). The maximum calcium response at each concentration of compound for agonism or potentiation are plotted as dose responses curves fitted with a four parameters logistic equation giving $EC_{50}$ and Hill coefficient using the iterative non linear curve fitting software program.

The compounds of the present invention may also be tested in a [$^{35}$S]-GTPγS assay. [$^{35}$S]-GTPγS binding is a common functional assay to monitor Gαi-coupled receptor in native and recombinant receptor membrane preparation. Membranes from $CHO_{dhfr}$ cells stably expressing recombinant hmGluR2 and Gα16 (25 μg) or HEK293 cells stably expressing recombinant rat mGluR2 (25 μg) are incubated in a 96 well plate for 1 hour in the presence of [$^{35}$S]-GTPγS (0.05 nM), GDP (5 μM), and varying concentrations of compounds, with (for potentiation) or without (for agonism) a sub-threshold ($EC_{10}$) concentration of glutamate (1500 nM for hmGluR2 or 750 nM for rat mGluR2). The reaction is stopped by rapid filtration over Unifilter GF/B plate (Packard, Bioscience, Meriden Conn.) using a 96-well cell harvester (Brandel Gaithersburg, Md.). After the addition of Microscint 20 (Packard, Bioscience, Meriden Conn.), the filter plates are counted using a Topcount counter (Packard, Bioscience, Meriden Conn., USA). The agonist or the potentiator curves are fitted with a four parameters logistic equation giving $EC_{50}$ and Hill coefficient using an iterative non linear curve fitting software program.

In particular, Examples 1 to 85 were tested and demonstrated activity in potentiating the mGluR2 receptor in the FLIPR assay, generally with an $EC_{50}$ of less than about 10 μM. Compounds within the present invention had activity in potentiating the mGluR2 receptor in the FLIPR and GTPγS assays with an $EC_{50}$ of less than about 1 μM. Examples Examples 1 to 85 resulted in a minimum 1.8-fold potentiation of glutamate response in the presence of an $EC_{20}$ concentration of glutamate (900 nM). Such results are indicative of the intrinsic activity of the compounds in use as potentiators of mGluR2 receptor activity.

Representative FLIPR $EC_{50}$ Values

| Ex. | $EC_{50}$ (nM) | N |
| --- | --- | --- |
| 1 | 17.3 | 2 |
| 2 | 5.8 | 3 |
| 4 | 9.21 | 2 |
| 5 | 59.1 | 2 |
| 7 | 532 | 1 |
| 8 | 3.0 | 2 |
| 9 | 6.1 | 3 |
| 10 | 5.3 | 6 |

-continued

| Ex. | $EC_{50}$ (nM) | N |
| --- | --- | --- |
| 15 | 6.6 | 2 |
| 16 | 245 | 1 |
| 17 | 1254 | 1 |
| 18 | 39 | 2 |
| 19 | 7.8 | 2 |
| 20 | 56 | 2 |
| 21 | 841 | 1 |
| 22 | 14 | 2 |
| 28 | 196 | 1 |
| 29 | 11.4 | 5 |
| 37 | 53 | 2 |
| 38 | 2316 | 1 |
| 39 | 49 | 2 |
| 51 | 11.4 | 5 |
| 52 | 80 | 1 |
| 71 | 234 | 1 |
| 72 | 30.4 | 2 |
| 83 | 124 | 1 |
| 84 | 34.9 | 2 |
| 85 | 8.9 | 2 |

Metabotropic glutamate receptors including the mGluR2 receptor have been implicated in a wide range of biological functions. This has suggested a potential role for these receptors in a variety of disease processes in humans or other species.

The compounds of the present invention have utility in treating, preventing, ameliorating, controlling or reducing the risk of a variety of neurological and psychiatric disorders associated with glutamate dysfunction, including one or more of the following conditions or diseases: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), autism, autism spectrum disorders, attention deficit/hyperactivity disorder, and conduct disorder.

Of the disorders above, the treatment of migraine, anxiety, schizophrenia, and epilepsy are of particular interest. In an embodiment the present invention provides a method for treating migraine, comprising: administering to a patient in need thereof an effective amount of a compound of Formula I or Formula II. In another embodiment the present invention provides a method for preventing or treating anxiety, comprising: administering to a patient in need thereof an effective amount of a compound of Formula I or Formula II. Particularly anxiety disorders are generalized anxiety disorder, panic disorder, and obsessive compulsive disorder. In another embodiment the present invention provides a method for treating schizophrenia, comprising: administering to a patient in need thereof an effective amount of a compound of Formula I or Formula II. In yet another embodiment the present invention provides a method for treating epilepsy, comprising: administering to a patient in need thereof an effective amount of a compound of Formula I or Formula II.

Of the neurological and psychiatric disorders associated with glutamate dysfunction which are treated according to the present invention, the treatment of migraine, anxiety, schizophrenia, and epilepsy encompass a subgroup of the invention. Particular anxiety disorders are generalized anxiety disorder, panic disorder, and obsessive compulsive disorder.

In an embodiment, the present invention provides a method for the treatment of schizophrenia comprising: administering to a patient in need thereof an effective amount of a compound of Formula I or Formula II or a pharmaceutical composition thereof. In one of the available sources of diagnostic tools, The Merck Manual (2006-2007), schizophrenia is characterized by psychosis (loss of contact with reality), hallucinations (false perceptions), delusions (false beliefs), disorganized speech and behavior, flattened affect (restricted range of emotions), cognitive deficits (impaired reasoning and problem solving), and occupational and social dysfunction. The skilled artisan will recognize that there are alternative nomenclatures, nosologies, and classification systems for neurological and psychiatric disorders, including schizophrenia, and that these systems evolve with medical scientific progress.

Thus, in an embodiment the present invention provides a method for treating migraine, comprising: administering to a patient in need thereof an effective amount of a compound of Formula I or Formula II or a pharmaceutical composition thereof. In one of the available sources of diagnostic tools, Dorland's Medical Dictionary (23'd Ed., 1982, W. B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine" includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another embodiment the present invention provides a method for treating anxiety, comprising: administering to a patient in need thereof an effective amount of a compound of Formula I or Formula II or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another embodiment the present invention provides a method for treating depression, comprising: administering to a patient in need thereof an effective amount of a compound of Formula I or Formula II or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-IV.

In another embodiment the present invention provides a method for treating epilepsy, comprising: administering to a patient in need thereof an effective amount of a compound of Formula I or Formula II or a pharmaceutical composition thereof. At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley. (Lippincott-Raven, Philadelphia, 1997). At present, the International Classification of Diseases, Ninth Revision, (ICD-9) provides a diagnostic tool including epilepsy and related disorders. These include: generalized nonconvulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents, including an mGluR agonist.

The term "potentiated amount" refers to an amount of an mGluR agonist, that is, the dosage of agonist which is effective in treating the neurological and psychiatric disorders described herein when administered in combination with an effective amount of a compound of the present invention. A potentiated amount is expected to be less than the amount that is required to provided the same effect when the mGluR agonist is administered without an effective amount of a compound of the present invention.

A potentiated amount can be readily determined by the attending diagnostician, as one skilled in the art, by the use of conventional techniques and by observing results obtained under analogous circumstances. In determining a potentiated amount, the dose of an mGluR agonist to be administered in combination with a compound of Formula I or Formula II, a number of factors are considered by the attending diagnostician, including, but not limited to: the mGluR agonist selected to be administered, including its potency and selectivity; the compound of Formula I or Formula II to be coadministered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGluR agonist to be administered in combination with an effective amount of a compound of Formula I or Formula II is expected to vary from about 0.1 milligram per kilogram of body weight per day (mg/kg/day) to about 100 mg/kg/day and is expected to be less than the amount that is required to provided the same effect when administered without an effective amount of a compound of Formula I or Formula II. Preferred amounts of a co-administered mGlu agonist are able to be determined by one skilled in the art.

The compounds of the present invention may be used in combination with one or more other drugs in the treatment, prevention, control, amelioration, or reduction of risk of diseases or conditions for which compounds of Formula I or Formula II or the other drugs may have utility, where the combination of the drugs together are safer or more effective than either drug alone. Such other drug(s) may be administered, by a route and in an amount commonly used therefor, contemporaneously or sequentially with a compound of Formula I or Formula II. When a compound of Formula I or Formula II is used contemporaneously with one or more other drugs, a pharmaceutical composition in unit dosage form containing such other drugs and the compound of Formula I or Formula II is encompassed as an embodiment of the invention. However, the combination therapy may also includes therapies in which the compound of Formula I or Formula II and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I or Formula II.

The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is encompassed as part of the invention. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleageneous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require potentiation of metabotorpic glutamate receptor activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

When treating, preventing, controlling, ameliorating, or reducing the risk of neurological and psychiatric disorders associated with glutamate dysfunction or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Abbreviations used in the description of the chemistry and in the Examples that follow are: $Ac_2O$ (acetic anhydride); AcOH (acetic acid); AEBSF (p-aminoethylbenzenesulfonyl fluoride); Boc (tert-butyl carbamate); $(Boc)_2O$ (di-tert-butyl dicarbonate); BSA (bovine serum albumin); BuLi (n-butyl lithium); $CDCl_3$ (chloroform-d); CuI (copper iodide); $CuSO_4$ (copper sulfate); DBU (1,8-diazabicyclo[5.4.0]undec-7-ene); DCE (dichloroethane); DCM (dichloromethane); DEAD (diethyl azodicarboxylate); DIPEA or DIEA (diisopropylethylamine); DMBA (1,3-dimethylbarbituric acid); DMF (N,N-dimethylformamide); DMP (Dess-Martin periodinane); DMSO (dimethyl sulfoxide); DPPA (diphenylphosphoryl azide); DTT (dithiothreitol); EDTA (ethylene-diamine-tetra-acetic acid); EGTA (ethylene-glycol-tetra-acetic acid); $Et_2O$ (diethylether); EtOAc (ethyl acetate); EtOH (ethanol); HOAc (acetic acid); HPLC (high-performance liquid chromatography); HRMS (high resolution mass spectrum); LAH (lithium aluminum hydride); LCMS (liquid chromatograph-mass spectrometer); LHMDS (lithium bis(trimethylsilyl)amide); LRMS (low resolution mass spectrum); mCPBA (3-chloroperoxybenzoic acid); MeOH (methanol); MP-B(CN)$H_3$ (Macroporous cyanoborohydride); $NaHCO_3$ (sodium bicarbonate); $Na_2SO_4$ (sodium sulfate); $Na(OAc)_3BH$ (sodium triacetoxyborohydride); $NH_4OAc$ (ammonium acetate); NBS (N-bromosuccinamide); NFSi (N-fluorobenzenesulfonimide); NMP (1-methyl-2-pyrrolidinone); NMR (nuclear magnetic resonance); PBS (phosphate buffered saline); PCR (polymerase chain reaction); Pd(dppf) ([1,1'-bis(diphenylphosphino)ferrocene] palladium); $Pd(Ph_3)_4$ (palladium(0) tetrakis-triphenylphosphine); $POCl_3$ (phosphorous oxychloride); PS-DIEA (polystyrene diisopropylethylamine); PS-PPh$_3$ (polystyrenetriphenyl phosphine); PTSA (para-toluene sulfonic acid); Pyr (pyridine); Selectfluor (1-chloromethyl-4-fluoro-1,4-diazoniabicyclo[2.2.2]octane bis(tetrafluoroborate); TBAF (tetrabutylammonium fluoride); t-BuOH (tert-butanol); THF (tetrahydrofuran); Tf (trifluoromethanesulfonyl); TFA (trifluoroacetic acid); and TMSCH$_2$N$_2$ (trimethylsilyldiazomethane).

The compounds of this invention may be prepared by employing reactions as shown in the following Examples, in addition to other standard manipulations that are known in the literature or exemplified in the experimental procedures.

Example 1
1-({5-[1-(Cyclopropylmethyl)-4-(trifluoromethyl)-1H-benzotriazol-5-yl]-6-fluoropyridin-2-yl}methyl)-3-methylimidazolidine-2,4-dione
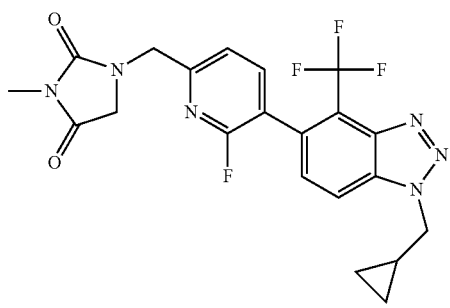 [SMILES: CN1C(=O)CN(Cc2ccc(-c3ccc4c(nnn4CC4CC4)c3C(F)(F)F)c(F)n2)C1=O]
Scheme for the Preparation of Example 1:
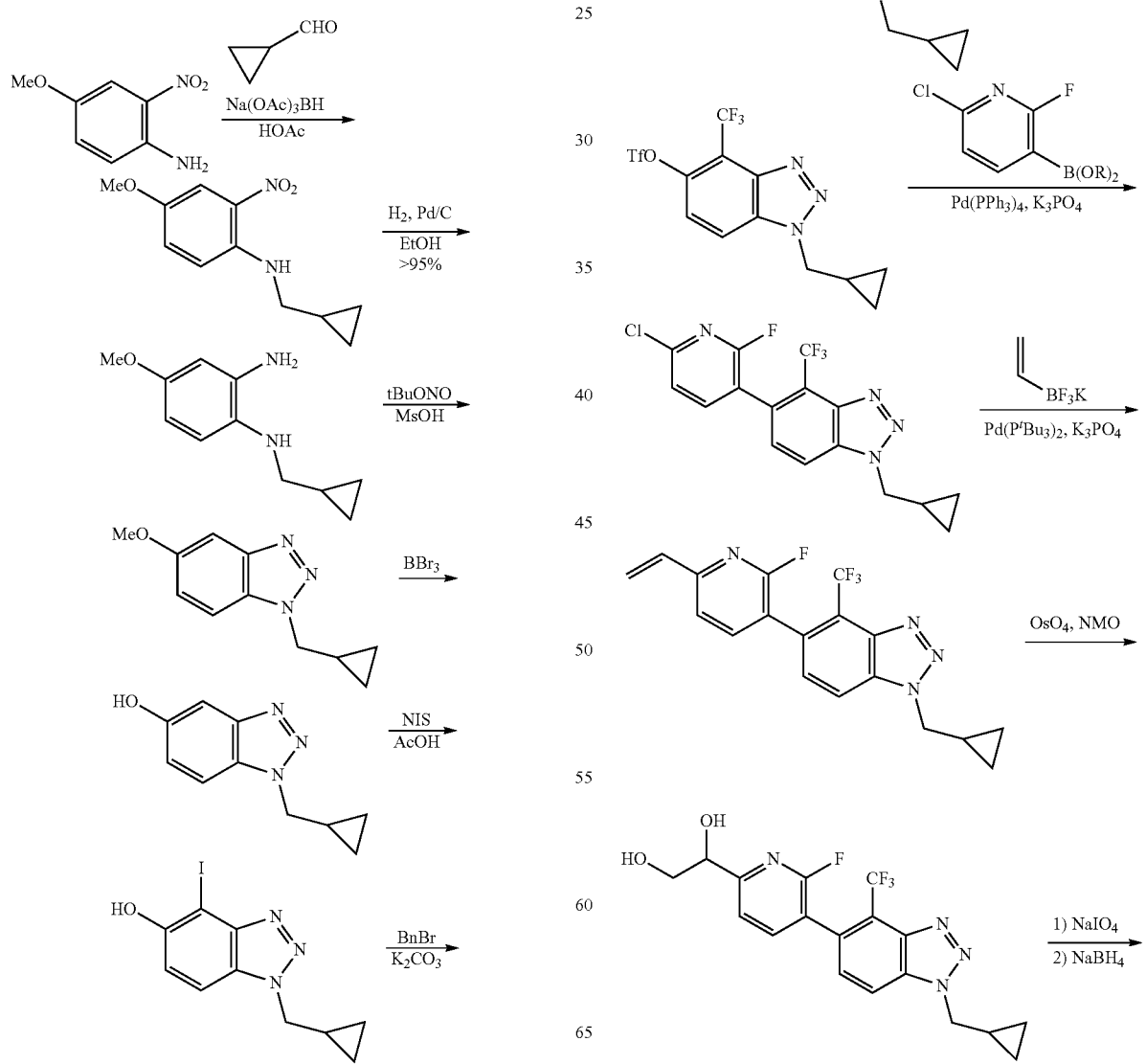

-continued

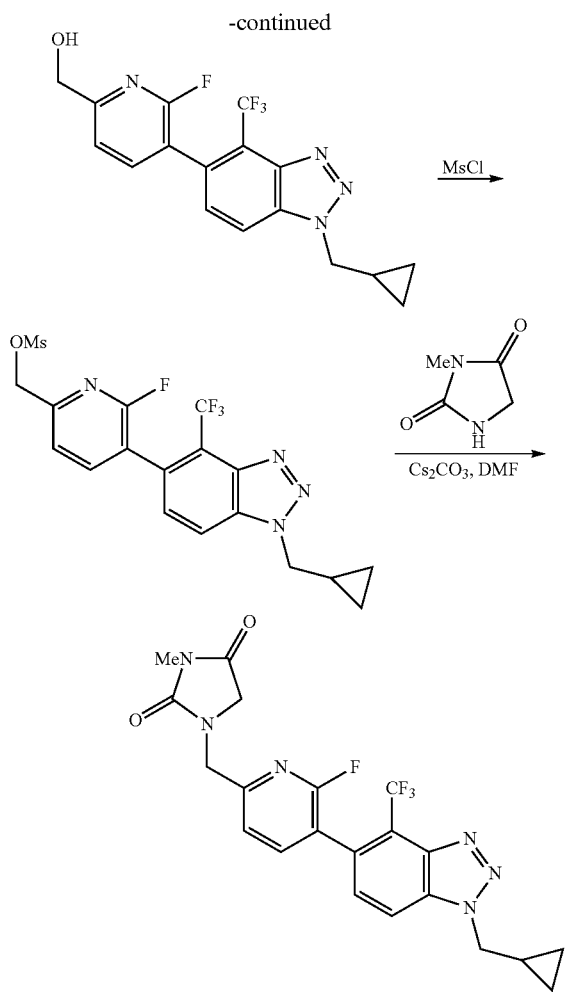

Step 1 Preparation of N-(cyclopropylmethyl)-4-methoxy-2-nitroaniline

A 5 L vessel was charged 4-methoxy-2-nitroaniline (160 g, 952 mmol) in dichloromethane (2.44 L). The mixture was cooled to 10° C. and cyclopropanecarboxaldehyde (100 g, 143 mmol) was added in four 25 gram portions. The vessel was charged with acetic acid (300 ml, 523 mmol) via an addition funnel and charged to the reaction mixture over 20 minutes. After 45 minutes, the vessel was charged with sodium triacetoxyborohydride (444 g, 209 mmol) portionwise. The mixture was warmed to ambient temperature over 4 hours and was stirred for an additional 14 hours. The mixture was treated with saturated aqueous sodium bicarbonate (100 mL) and poured into sodium bicarbonate (4 L) and dichloromethane. The organic extract was concentrated in vacuo, providing the titled compound.

Step 2 Preparation of $N^1$-(cyclopropylmethyl)-4-methoxybenzene-1,2-diamine N-(Cyclopropylmethyl)-4-methoxy-2-nitroaniline (175 g) was dissolved in ethanol (1750 mL) and added to a 4.0 L Hast 'C' Shaker can. The mixture was cooled to 10° C. and treated with 3% Pt/0.6% VG/C, deGussa (4.5 g). The vessel was sparged under nitrogen and then sparged three times with hydrogen at a setting of 40 psi and agitated for 2.5 hours. To a pre-washed solka-flok with ethanol, the mixture was filtered through solka-flok through a sintered glass funnel to have about a ½ inch depth of solka-flok. The solka-flok was then washed with 1 L ethanol and concentrated in vacuo, providing the titled compound.

Step 3 Preparation of 1-(cyclopropylmethyl)-5-methoxy-1H-benzotriazole $N^1$-(Cyclopropylmethyl)-4-methoxybenzene-1,2-diamine (10.8 g, 56.2 mmol) was dissolved in ethanol (80 mL) and treated with methanesulfonic acid (3.65 ml, 56.2 mmol) followed by isoamyl nitrite (7.56 ml, 56.2 mmol). The mixture was stirred for 15 minutes, diluted with ethyl acetate (1500 mL) and washed with aqueous saturated sodium bicarbonate (500 mL×2). The organic extracts were concentrated in vacuo and the residue was purified by silica gel gradient chromatography (5-50% ethyl acetate in heptanes), providing the titled compound as a tan solid.

Step 4 Preparation of 1-(cyclopropylmethyl)-1H-benzotriazol-5-ol 1-(Cyclopropylmethyl)-5-methoxy-1H-benzotriazole (11.0 g, 54.1 mmol) was dissolved in dichloromethane (200 mL) and cooled to 0° C. The mixture was treated with boron tribromide (108 mL, 1 M dichloromethane solution, 108 mmol, 2 equiv) and warmed to ambient temperature. After stirring for 3 hours, the mixture was treated with sodium bicarbonate over 1 hour (~100 mL, aqueous saturated) and the mixture was stirred for an additional 14 hours. The mixture was neutralized to pH<5 with 12 N aqueous hydrochloric acid dropwise and the mixture was extracted with dichloromethane containing 10% methanol (4×750 mL). The combined organic extracts were dried with sodium sulfate, filtered and concentrated in vacuo, providing the titled compound.

Step 5 Preparation of 1-(cyclopropylmethyl)-4-iodo-1H-benzotriazol-5-ol 1-(Cyclopropylmethyl)-1H-benzotriazol-5-ol (5.41 g, 28.6 mmol) was dissolved in acetic acid (75 mL) and treated with N-iodosuccinimide (4.79 g, 21.3 mmol, 0.74 equiv) portionwise. After 15 minutes, the mixture was diluted with water (150 mL) and extracted with dichloromethane (2×100 mL). The combined organic extracts were dried with sodium sulfate, filtered and concentrated in vacuo, providing the titled compound.

Step 6 Preparation of 5-benzyloxy-1-(cyclopropylmethyl)-4-iodo-1H-benzotriazole 1-(Cyclopropylmethyl)-4-iodo-1H-benzotriazol-5-ol (9.01 g, 28.6 mmol) was suspended in degassed N,N-dimethylformamide (75 mL) and treated with benzylbromide (3.74 mL, 31.5 mmol, 1.1 equiv) and potassium carbonate (19.8 g, 143 mmol, 5 equiv). The mixture was placed into a preheated oil bath at 50° C. for 30 minutes, cooled to ambient temperature, and diluted with water (500 mL). The mixture was extracted with dichloromethane (2×500 mL) and the combined organic extracts were dried with sodium sulfate, filtered and concentrated in vacuo, providing the titled compound.

Step 7 Preparation of 5-benzyloxy-1-(cyclopropylmethyl)-4-(trifluoromethyl)-1H-benzotriazole 5-Benzyloxy-1-(cyclopropylmethyl)-4-iodo-1H-benzotriazole (1.29 g, 3.2 mmol), copper(I) iodide (1.21 g, 6.39 mmol, 2 equiv) and methyl 2,2-difluoro-2-(fluorosulfonyl) acetate (1.33 mL, 6.39 mmol, 2 equiv) were combined in degassed N,N-dimethylformamide (25 mL) at ambient temperature and placed into a preheated oil bath at 100° C. for 1.5 hours. The mixture was cooled to ambient temperature, poured into water (200 mL), treated with ethyl acetate (100 mL) and Celite. The mixture was aged for 30 minutes, filtered, and partitioned. The aqueous layer was further extracted with ethyl acetate (2×100 mL) and the combined organic extracts were washed with sodium bicarbonate (100 mL, aqueous saturated) and brine (50 mL), dried with sodium sulfate, filtered and concentrated in vacuo. The residue was purified by silica gel gradient chromatography (100:0 to 25:75; hexanes:ethyl acetate), providing the titled compound as a colorless oil.

Step 8 Preparation of 1-(cyclopropylmethyl)-4-(trifluoromethyl)-1H-benzotriazol-5-ol 5-Benzyloxy-1-(cyclopropylmethyl)-4-(trifluoromethyl)-1H-benzotriazole (5.04 g, 14.5 mmol) was dissolved in 1:1 mixture of methanol/ethyl acetate (40 mL). The mixture was sparged under nitrogen, treated with Pearlman's catalyst (2 g, 0.2 wt equiv) and then sparged under hydrogen (1 atm) and stirred vigorously for 90 minutes. The mixture was filtered through a pad of Celite, which was washed with methanol (500 mL) and concentrated in vacuo, providing the titled compound.

Step 9 Preparation of 1-(cyclopropylmethyl)-4-(trifluoromethyl)-1H-benzotriazol-5-yl trifluoromethanesulfonate 1-(Cyclopropylmethyl)-4-(trifluoromethyl)-1H-benzotriazol-5-ol (0.80 g, 3.1 mmol) was suspended in dichloromethane (20 mL) and treated with N,N-diisopropylethylamine (1.6 mL, 9.4 mmol, 3 equiv), upon which the mixture became homogeneous. The mixture was cooled to 0° C., treated with trifluoromethanesulfonic anhydride (0.80 mL, 4.7 mmol, 1.5 equiv) and stirred for 20 minutes. The mixture was poured into water (50 mL) and extracted with dichloromethane (2×50 mL). The combined organic extracts were dried with sodium sulfate, filtered and concentrated in vacuo. The residue was purified by silica gel gradient chromatography (100:0 to 0:100; hexanes:ethyl acetate), providing the titled compound.

Step 10 Preparation of 5-(6-chloro-2-fluoropyridin-3-yl)-1-(cyclopropylmethyl)-4-(trifluoromethyl)-1H-benzotriazole 1-(Cyclopropylmethyl)-4-(trifluoromethyl)-1H-benzotriazol-5-yl trifluoromethanesulfonate (221 mg, 0.568 mmol) and (6-chloro-2-fluoropyridin-3-yl)boronic acid (130 mg, 0.738 mmol, 1.3 equiv) were dissolved in degassed dioxane (5.6 mL) and treated with potassium phosphate (0.37 mL, 2 M aqueous, 0.74 mmol, 1.3 equiv) and palladium tetrakis(triphenylphosphine) (98 mg, 0.085 mmol, 0.15 equiv). The mixture was placed into a preheated oil bath at 90° C. for 3 hours, cooled to ambient temperature, diluted with ethyl acetate (40 mL) and washed with sodium bicarbonate (2×30 mL, aqueous saturated). The combined organic extracts were dried with sodium sulfate, filtered and concentrated in vacuo. The residue was purified by silica gel gradient chromatography (100:0 to 70:30; hexanes:ethyl acetate), providing the titled compound.

Step 11 Preparation of 1-(cyclopropylmethyl)-5-(6-ethenyl-2-fluoropyridin-3-yl)-4-(trifluoromethyl)-1H-benzotriazole 5-(6-Chloro-2-fluoropyridin-3-yl)-1-(cyclopropylmethyl)-4-(trifluoromethyl)-1H-benzotriazole (135 mg, 0.37 mmol) was dissolved in degassed tetrahydrofuran (3.3 mL) and treated with potassium trifluoro(vinyl)borate (174 mg, 1.3 mmol, 4 equiv), cesium carbonate (154 mg, 0.47 mmol, 1.3 equiv) and bis(tri-tert-butylphosphine)palladium(0) (56 mg, 0.11 mmol, 0.3 equiv). The mixture was placed into a preheated oil bath at 65° C. for 1.5 hours, cooled to ambient temperature, diluted with ethyl acetate (50 mL) and washed with sodium bicarbonate (2×30 mL, aqueous saturated). The combined organic extracts were dried with sodium sulfate, filtered and concentrated in vacuo. The residue was purified by silica gel chromatography (100% dichloromethane), providing the titled compound.

Step 12 Preparation of 1-{5-[1-(cyclopropylmethyl)-4-(trifluoromethyl)-1H-benzotriazol-5-yl]-6-fluoropyridin-2-yl}ethane-1,2-diol 1-(Cyclopropylmethyl)-5-(6-ethenyl-2-fluoropyridin-3-yl)-4-(trifluoromethyl)-1H-benzotriazole (77 mg, 0.21 mmol) was dissolved in tetrahydrofuran (1.4 mL) and treated with osmium tetraoxide (270 uL, 0.043 mmol, 0.2 equiv) and N-methylmorpholine N-oxide (25 mg, 0.21 mmol, 1 equiv). After stirring at ambient temperature for 1.5 hours, the mixture was diluted with ethyl acetate (40 mL) and washed with sodium bicarbonate (2×30 mL, aqueous saturated). The combined organic extracts were dried with sodium sulfate, filtered and concentrated in vacuo, providing the titled compound.

Step 13 Preparation of 5-[1-(cyclopropylmethyl)-4-(trifluoromethyl)-1H-benzotriazol-5-yl]-6-fluoropyridine-2-carbaldehyde 1-{5-[1-(Cyclopropylmethyl)-4-(trifluoromethyl)-1H-benzotriazol-5-yl]-6-fluoropyridin-2-yl}ethane-1,2-diol (32 mg, 0.081 mmol) was dissolved in acetonitrile (1 ml) and deionized water (0.5 mL), cooled to 0° C. and treated with sodium periodate (19 mg, 0.089 mmol, 1.1 equiv). The ice bath was removed and the mixture was warmed to ambient temperature and stirred for 1 hour, which was diluted with ethyl acetate (30 mL) and washed with sodium bicarbonate (2×15 mL, aqueous saturated). The combined organic extracts were dried with sodium sulfate, filtered and concentrated in vacuo, providing the titled compound.

Step 14 Preparation of {5-[1-(cyclopropylmethyl)-4-(trifluoromethyl)-1H-benzotriazol-5-yl]-6-fluoropyridin-2-yl}methanol 5-[1-(Cyclopropylmethyl)-4-(trifluoromethyl)-1H-benzotriazol-5-yl]-6-fluoropyridine-2-carbaldehyde (33 mg, 0.091) was dissolved in dichloromethane (2 mL) and cooled to 0° C. The mixture was treated with sodium borohydride (8.6 mg, 0.23 mmol, 2.5 equiv) and after 2 hours, the mixture was diluted with ethyl acetate (30 mL), washed with sodium bicarbonate (2×30 mL, aqueous saturated), dried with sodium sulfate, filtered and concentrated in vacuo. The residue was purified by silica gel gradient chromatography, providing the titled compound.

Step 15 Preparation of {5-[1-(cyclopropylmethyl)-4-(trifluoromethyl)-1H-benzotriazol-5-yl]-6-fluoropyridin-2-yl}methyl methanesulfonate {5-[1-(Cyclopropylmethyl)-4-(trifluoromethyl)-1H-benzotriazol-5-yl]-6-fluoropyridin-2-yl}methanol (20 mg, 0.055 mmol) was dissolved in dichloromethane (0.36 mL), cooled to 0° C. and treated with triethylamine (0.023 mL, 0.16 mmol) followed by methanesulfonyl chloride (4.7 uL, 0.060 mmol). The mixture was warmed to room temperature and stirred until complete, at which time the mixture was diluted with ethyl acetate and washed with sodium bicarbonate (2×5 mL, aqueous saturated). The organic layer was dried with sodium sulfate, filtered and concentrated in vacuo, providing the titled compound.

Step 16 Preparation of 3-methylhydantoin

Hydantoin (19.0 g, 190 mmol, 1.0 eq) was suspended in toluene (700 ml) and N,N-dimethylacetamide dimethyl acetal (75.0 g, 563 mmol, 3.0 eq) was added. The resulting mixture was heated at 110° C. for two hours, cooled to ambient temperature and then cooled to 0° C. for 15 minutes. The resulting precipitate was collected by filtration, washed with toluene (5×50 mL) and dried in vacuo to afford the titled compound as a pale yellow solid. $^1$H NMR (400 MHz, CDCl$_3$) δ 6.09 (1H, brs); 3.99 (1H, s); 3.04 (1H, s) ppm.

Step 17 Preparation of 1-({5-[1-(cyclopropylmethyl)-4-(trifluoromethyl)-1H-benzotriazol-5-yl]-6-fluoropyridin-2-yl}methyl)-3-methylimidazolidine-2,4-dione {5-[1-(Cyclopropylmethyl)-4-(trifluoromethyl)-1H-benzotriazol-5-yl]-6-fluoropyridin-2-yl}methyl methanesulfonate (25 mg, 0.056 mmol) was dissolved in acetonitrile (0.56 mL) and treated with 3-methylimidazolidine-2,4-dione (9.6 mg, 0.084 mmol), cesium carbonate (55 mg, 0.17 mmol) and tetra-n-butylammonium iodide (4.2 mg, 0.011 mmol). The mixture was placed into a preheated oil bath at 85° C. for 30 minutes. The mixture was cooled to ambient temperature, diluted with ethyl acetate and washed with sodium bicarbonate (2×5 mL, aqueous saturated). The organic layer was dried with sodium sulfate, filtered and concentrated in vacuo. The residue was purified by preparative reverse phase HPLC (85: 15 to 36:64; water with 0.05% trifluoroacetic acid:acetonitrile with 0.05% trifluoroacetic acid) to afford the titled compound as a white solid. H$^1$-NMR (400 MHz, CDCl$_3$): δ 7.84 (1H, d, J=8.5 Hz), 7.77 (1H, dd, J=9.2, 7.6 Hz), 7.39 (1H, d, J=8.6 Hz), 7.30 (1H, dd, J=7.5, 1.5 Hz), 4.77 (1H, d, J=16.4 Hz), 4.67 (1H, d, J=16.2 Hz), 4.61 (2H, d, J=7.1 Hz), 4.16 (1H, d, J=17.4 Hz), 4.07 (1H, d, J=17.1 Hz), 3.32 (3H, s), 1.49-1.39 (1H, m), 0.78-0.66 (2H, m), 0.61-0.11 (2H, m) ppm; high resolution mass spectrometry (ES+) m/z 463.1514 [(M+H)$^+$; calculated for C$_{21}$H$_{19}$F$_4$N$_6$O$_2$: 463.1500].

Example 2

1-{4-[1-(Cyclopropylmethyl)-4-(trifluoromethyl)-1H-benzotriazol-5-yl]benzyl}-3-methylimidazolidine-2,4-dione

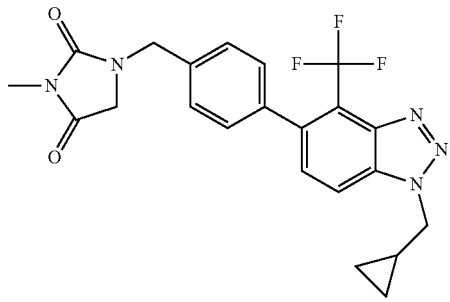 [SMILES: CN1C(=O)CN(Cc2ccc(-c3ccc4c(nnn4CC4CC4)c3C(F)(F)F)cc2)C1=O]

Scheme for the Preparation of Example 2:

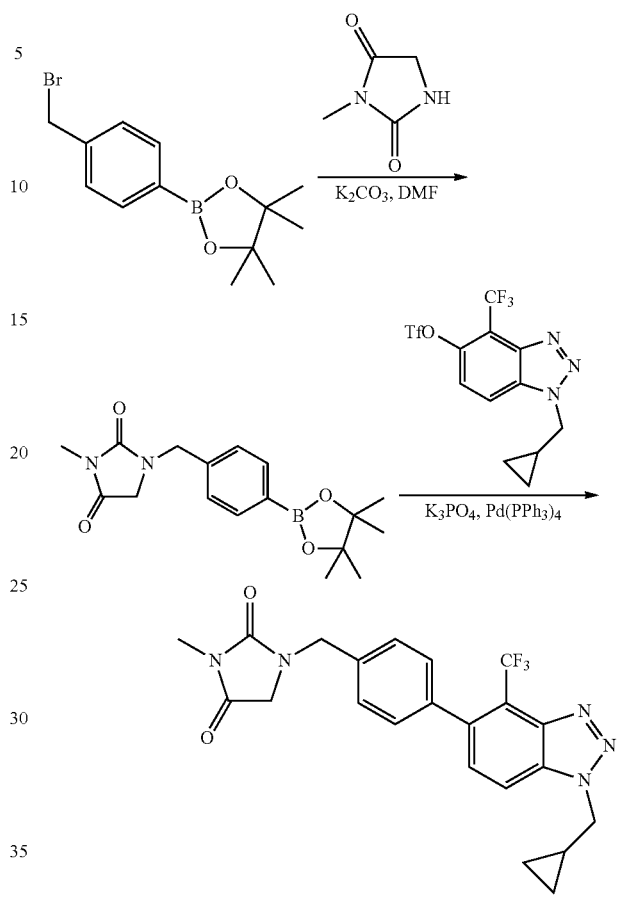

Step 1 Preparation of 3-methyl-1-[4-(4,4,5,5-tetramethyl-1,3,2-dioxaborolan-2-yl)benzyl]imidazolidine-2,4-dione 2-[4-(Bromomethyl)phenyl]-4,4,5,5-tetramethyl-1,3,2-dioxaboronate (5.00 g, 16.84 mmol), 3-methylimidazolidine-2,4-dione (2.11 g, 18.52 mmol, 1.1 equiv) and potassium carbonate (4.65 g, 33.7 mmol, 2 equiv) were combined and treated with N,N-dimethylformamide (17 mL). The mixture heated for 3 hours at 45° C., cooled to ambient temperature, diluted with ethyl acetate and washed with water (3×) and brine. The organic extracts were dried with sodium sulfate, filtered and concentrated in vacuo to afford the titled compound.

Step 2 1-{4-[1-(cyclopropylmethyl)-4-(trifluoromethyl)-1H-benzotriazol-5-yl]benzyl}-3-methylimidazolidine-2,4-dione 1-(Cyclopropylmethyl)-4-(trifluoromethyl)-1H-benzotriazol-5-yltrifluoromethanesulfonate [(Example 1, Step 9), 30 mg, 0.077 mmol], 3-methyl-1-[4-(4,4,5,5-tetramethyl-1, 3,2-dioxaborolan-2-yl)benzyl]imidazolidine-2,4-dione (38.2 mg, 0.116 mmol, 1.5 equiv), potassium phosphate (49.1 mg, 0.231 mmol, 3 equiv) and palladium tetrakis(triphenylphosphine) (8.91 mg, 0.007 mmol, 0.1 equiv) were combined in dioxane (2 mL) and water (0.2 mL) and heated at 90° C. for 1 hour. The mixture was cooled to ambient temperature, poured into sodium bicarbonate (15 mL, saturated aqueous) and extracted with ethyl acetate (2×25 mL). The combined organic extracts were dried with sodium sulfate, filtered and concentrated in vacuo. The residue was purified via preparative reverse phase HPLC (80:20 to 5:95; water with 0.05% trifluoroacetic acid:acetonitrile with 0.05% trifluoroacetic acid) to afford the titled compound: $^1$H NMR (400 MHz, CDCl$_3$) δ 7.69 (1H, d, J=8.5 Hz), 7.34 (1H, d, J=8.5 Hz), 7.28 (4H, dd, J=8.8, 8.1 Hz), 4.58 (2H, s), 4.52 (2H, d, J=7.1 Hz), 3.74 (2H, s), 3.01 (3H, s), 1.40-1.32 (1H, m), 0.65-0.60 (2H, m), 0.48-0.44 (2H, m) ppm; high resolution mass spectrometry (ES+) m/z 444.1652 [(M+H)$^+$; calculated for C$_{22}$H$_{21}$F$_3$N$_5$O$_2$: 444.1642].

The following compound was prepared according to the general procedure described in Examples 1 and 2. The starting materials are either commercially available, known in the literature or may be prepared from commercially available reagents using conventional reactions well known in the art.

| Ex. | STRUCTURE | NAME | HRMS/LRMS |
|---|---|---|---|
| 3 | 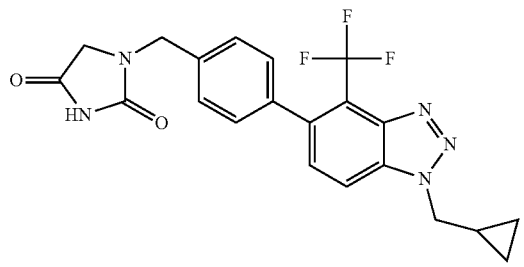 [SMILES: O=C1CN(Cc2ccc(-c3ccc4c(nnn4CC4CC4)c3C(F)(F)F)cc2)C(=O)N1] | 1-{4-[4-bromo-1-(cyclopropylmethyl)-1H-benzotriazol-6-yl]benzyl}-3-methylimidazolidine-2,4-dione | C$_{21}$H$_{19}$BrN$_5$O$_2$ [M + H] Calc'd 456.3 found 456.0 |

Example 4

1-{4-[1-(Cyclopropylmethyl)-4-(trifluoromethyl)-1H-benzotriazol-5-yl]benzyl}imidazolidine-2,4-dione

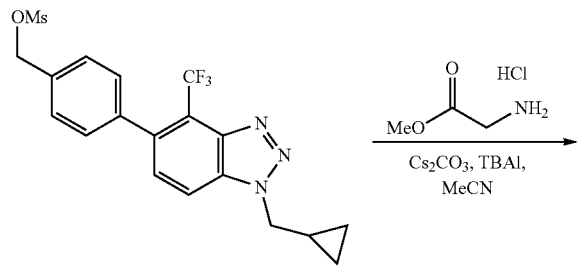

Scheme for the Preparation of Example 4:

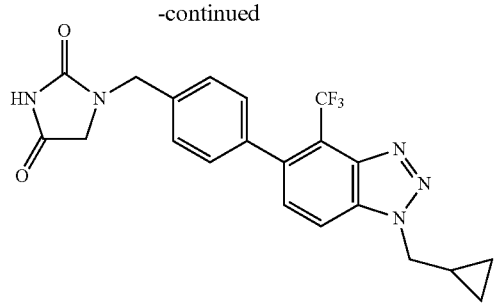

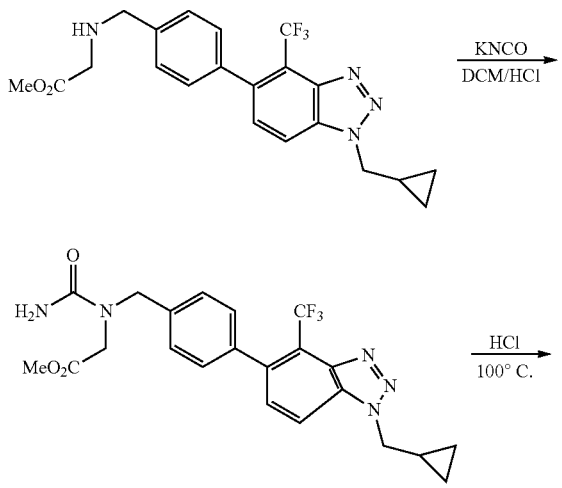

Step 1 Preparation of ethyl N-{4-[1-(cyclopropylmethyl)-4-(trifluoromethyl)-1H-benzotriazol-5-yl]benzyl}glycinate 4-[1-(Cyclopropylmethyl)-4-(trifluoromethyl)-1H-benzotriazol-5-yl]benzyl methanesulfonate (0.12 mg, 0.28 mmol) was dissolved in acetonitrile (2.8 mL) and treated the mixture with ethyl aminoacetate hydrochloride (150 mg, 1.1 mmol), cesium carbonate (270 mg, 0.824 mmol) and tetra-n-butylammonium iodide (51 mg, 0.14 mmol). The mixture was placed into an oil bath preheated to 85° C. and stirred for 2 h, at which time the mixture was cooled to ambient temperature, diluted with ethyl acetate and washed with sodium bicarbonate (2×30 mL, aqueous saturated). The organic layer was dried over sodium sulfate, filtered and concentrated in vacuo. The residue was purified by reverse phase preparative HPLC (85:15 to 42:58; water with 0.05% trifluoroacetic acid:acetonitrile with 0.05% trifluoroacetic acid) to afford the titled compound.

Step 2 Preparation of ethyl N-carbamoyl-N-{4-[1-(cyclopropylmethyl)-4-(trifluoromethyl)-1H-benzotriazol-5-yl]benzyl}glycinate Ethyl N-{4-[1-(cyclopropylmethyl)-4-(trifluoromethyl)-1H-benzotriazol-5-yl]benzyl}glycinate (42 mg, 0.097 mmol) was added to a dichloromethane:1 N hydrochloric acid solution (400 µL:80 µL) and the mixture placed into an ice-bath at 0° C. Potassium cyanate (24 mg, 0.29 mmol) was dissolved in deionized water (300 uL) and this solution was added to the mixture over 5 minutes. The mixture was vigorously stirred for 1.5 hours, at which time the mixture was treated with sodium bicarbonate (aqueous saturated) and extracted with ethyl acetate (3×40 mL). The organic layers were combined, dried with sodium sulfate, filtered and concentrated in vacuo to provide the titled compound.

Step 3 Preparation of 1-{4-[1-(cyclopropylmethyl)-4-(trifluoromethyl)-1H-benzotriazol-5-yl]benzyl}imidazolidine-2,4-dione Ethyl N-carbamoyl-N-{4-[1-(cyclopropylmethyl)-4-(trifluoromethyl)-1H-benzotriazol-5-yl]benzyl}glycinate was dissolved in a dichloromethane/1 N hydrochloric acid solution and the reaction mixture placed into an oil-bath preheated to 100° C. The mixture was stirred for 1.5 hours, cooled to ambient temperature, diluted with water and extracted with ethyl acetate (3×30 mL). The organic layers were combined, dried over sodium sulfate and concentrated in vacuo to afford the titled compound as a white solid. $H^1$-NMR (400 MHz, $CDCl_3$): δ 8.87 (1H, s), 7.70 (1H, d, J=8.6 Hz), 7.35 (1H, d, J=8.6 Hz), 7.30 (2H, d, J=8.3 Hz), 7.26 (2H, d, J=8.3 Hz), 4.55 (2H, s), 4.53 (2H, d, J=7.2 Hz), 3.80 (2H, s), 1.60-1.49 (1H, m), 0.69-0.57 (2H, m), 0.52-0.41 (2H, m) ppm; high resolution mass spectrometry (ES+) m/z 430.1509 [(M+H)$^+$; calculated for $C_{21}H_{19}F_3N_5O_2$: 430.1485].

Example 5

(2S)—N-{4-[1-(Cyclopropylmethyl)-4-(trifluoromethyl)-1H-benzotriazol-5-yl]benzyl}-2-hydroxypropanamide

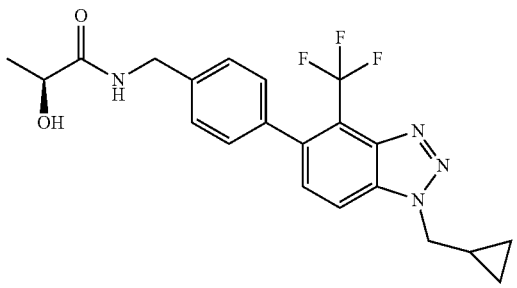 [SMILES: C[C@H](O)C(=O)NCc1ccc(-c2ccc3c(nnn3CC3CC3)c2C(F)(F)F)cc1]

Scheme for the Preparation of Example 5:

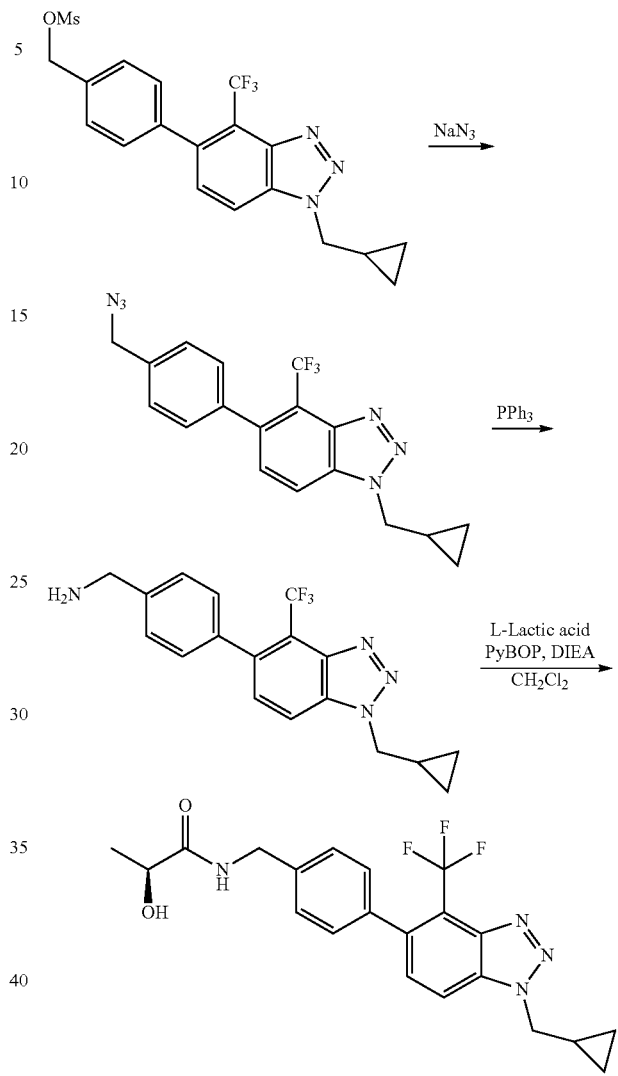

Step 1 Preparation of 4-[1-(cyclopropylmethyl)-4-(trifluoromethyl)-1H-benzotriazole-5-yl]benzyl methanesulfonate 4-[1-(Cyclopropylmethyl)-4-(trifluoromethyl)-1H-benzotriazole-5-yl]benzyl methanesulfonate was prepared according to the procedures described in Example 1, substituting 2-[4-(hydroxymethyl)phenyl]-4,4,5,5-tetramethyl-1,3,2-dioxaboronate for (6-chloro-2-fluoropyridin-3-yl)boronic acid (Step 10).

Step 2 Preparation of 5-[4-(azidomethyl)phenyl]-1-(cyclopropylmethyl)-4-(trifluoromethyl)-1H-benzotriazole 4-[1-(Cyclopropylmethyl)-4-(trifluoromethyl)-1H-benzotriazole-5-yl]benzyl methanesulfonate (185 mg, 0.435 mmol) was dissolved in dimethylsulfoxide, treated with sodium azide (141 mg, 2.17 mmol, 5 equiv) and placed into a preheated oil bath at 70° C. for 30 minutes. The mixture was cooled to ambient temperature, poured into water (150 mL)

and extracted with ethyl acetate (2×100 mL). The combined organic extracts were dried with sodium sulfate, filtered and concentrated in vacuo, providing the titled compound.

Step 3 Preparation of 1-{4-[1-(cyclopropylmethyl)-4-(trifluoromethyl)-1H-benzotriazol-5-yl]phenyl}methanamine 5-[4-(Azidomethyl)phenyl]-1-(cyclopropylmethyl)-4-(trifluoromethyl)-1H-benzotriazole (162 mg, 0.435 mmol) and triphenylphosphine (342 mg, 1.30 mmol, 3 equiv) were combined in tetrahydrofuran (10 mL) at ambient temperature. After stirring for 5 minutes, the mixture was placed into a preheated oil bath at 50° C. for 2 hours. The mixture was treated with sodium bicarbonate (1.5 mL, aqueous saturated) and heated for an additional 1 hour at 50° C. The mixture was cooled to ambient temperature, poured into water (25 mL) and extracted with ethyl acetate (2×50 mL). The combined organic extracts were washed with brine (25 mL), dried with sodium sulfate, filtered and concentrated in vacuo. The residue was purified by silica gel gradient chromatography (100:0 to 80:20; dichloromethane:methanol containing 10% ammonium hydroxide), providing the titled compound as a light green gum.

Step 3 Preparation of (2S)—N-{4-[1-(cyclopropylmethyl)-4-(trifluoromethyl)-1H-benzotriazol-5-yl]benzyl}-2-hydroxypropanamide 1-{4-[1-(Cyclopropylmethyl)-4-(trifluoromethyl)-1H-benzotriazol-5-yl]phenyl}methanamine (19 mg, 0.055 mmol), L-lactic acid (9.9 mg, 0.11 mmol, 2 equiv), N,N-diisopropylethylamine (48 μL, 0.27 mmol, 5 equiv) and (1H-benzotriazol-1-yloxy)(tripyrrolidin-1-yl)phosphonium tetrafluoroborate (43 mg, 0.082 mmol, 1.5 equiv) were combined in dichloromethane (1.5 mL) and stirred for 15 minutes. The mixture was concentrated in vacuo and the residue was purified by preparative reverse phase HPLC (95:5 to 5:95; water containing 0.1% trifluoroacetic acid:acetonitrile containing 0.1% trifluoroacetic acid), providing the titled compound: $^1$H-NMR (400 MHz, d$^6$-DMSO) δ 8.33 (1H, t, J=6.9 Hz), 8.30 (1H, d, J=8.5 Hz), 7.51 (1H, d, J=8.7 Hz), 7.36-7.32 (4H, m), 4.72 (2H, d, J=7.2 Hz), 4.41-4.33 (2H, m), 4.08-4.03 (1H, m), 1.46-1.38 (1H, m), 1.27 (3H, d, J=6.6 Hz), 0.60-0.55 (2H, m), 0.53-0.50 (2H, m) ppm; high resolution mass spectrometry (ES+) m/z 419.1700 [(M+H)$^+$; calculated for $C_{21}H_{22}F_3N_4O_2$: 419.1689].

The following compound was prepared according to the general procedure described in Example 5, substituting the appropriate acid for L-lactic acid (Step 3). The starting materials are either commercially available, known in the literature or may be prepared from commercially available reagents using conventional reactions well known in the art.

| Ex. | STRUCTURE | NAME | HRMS/LRMS |
|---|---|---|---|
| 6 | (structure) | (2R)-N-{4-[1-(cyclopropylmethyl)-4-(trifluoromethyl)-1H-benzotriazol-5-yl]benzyl}-2-hydroxypropanamide | $C_{21}H_{22}F_3N_4O_2$ [M + H] Calc'd 419.1689 found 419.1697 |

Example 7

1-{4-[4-Bromo-1-(2,2-dimethylpropyl)-1H-benzotriazol-5-yl]benzyl}-4-methyl-1,2,4-triazolidine-3,5-dione

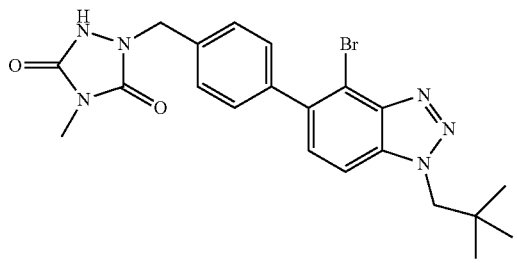 [SMILES: Cn1c(=O)[nH]n(Cc2ccc(-c3ccc4c(nnn4CC(C)(C)C)c3Br)cc2)c1=O]

Scheme for Preparation of Example 7:

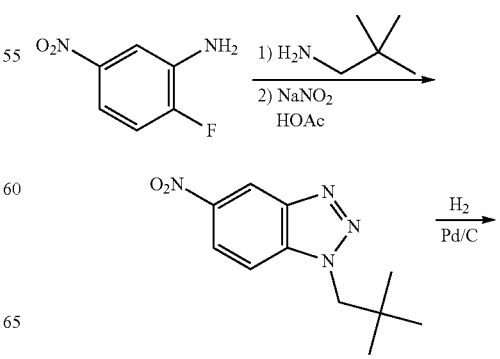

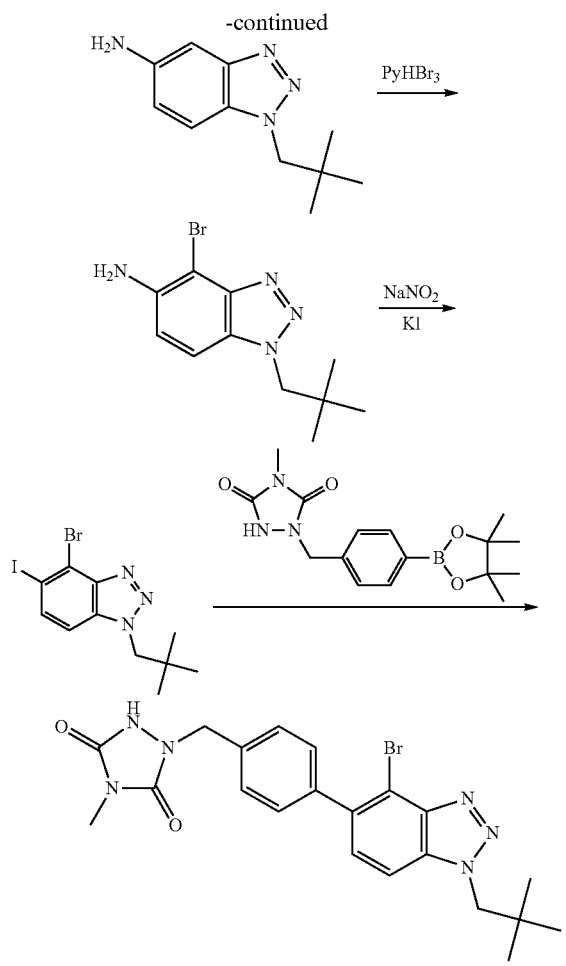

Step 1 Preparation of 1-(2,2-dimethylpropyl)-5-nitro-1H-1,2,3-benzotriazole

2-Fluoro-5-nitroaniline (10.22 g, 65.5 mmol, 1.0 equiv.) was dissolved in anhydrous dimethylsulfoxide (100 ml) and treated with neopentylamine (7.71 ml, 65.5 mmol, 1.0 equiv.). The mixture was heated at 120° C. for 2 days, cooled to room temperature and treated with acetic acid (25 ml), followed by addition of 0.65 M aqueous solution of sodium nitrite (121 ml, 79 mmol, 1.2 equiv.). After stirring at ambient temperature for 20 minutes, the mixture was neutralized to pH 7 with NaOH (1 N aqueous) and diluted with water, which caused precipitation. The solid was collected by filtration and washed twice with water. The residue was purified via silica gel chromatography (ethyl acetate/hexane gradient from 0 to 100%) to provide the titled compound: $^1$H NMR (500 MHz, CDCl$_3$) δ 9.02 (d, 1H, J=2.0 Hz), 8.40 (dd, 1H, J=9.1, 2.0 Hz), 7.62 (d, 1H, J=9.1 Hz), 4.47 (s, 2H), 1.07 (s, 9H) ppm. LRMS m/z (M+H) 235.1 found, 235.3 required.

Step 2 Preparation of 1-(2,2-dimethylpropyl)-1H-1,2,3-benzotriazol-5-amine 1-(2,2-Dimethylpropyl)-5-nitro-1H-1,2,3-benzotriazole (4.46 g, 19.04 mmol, 1.0 equiv.) was dissolved in ethanol (50 ml), sparged under an atmosphere of nitrogen and charged with 10% Pd/C (2.026 g, 1.904 mmol, 0.1 equiv.). The mixture was sparged under an atmosphere of hydrogen (1 atm) and stirred vigorously at ambient temperature for 5 hours. The mixture was filtered through Celite and the residue was washed with methanol. The filtrate was concentrated in vacuo, providing the titled compound. LRMS m/z (M+H) 205.0 found, 205.3 required.

Step 3 Preparation of 4-bromo-1-(2,2-dimethylpropyl)-1H-1,2,3-benzotriazol-5-amine 1-(2,2-Dimethylpropyl)-1H-1,2,3-benzotriazol-5-amine (3.52 g, 17.23 mmol, 1.0 equiv.) was dissolved in chloroform (172 ml) and treated with pyridinium tribromide (5.51 g, 17.23 mmol, 1.0 equiv.). The mixture was stirred at room temperature until LCMS showed almost only product was observed. The mixture was filtered and the solid was washed with hexane, which was dissolved in diethyl ether/ethyl acetate and neutralized with saturated aqueous sodium bicarbonate. The organic extracts were dried with magnesium sulfate, filtered and concentrated in vacuo, providing the titled compound as a pale white solid. $^1$H NMR (500 MHz, CD$_3$OD) δ 7.30 (d, 1H, J=8.8 Hz), 7.07 (sb, 3H), 7.02 (d, 1H, J=8.8 Hz), 4.34 (s, 2H), 1.03 (s, 9H) ppm. LRMS m/z (M+H) 283.0 and 285.0 (intensity ratio ~1:1) found, 283.1 and 285.1 required.

Step 4 Preparation of 4-bromo-1-(2,2-dimethylpropyl)-5-iodo-1H-benzotriazole

To a solution of para-toluenesulfonic acid monohydrate (510 mg, 2.68 mmol) in acetonitrile (3.5 mL), was added 4-bromo-1-(2,2-dimethylpropyl)-1H-1,2,3-benzotriazol-5-amine (253 mg, 0.893 mmol). The resulting suspension was cooled to 10-15° C. and treated with an aqueous solution of sodium nitrite (537 μl, 1.787 mmol) and potassium iodide (536 μl, 2.23 mmol). The mixture was stirred for 10 minutes at 0° C. and then warmed to ambient temperature. The mixture was diluted with water and treated with sodium bicarbonate (1 M, aqueous) until the mixture was adjusted to pH 9-10, which was followed by treatment of a 3 M aqueous solution of Na$_2$S$_2$O$_3$ (6 mL). The solid was collected by filtration and washed with cold diethyl ether and hexane. The residue was purified via silica gel chromatography (ethyl acetate/hexane gradient), providing the titled compound: $^1$H NMR (500 MHz, CDCl$_3$) δ 7.86 (d, 1H, J=8.7 Hz), 7.25 (d, 1H, J=9.0 Hz), 4.36 (s, 2H), 1.04 (s, 9H) ppm. LRMS m/z (M+H) 393.8 and 395.8 found, 393.9 and 395.9 required.

Step 5 Preparation of 4-bromo-1-(2,2-dimethylpropyl)-5-iodo-1H-1,2,3-benzotriazol-5-amine 4-Bromo-1-(2,2-dimethylpropyl)-5-iodo-1H-benzotriazole (65.4 mg, 0.166 mmol), 4-methyl-1-[4-(4,4,5,5-tetramethyl-1,3,2-dioxaborolan-2-yl)benzyl]-1,2,4-triazolidine-3,5-dione (50 mg, 0.151 mmol), PdCl$_2$(dppf)-dichloromethane adduct (6.16 mg, 7.55 mmol), and cesium carbonate (148 mg, 0.453 mmol) were combined in tetrahydrofuran (2 ml) and water (0.200 ml). The mixture was heated in a sealed tube at 60° C. for 24 hours, cooled to ambient temperature, treated with ethyl acetate and Celite. The mixture was filtered through celite and concentrated in vacuo. The residue was purified via preparative reverse phase HPLC (C-18), eluting with acetonitrile/water+0.1% TFA, providing the titled compound. $^1$H NMR (500 MHz, d$^6$-DMSO) δ 10.60 (s, 1H), 8.01 (d, J=8.5 Hz, 1H), 7.55 (d, J=8.5 Hz, 1H), 7.50 (d, J=7.9 Hz, 2H), 7.38 (d, J=7.9 Hz, 2H), 4.70 (s, 2H), 4.57 (s, 2H), 2.93 (s, 3H), 0.99 (s, 9H) ppm. LRMS m/z (M+H) 470.8 and 472.8 found, 471.1 and 473.1 required.

Example 8

1-{4-[4-Bromo-1-(2-methylpropyl)-1H-benzotriazol-5-yl]benzyl}-3-methylimidazolidine-2,4-dione

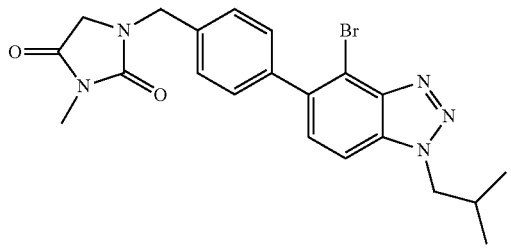 [SMILES: CC(C)Cn1nnc2c(Br)c(-c3ccc(CN4CC(=O)N(C)C4=O)cc3)ccc21]

Scheme for Example 8

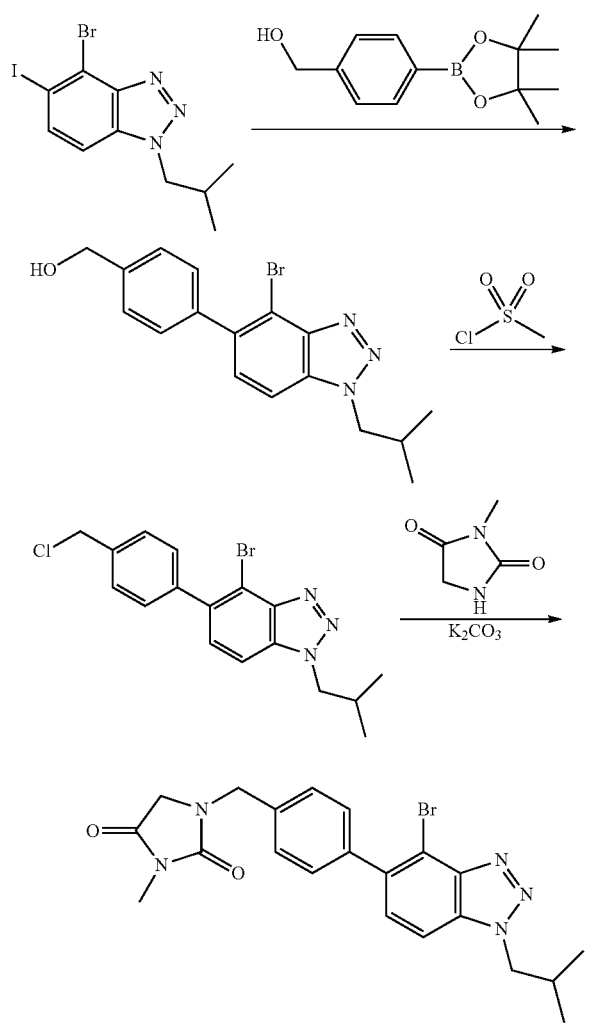

Step 1 Preparation of 4-bromo-5-iodo-1-(2-methylpropyl)-1H-benzotriazole

Employing the procedures described in Example 7, substituting isopropylamine for neopentylamine (Steps 1-4), the titled compound was obtained. LRMS m/z (M+H) 379.8 and 381.8 found, 379.9 and 381.9 required.

Step 2 Preparation of {4-[4-bromo-1-(2-methylpropyl)-1H-benzotriazol-5-yl]phenyl}methanol 4-Bromo-5-iodo-1-(2-methylpropyl)-1H-benzotriazole (554 mg, 1.458 mmol), 4-(hydroxymethyl)benzeneboronic acid pinacol ester (325 mg, 1.388 mmol), $PdCl_2$(dppf)-dichloromethane adduct (56.7 mg, 0.069 mmol) and cesium carbonate (1357 mg, 4.16 mmol) were combined in tetrahydrofuran (7 ml) and water (0.700 ml). The vessel was sealed and heated at 40° C. for 48 hours. The mixture was cooled to ambient temperature, diluted with ethyl acetate, filtered through Celite and concentrated in vacuo. The residue was purified via silica gel chromatography (ethyl acetate/hexane gradient), providing the titled compound as white foam. LRMS m/z (M+H) 359.9 and 361.9 found, 360.06 and 362.06 required.

Step 3 Preparation of 4-bromo-5-[4-(chloromethyl)phenyl]-1-(2-methylpropyl)-1H-benzotriazole To a solution of {4-[4-bromo-1-(2-methylpropyl)-1H-benzotriazol-5-yl]phenyl}methanol (234 mg, 0.650 mmol) in dichloromethane (5 ml) at 0° C. was treated with methanesulfonyl chloride (0.056 ml, 0.715 mmol), followed by the dropwise addition of triethylamine (0.181 ml, 1.299 mmol). After 2 hours, the mixture was purified via silica gel chromatography (acetone/dichloromethane gradient), providing the titled compound as white solid. LRMS m/z (M+H) 377.9 and 379.9 found, 378.03 and 380.03 required.

Step 4 Preparation of 1-{4-[4-bromo-1-(2-methylpropyl)-1H-benzotriazol-5-yl]benzyl}-3-methylimidazolidine-2,4-dione 4-Bromo-5-[4-(chloromethyl)phenyl]-1-(2-methylpropyl)-1H-benzotriazole (170 mg, 0.449 mmol), 3-methylimidazolidine-2,4-dione (102 mg, 0.898 mmol) and potassium carbonate (186 mg, 1.347 mmol) were combined in acetonitrile (3 ml) and heated at 50° C. for 16 hours. The mixture was cooled to ambient temperature, diluted with dichloromethane and filtered. The filtrate was washed with aqueous saturated ammonium chloride and brine. The organic extract was dried with sodium sulfate, filtered, and concentrated in vacuo. The residue was purified via silica gel chromatography (acetone/dichloromethane gradient), providing the titled compound as white solid: $^1$H NMR (500 MHz, $d^6$-DMSO): $^1$H NMR δ 8.00 (d, J=8.5 Hz, 1H), 7.55 (d, J=8.5 Hz, 1H), 7.48 (d, J=7.9 Hz, 2H), 7.42 (d, J=7.9 Hz, 2H), 4.60-4.57 (m, 4H), 3.97 (s, 2H), 2.90 (s, 3H), 2.34-2.27 (m, 1H), 0.93-0.88 (m, 6H) ppm. LRMS m/z (M+H) 455.9 and 457.9 found, 456.1 and 458.1 required.

Example 9

3-Methyl-1-{4-[1-(2-methylpropyl)-4-(trifluoromethyl)-1H-benzotriazol-5-yl]benzyl}imidazolidine-2,4-dione

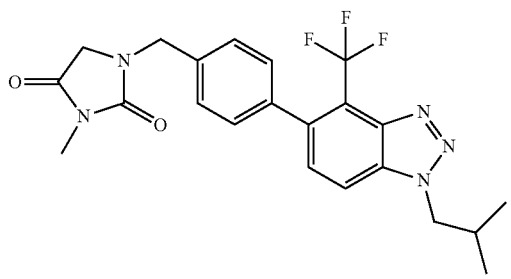 [SMILES: CC(C)Cn1nnc2c(C(F)(F)F)c(-c3ccc(CN4CC(=O)N(C)C4=O)cc3)ccc21]

1-{4-[4-Bromo-1-(2-methylpropyl)-1H-benzotriazol-5-yl]benzyl}-3-methylimidazolidine-2,4-dione (Example 8, 35 mg, 0.077 mmol), copper (I) iodide (29.2 mg, 0.153 mmol), and methyl 2,2-difluoro-2-(fluorosulfonyl)acetate (0.032 ml, 0.153 mmol) were combined in degassed DMF (1 ml) and placed in a preheated oil bath at 100° C. for 6 hours. The mixture was cooled to ambient temperature, diluted with ethyl acetate and treated with Celite. After stirring for 1 hour, the mixture was filtered through Celite. The filtrate was washed with aqueous saturated ammonium chloride and brine, dried with sodium sulfate, filtered and concentrated in vacuo. The residue was purified via preparative reverse phase HPLC (C-18), eluting with acetonitrile/water+0.1% TFA, to provide the titled compound: $^1$H NMR (500 MHz, d$^6$-DMSO) δ 8.28 (d, J=8.6 Hz, 2H), 7.78 (s, 1H), 7.71 (s, 1H), 7.52 (d, J=8.6 Hz, 2H), 4.65 (d, 2H), 4.60 (s, 2H), 3.95 (s, 2H), 2.90 (s, 3H), 2.32 (m 1H), 0.92 (m, 6H) ppm. LRMS m/z (M+H) 445.9 found, 446.1 required.

Example 10

1-{4-[4-Bromo-1-(cyclopropylmethyl)-1H-benzotriazol-5-yl]benzyl}-3-methylimidazolidine-2,4-dione

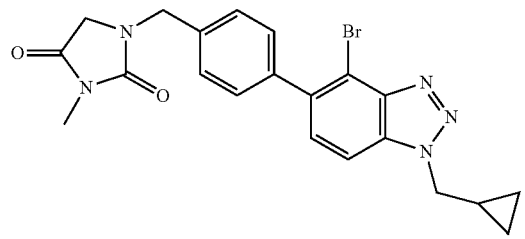 [SMILES: CN1C(=O)CN(Cc2ccc(-c3ccc4c(nnn4CC4CC4)c3Br)cc2)C1=O]

Step 1 Preparation of 4-bromo-5-iodo-1-(cyclopropylmethyl)-1H-benzotriazole

Employing the procedures described in Example 7, substituting cyclopropylamine for neopentylamine (Steps 1-4), the titled compound was obtained.

Step 2 Preparation of 1-{4-[4-bromo-1-(cyclopropylmethyl)-1H-benzotriazol-5-yl]benzyl}-3-methylimidazolidine-2,4-dione Employing the procedures described in Example 2, substituting 4-bromo-5-iodo-1-(cyclopropylmethyl)-1H-benzotriazole for 1-(cyclopropylmethyl)-4-(trifluoromethyl)-1H-benzotriazol-5-yltrifluoromethanesulfonate (Step 9), the titled compound was obtained: $^1$H NMR (400 MHz, CDCl$_3$) δ 7.56 (d, 1H, J=8.5 Hz), 7.43-7.50 (m, 3H), 7.37 (d, 2H, J=7.9 Hz), 4.66 (s, 2H), 4.56 (d, 2H, J=7.1 Hz), 3.83 (s, 2H), 3.08 (s, 3H), 1.40-1.46 (m, 1H), 0.69 (d, 2H, J=7.7 Hz), 0.52 (d, 2H, J=5.3 Hz) ppm. LRMS m/z (M+H, $^{81}$Br) 456.2 found, 456.1 required.

The following compounds were prepared according to the general procedures described in Example 8, substituting the appropriate amine for isopropylamine (Step 1), or substituting the appropriate boronic acid or ester for [4-(4,4,5,5-tetramethyl-1,3-dioxolan-2-yl)phenyl]methanol (Step 1, Example 2). The starting materials are either commercially available, known in the literature or may be prepared from commercially available reagents using conventional reactions well known in the art.

| Ex. | STRUCTURE | NAME | HRMS/LRMS |
|---|---|---|---|
| 11 | 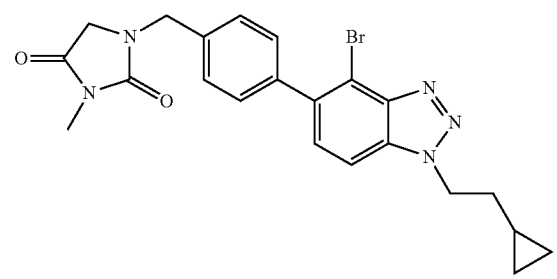 [SMILES: CN1C(=O)CN(Cc2ccc(-c3ccc4c(nnn4CCC4CC4)c3Br)cc2)C1=O] | 1-{4-[4-bromo-1-(2-cyclopropylethyl)-1H-benzotriazol-5-yl]benzyl}-3- | $C_{22}H_{23}BrN_5O_2$ [M + H] Calc'd 468.1, 470.1 Found 467.9, 469.9 |

| Ex. | STRUCTURE | NAME | HRMS/LRMS |
|---|---|---|---|
| 12 | 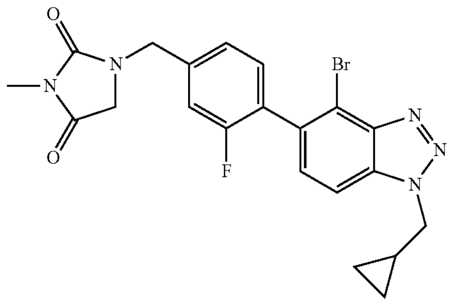 [SMILES: CN1C(=O)CN(Cc2ccc(-c3ccc4c(nnn4CC4CC4)c3Br)c(F)c2)C1=O] | 1-{4-[4-bromo-1-(cyclopropylmethyl)-1H-benzotriazol-5-yl]-3-fluorobenzyl}-3-methylimidazolidine-2,4-dione | $C_{21}H_{19}BrFN_5O_2$ [M + H, $^{81}$Br] Calc'd 474.1, found 474.1 |
| 13 | 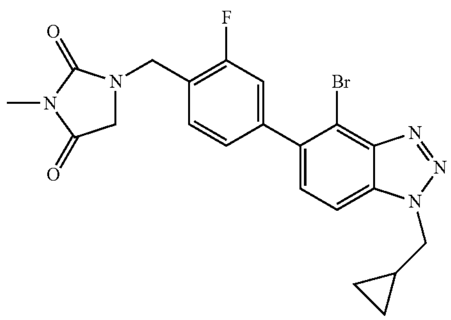 [SMILES: CN1C(=O)CN(Cc2ccc(-c3ccc4c(nnn4CC4CC4)c3Br)cc2F)C1=O] | 1-{4-[4-bromo-1-(cyclopropylmethyl)-1H-benzotriazol-5-yl]-2-fluorobenzyl}-3-methylimidazolidine-2,4-dione | $C_{21}H_{19}BrFN_5O_2$ [M + H, $^{81}$Br] Calc'd 474.1, found 474.1 |
| 14 | 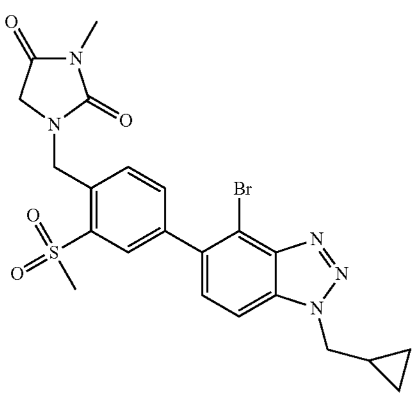 [SMILES: CN1C(=O)CN(Cc2ccc(-c3ccc4c(nnn4CC4CC4)c3Br)cc2S(C)(=O)=O)C1=O] | 1-{4-[4-bromo-1-(cyclopropylmethyl)-1H-benzotriazol-5-yl]-2-(methylsulfonyl)benzyl}-3-methylimidazolidine-2,4-dione | $C_{22}H_{22}BrN_5O_4S$ [M + H, $^{81}$Br] Calc'd 533.1, found 533.8 |

Example 15

1-{4-[1-(Cyclopropylmethyl)-4-(methylsulfanyl)-1H-benzotriazol-5-yl]-2-fluorobenzyl}-3-methylimidazolidine-2,4-dione

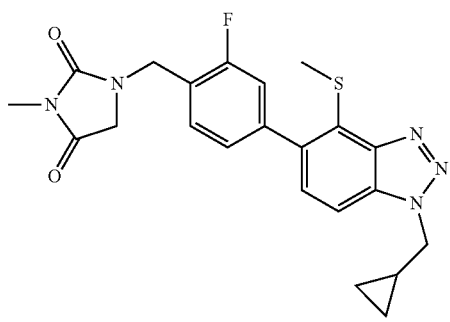 [SMILES: CSc1c(-c2ccc(CN3CC(=O)N(C)C3=O)c(F)c2)ccc2c1nnn2CC1CC1]

To a solution of 1-{4-[4-bromo-1-(cyclopropylmethyl)-1H-benzotriazol-5-yl]-2-fluorobenzyl}-3-methylimidazolidine-2,4-dione (10 mg, 0.021 mmol) in DMF (0.18 mL) was added sodium thiomethoxide (5.6 mg, 0.080 mmol, 4 equiv.). The mixture was stirred at 120° C. for 3.5 hours, cooled to ambient temperature and diluted with dichloromethane, which was washed with water and brine. The organic extract was dried with magnesium sulfate, filtered and concentrated in vacuo. The residue was purified via silica gel chromatography (ethyl acetate/hexane gradient), providing the titled compound: $^1$H NMR (400 MHz, CDCl$_3$) δ 7.39-7.45 (m, 2H), 7.34 (d, 1H, J=8.4 Hz), 7.18-7.24 (m, 2H), 4.70 (s, 2H), 4.53 (d, 2H, J=7.1 Hz), 3.90 (s, 2H), 3.06 (s, 3H), 2.85 (s, 3H), 1.40-1.46 (m, 1H), 0.67-0.71 (m, 2H), 0.50-0.54 (m, 2H) ppm. LRMS m/z (M+H) 440.2 found, 440.1 required.

Example 16

1-{4-[1-(Cyclopropylmethyl)-4-(methylsulfonyl)-1H-benzotriazol-5-yl]-2-fluorobenzyl}-3-methylimidazolidine-2,4-dione

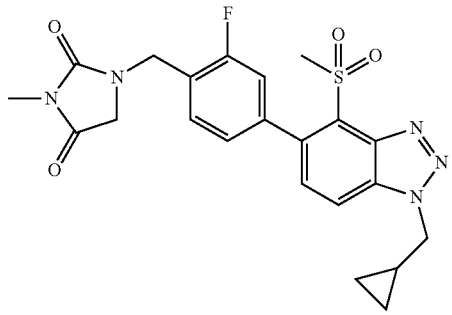 [SMILES: CN1C(=O)CN(Cc2ccc(-c3ccc4c(nnn4CC4CC4)c3S(C)(=O)=O)cc2F)C1=O]

To a solution of 1-{4-[1-(cyclopropylmethyl)-4-(methylsulfanyl)-1H-benzotriazol-5-yl]-2-fluorobenzyl}-3-methylimidazolidine-2,4-dione (Example 15, 14 mg, 0.032 mmol) in chloroform (0.45 mL) at 0° C. was added meta-peroxychlorobenzoic acid (7.1 mg, 0.032 mmol). The mixture was stirred for 1.5 hours at 0° C. and then warmed to ambient temperature and stirred for an additional 14 hours. The mixture was cooled to 0° C. and treated with calcium hydroxide (3.3 mg, 0.045 mmol), stirred for 30 minutes and filtered. The filtrate was concentrated in vacuo and purified via preparative reversed-phase HPLC (5-95% MeCN/water+0.1% TFA) to provide the title compound: $^1$H NMR (400 MHz, CDCl$_3$) δ 7.82 (d, 1H, J=8.0 Hz), 7.42 (d, 1H, J=8.8 Hz), 7.39 (t, 1H, J=7.6 Hz), 7.17-7.23 (m, 2H), 4.70 (s, 2H), 4.61 (d, 2H, J=7.2 Hz), 3.89 (s, 2H), 3.67 (s, 3H), 3.06 (s, 3H), 1.41-1.47 (m, 1H), 0.71-0.76 (m, 2H), 0.54-0.58 (m, 2H) ppm. LRMS m/z (M+H) 472.2 found, 472.1 required.

Example 17

1-{4-[1-(Cyclopropylmethyl)-4-(methylsulfinyl)-1H-benzotriazol-5-yl]-2-fluorobenzyl}-3-methylimidazolidine-2,4-dione

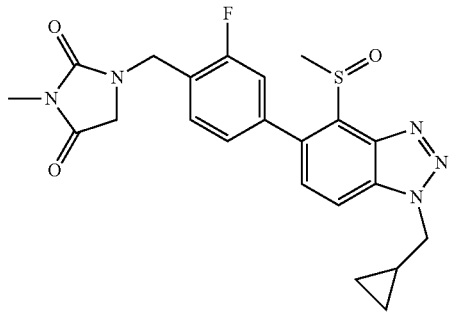 [SMILES: CN1C(=O)CN(Cc2ccc(-c3ccc4c(nnn4CC4CC4)c3S(C)=O)cc2F)C1=O]

Employing the procedures described in Example 16, the titled compound was obtained: $^1$H NMR (400 MHz, CDCl$_3$) δ 7.77 (d, 1H, J=8.8 Hz), 7.42-7.46 (m, 2H), 7.14-7.21 (m, 2H), 4.71 (s, 2H), 4.61 (d, 2H, J=7.2 Hz), 3.91 (s, 2H), 3.47 (s, 3H), 3.07 (s, 3H), 1.40-1.46 (m, 1H), 0.69-0.73 (m, 2H), 0.52-0.56 (m, 2H) ppm. LRMS m/z (M+H) 456.2 found, 456.1 required.

Example 18

1-(Cyclopropylmethyl)-5-{4-[(3-methyl-2,4-dioxoimidazolidin-1-yl)methyl]phenyl}-1H-benzotriazole-4-carbonitrile

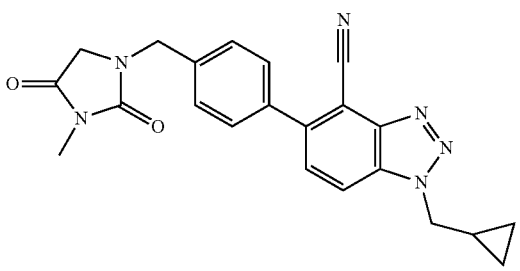 [SMILES: CN1C(=O)CN(Cc2ccc(-c3ccc4c(nnn4CC4CC4)c3C#N)cc2)C1=O]

To a solution of 1-{4-[4-bromo-1-(cyclopropylmethyl)-1H-benzotriazol-5-yl]benzyl}-3-methylimidazolidine-2,4-dione (Example 10, 34 mg, 0.075 mmol) in dioxane (0.75 mL) zinc dust (2.5 mg, 0.037 mmol, 0.5 equiv.) and zinc cyanide (12.6 mg, 0.107 mmol, 1.4 equiv.) were added. The mixture was purged subsurface with nitrogen, then bis(triphenylphosphine)palladium (II) dichloride (10.5 mg, 0.015 mmol) was added and the mixture was irradiated at 180° C. for 1 hour. The mixture was cooled to ambient temperature, diluted with ethyl acetate and washed with saturated aqueous sodium bicarbonate and brine. The organic extract was dried with magnesium sulfate, filtered and concentrated in vacuo. The residue was purified via silica gel chromatography (ethyl acetate/hexane gradient), providing the titled compound: $^1$H NMR (400 MHz, CDCl$_3$) δ 7.87 (d, 1H, J=8.7 Hz), 7.63-7.67 (m, 3H), 7.43 (d, 2H, J=8.4 Hz), 4.67 (s, 2H), 4.60 (d, 2H, J=7.2 Hz), 3.84 (s, 2H), 3.09 (s, 3H), 1.40-1.47 (m, 1H), 0.68-0.75 (m, 2H), 0.52-0.56 (m, 2H) ppm. LRMS m/z (M+H) 401.2 found, 401.2 required.

Example 19

1-{4-[1-(Cyclopropylmethyl)-4-ethyl-1H-benzotriazol-5-yl]benzyl}-3-methylimidazolidine-2,4-dione

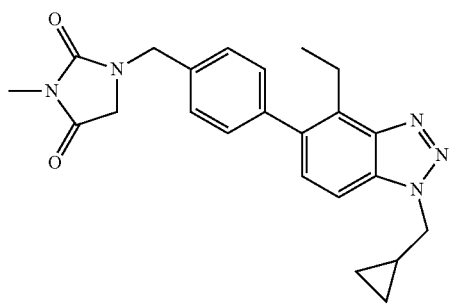 [SMILES: CCc1c(-c2ccc(CN3CC(=O)N(C)C3=O)cc2)ccc2c1nnn2CC1CC1]

Step 1 Preparation of 1-{4-[1-(cyclopropylmethyl)-4-ethenyl-M-benzotriazol-5-yl]benzyl}-3-methylimidazolidine-2,4-dione To a solution of 1-{4-[4-bromo-1-(cyclopropylmethyl)-1H-benzotriazol-5-yl]benzyl}-3-methylimidazolidine-2,4-dione (Example 10, 200 mg, 0.440 mmol) in DMF (2.2 mL) was added lithium chloride (56 mg, 1.32 mmol, 3 equiv.), tributyl(vinyl)tin (193 µL, 0.660 mmol, 1.5 equiv.), and bis(triphenylphosphine)palladium (II) dichloride (31 mg, 0.044 mmol, 0.1 equiv.). The mixture was purged subsurface with nitrogen and heated at 105° C. for 14 hours. The mixture was cooled to ambient temperature, diluted with ethyl acetate and filtered through a silica plug, providing the titled compound.

Step 2 Preparation of 1-{4-[1-(cyclopropylmethyl)-4-ethyl-1H-benzotriazol-5-yl]benzyl}-3-methylimidazolidine-2,4-dione To a solution of 1-{4-[1-(cyclopropylmethyl)-4-ethenyl-1H-benzotriazol-5-yl]benzyl}-3-methylimidazolidine-2,4-dione (68 mg, 0.17 mmol) in EtOH (1.7 mL) was added palladium on carbon (10 wt %, 9 mg). The mixture was sparged under an atmosphere of hydrogen (1 atm) and stirred for 18 hours. The mixture was filtered through Celite and washed with ethanol. The filtrate was concentrated in vacuo and purified via reverse phase HPLC (5-95% MeCN/water+ 0.1% TFA) to provide the title compound: $^1$H NMR (400 MHz, CDCl$_3$) δ 7.31-7.43 (m, 6H), 4.65 (s, 2H), 4.53 (d, 2H, J=6.8 Hz), 3.83 (s, 2H), 3.13 (q, 2H, J=7.6 Hz), 3.09 (s, 3H), 1.40-1.48 (m, 1H), 1.26 (t, 3H, J=7.2 Hz), 0.66-0.71 (m, 2H), 0.50-0.54 (m, 2H) ppm. LRMS m/z (M+H) 404.3 found, 404.2 required.

Example 20

1-(Cyclopropylmethyl)-5-{4-[(3-methyl-2,4-dioxoimidazolidin-1-yl)methyl]phenyl}-1H-benzotriazole-4-carbaldehyde

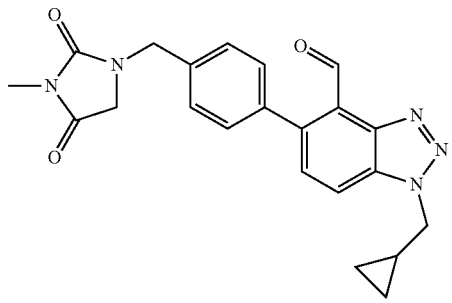 [SMILES: CN1C(=O)CN(Cc2ccc(-c3ccc4c(nnn4CC4CC4)c3C=O)cc2)C1=O]

A solution of 1-{4-[1-(cyclopropylmethyl)-4-ethenyl-1H-benzotriazol-5-yl]benzyl}-3-methylimidazolidine-2,4-dione [(Example 19, Step 1), 328 mg, 0.817 mmol] in methanol (8.2 mL) and dichloromethane (24.5 mL) was cooled to −78° C. Ozone was bubbled through the mixture until saturated and then removed. Oxygen was bubbled through the solution for 15 minutes and then treated with polymer-bound triphenylphosphine (0.27 g, 3 mmol/g). The mixture was warmed to ambient temperature and stirred for 14 hours. The mixture was filtered and the solid was washed with methanol. The filtrate was concentrated in vacuo and purified via silica gel chromatography (ethyl acetate/hexane gradient), providing the titled compound: $^1$H NMR (400 MHz, CDCl$_3$) δ 10.39 (s, 1H), 7.86 (d, 1H, J=8.4 Hz), 7.55 (d, 1H, J=8.8 Hz), 7.45 (d, 2H, J=8.2 Hz), 7.39 (d, 2H, J=8.2 Hz), 4.67 (s, 2H), 4.62 (d, 2H, J=6.8 Hz), 3.83 (s, 2H), 3.09 (s, 3H), 1.40-1.46 (m, 1H), 0.67-0.72 (m, 2H), 0.51-0.55 (m, 2H) ppm. LRMS m/z (M+H) 404.2 found, 404.2 required.

Example 21

1-{4-[1-(Cyclopropylmethyl)-4-(hydroxymethyl)-1H-benzotriazol-5-yl]benzyl}-3-methylimidazolidine-2,4-dione

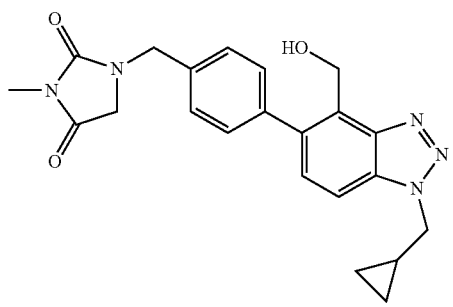 [SMILES: CN1C(=O)CN(Cc2ccc(-c3ccc4c(nnn4CC4CC4)c3CO)cc2)C1=O]

To a solution of 1-(cyclopropylmethyl)-5-{4-[(3-methyl-2,4-dioxoimidazolidin-1-yl)methyl]phenyl}-1H-benzotriazole-4-carbaldehyde (Example 20, 72 mg, 0.18 mmol) in methanol (1.8 mL) was added sodium borohydride (6.8 mg, 0.18 mmol). After 1.5 hours, the mixture was treated with water, diluted with dichloromethane and washed with brine. The organic extract was dried with magnesium sulfate, filtered and concentrated in vacuo. The residue was purified via silica gel chromatography (ethyl acetate/hexane gradient), providing the titled compound: $^1$H NMR (400 MHz, CDCl$_3$) δ 7.54 (d, 1H, J=8.8 Hz), 7.42-7.45 (m, 3H), 7.35 (d, 2H, J=8.0 Hz), 5.12 (d, 2H, J=6.4 Hz), 4.65 (s, 2H), 4.55 (d, 2H, J=7.2 Hz), 3.83 (s, 2H), 3.08 (s, 3H), 1.40-1.47 (m, 1H), 0.67-0.71 (m, 2H), 0.51-0.55 (m, 2H) ppm. LRMS m/z (M+H) 406.0 found, 406.2 required.

Example 22

1-{4-[1-(Cyclopropylmethyl)-4-(fluoromethyl)-1H-benzotriazol-5-yl]benzyl}-3-methylimidazolidine-2,4-dione

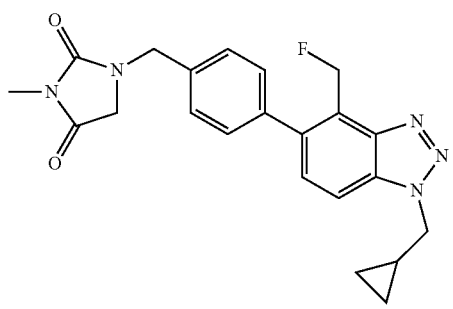 [SMILES: CN1C(=O)CN(Cc2ccc(-c3ccc4c(nnn4CC4CC4)c3CF)cc2)C1=O]

A solution of 1-{4-[1-(cyclopropylmethyl)-4-(hydroxymethyl)-1H-benzotriazol-5-yl]benzyl}-3-methylimidazolidine-2,4-dione (Example 21, 24 mg, 0.059 mmol) in dichloromethane (0.85 mL) was cooled at 0° C. and treated with Deoxofluor (14.2 µL, 0.077 mmol, 1.3 equiv). After stirring for 1 hour at 0° C., the mixture was treated with aqueous saturated ammonium chloride, diluted with dichloromethane and washed with brine. The organic extract was dried with magnesium sulfate, filtered and concentrated in vacuo. The residue was purified via reverse phase HPLC (5-95% MeCN/water+0.1% TFA), providing the titled compound: $^1$H NMR (400 MHz, CDCl$_3$) δ 7.66 (dd, 1H, J=8.4, 2.4 Hz), 7.49-7.53 (m, 3H), 7.37 (d, 2H, J=8.0 Hz), 5.84 (d, 2H, J=48.0 Hz), 4.66 (s, 2H), 4.57 (d, 2H, J=6.8 Hz), 3.83 (s, 2H), 3.09 (s, 3H), 1.40-1.48 (m, 1H), 0.66-0.71 (m, 2H), 0.51-0.55 (m, 2H) ppm. LRMS m/z (M+H) 408.0 found, 408.2 required.

The following compounds were prepared according to the general procedures described in Examples 18 and 19. The starting materials are either commercially available, known in the literature or may be prepared from commercially available reagents using conventional reactions well known in the art.

| Ex. | STRUCTURE | NAME | HRMS/LRMS |
|---|---|---|---|
| 23 | 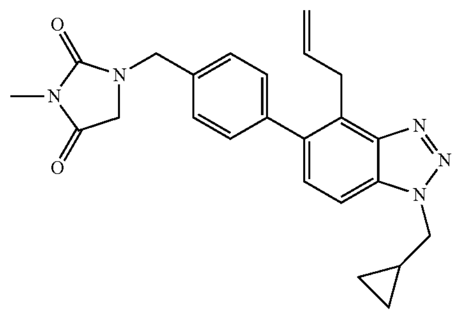 [SMILES: C=CCc1c(-c2ccc(CN3CC(=O)N(C)C3=O)cc2)ccc2c1nnn2CC1CC1] | 1-{4-[1-(cyclopropylmethyl)-4-prop-2-en-1-yl-1H-benzotriazol-5-yl]benzyl}-3-methylimidazolidine-2,4-dione | $C_{24}H_{25}N_5O_2$ [M + H] Calc'd 416.2, found 416.0 |
| 24 | 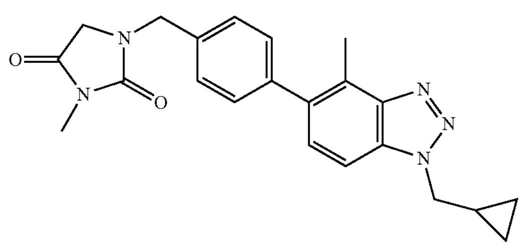 [SMILES: Cc1c(-c2ccc(CN3CC(=O)N(C)C3=O)cc2)ccc2c1nnn2CC1CC1] | 1-{4-[1-(cyclopropylmethyl)-4-methyl-1H-benzotriazol-5-yl]benzyl}-3-methylimidazolidine-2,4-dione | $C_{22}H_{23}N_5O_2$ [M + H] Calc'd 390.2, found 390.2 |
| 25 | 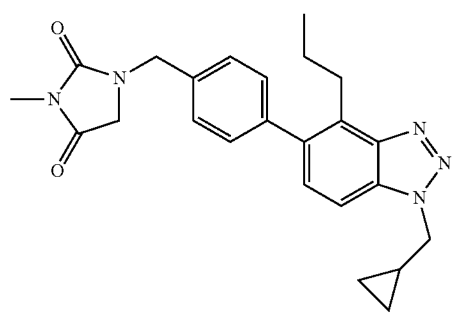 [SMILES: CCCc1c(-c2ccc(CN3CC(=O)N(C)C3=O)cc2)ccc2c1nnn2CC1CC1] | 1-{4-[1-(cyclopropylmethyl)-4-propyl-1H-benzotriazol-5-yl]benzyl}-3-methylimidazolidine-2,4-dione | $C_{24}H_{27}N_5O_2$ [M + H] Calc'd 418.2, Found 418.1 |
| 26 | 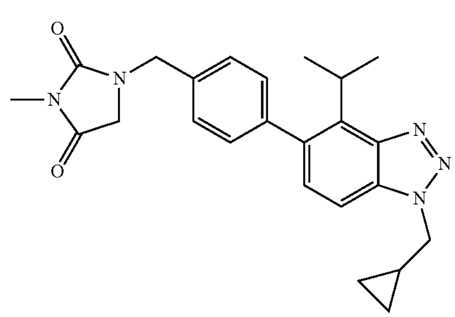 [SMILES: CC(C)c1c(-c2ccc(CN3CC(=O)N(C)C3=O)cc2)ccc2c1nnn2CC1CC1] | 1-{4-[1-(cyclopropylmethyl)-4-(1-methylethyl)-1H-benzotriazol-5-yl]benzyl}-3-methylimidazolidine-2,4-dione | $C_{24}H_{27}N_5O_2$ [M + H] Calc'd 418.2, Found 418.1 |

-continued

| Ex. | STRUCTURE | NAME | HRMS/LRMS |
|---|---|---|---|
| 27 | 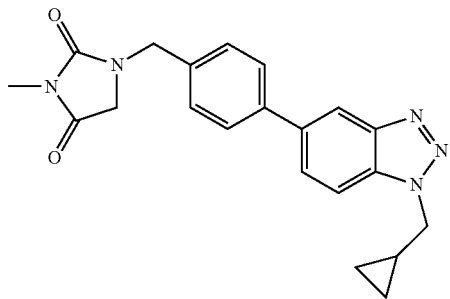 | 1-{4-[1-(cyclopropylmethyl)-4-(difluoromethyl)-1H-benzotriazol-5-yl]benzyl}-3-methylimidazolidine-2,4-dione | $C_{22}H_{21}F_2N_5O_2$ [M + H] Calc'd 426.2, found 426.0 |

Example 28

1-{4-[1-(Cyclopropylmethyl)-1H-benzotriazol-5-yl]benzyl}-3-methylimidazolidine-2,4-dione

Example 29

1-{4-[4-Chloro-1-(cyclopropylmethyl)-1H-benzotriazol-5-yl]benzyl}-3-methylimidazolidine-2,4-dione

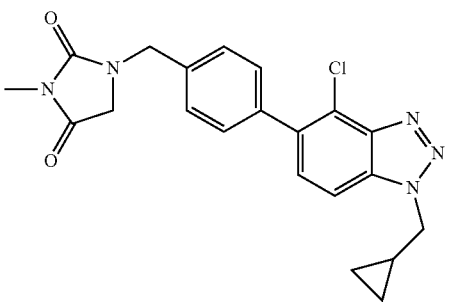

1-{4-[4-Bromo-1-(cyclopropylmethyl)-1H-benzotriazol-5-yl]benzyl}-3-methylimidazolidine-2,4-dione (Example 10, 20 mg, 0.044 mmol) was dissolved in methanol (7 mL) and sparged under nitrogen. The vessel was charged with Pd/C (4.7 mg, 1 equiv), sparged under an atmosphere of hydrogen (1 atm) and vigorously stirred for 2 hours. The mixture was sparged under and atmosphere of nitrogen, filtered through a pad of Celite and the pad was washed with methanol (20 mL). The mixture was concentrated in vacuo and the residue was purified by preparative reverse phase HPLC (95:5 to 5:95; water containing 0.1% trifluoroacetic acid:acetonitrile containing 0.1% trifluoroacetic acid), providing the titled compound: $^1$H-NMR (400 MHz, d$^6$-DMSO) δ 8.29 (1H, s), 8.02 (1H, d, J=9.2 Hz), 7.78 (1H, dd, J=8.7, 1.4 Hz), 7.78 (2H, d, J=8.3 Hz), 7.42 (2H, d, J=8.1 Hz), 4.64 (2H, d, J=7.3 Hz), 4.56 (2H, s), 3.93 (2H, s), 2.90 (3H, s), 1.43-1.35 (1H, m), 0.59-0.55 (2H, m), 0.51-0.48 (2H, m) ppm; high resolution mass spectrometry (ES+) m/z 376.1763 [(M+H)$^+$; calculated for $C_{21}H_{22}N_5O_2$: 376.1768].

Preparation of Example 29:

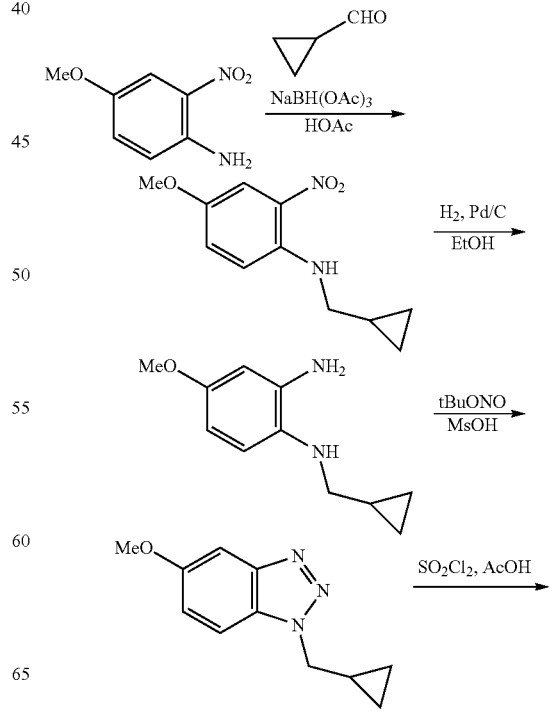

-continued

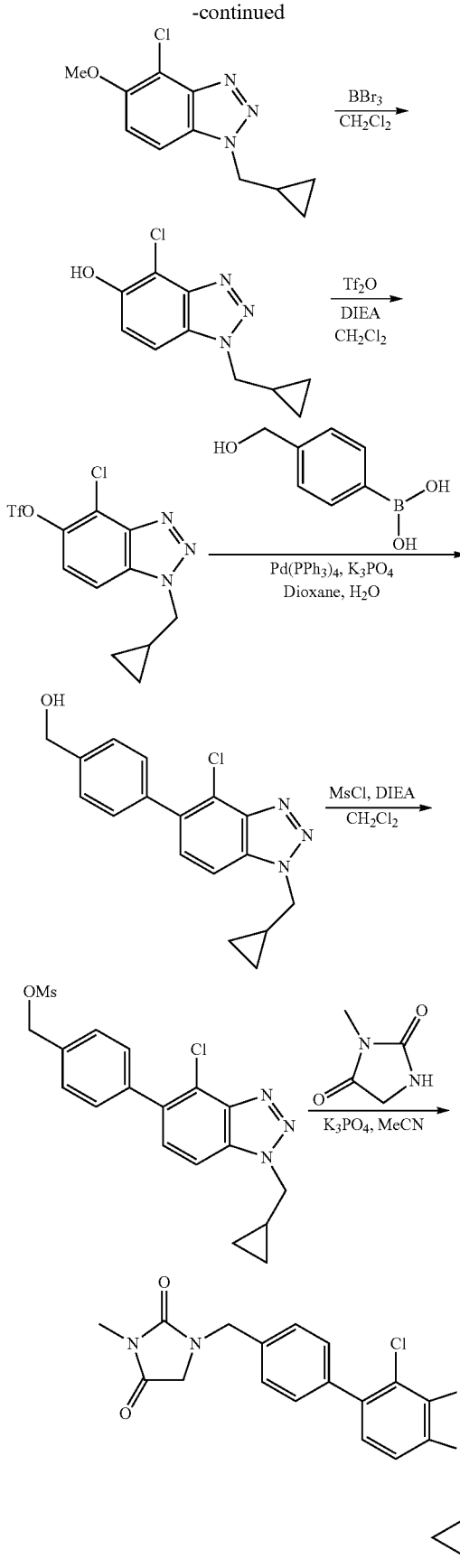

Step 1 Preparation of N-(cyclopropylmethyl)-4-methoxy-2-nitroaniline

A 5 L vessel was charged 4-methoxy-2-nitroaniline (160 g, 952 mmol) in dichloromethane (2.44 L) was cooled to 10° C. Cyclopropanecarboxyaldehyde (100 g, 143 mmol) was added in four 25 gram portions followed by acetic acid (300 ml, 523 mmol), which was added via addition funnel over 20 minutes. After 45 minutes, the vessel was charged with sodium triacetoxyborohydride (444 g, 209 mmol) portionwise. The mixture was warmed to ambient temperature over 4 hours and stirred for an additional 14 hours. The mixture was treated with saturated aqueous sodium bicarbonate (100 mL) and poured into sodium bicarbonate (4 L) and dichloromethane. The organic extract was concentrated in vacuo, providing the titled compound.

Step 2 Preparation of $N^1$-cyclopropylmethyl)-4-methoxybenzene-1,2-diamine

N-(Cyclopropylmethyl)-4-methoxy-2-nitroaniline (175 g) was dissolved in ethanol (1750 mL) and was added to a 4.0 L Hast 'C' Shaker can. The mixture was cooled to 10° C. and treated with 3% Pt/0.6% VG/C, deGussa (4.5 g). The vessel was sparged under nitrogen and then sparged three times with hydrogen at a setting of 40 psi and agitated for 2.5 hours. To a pre-washed solka-flok with ethanol, the mixture was filtered through solka-flok through a sintered glass funnel. The solka-flok was then washed with 1 L ethanol and concentrated in vacuo, providing the titled compound.

Step 3 Preparation of 1-(cyclopropylmethyl)-5-methoxy-1H-benzotriazole $N^1$-(Cyclopropylmethyl)-4-methoxybenzene-1,2-diamine (10.8 g, 56.2 mmol) was dissolved in ethanol (80 mL) and treated with methanesulfonic acid (3.65 ml, 56.2 mmol) followed by isoamyl nitrite (7.56 ml, 56.2 mmol). The mixture was stirred for 15 minutes, diluted with ethyl acetate (1500 mL) and washed with saturated bicarbonate solution (500 mL×2). The organic extracts were concentrated in vacuo. The residue was purified by silica gel gradient chromatography (5-50% ethyl acetate in heptanes), providing the titled compound as a tan solid.

Step 4 Preparation of 4-chloro-1-(cyclopropylmethyl)-5-methoxy-1H-benzotriazole 1-(Cyclopropylmethyl)-5-methoxy-1H-benzotriazole (10 g, 49 mmol) was dissolved in acetic acid (100 mL), cooled to 0° C. and treated with sulfuryl dichloride (4.8 mL, 59 mmol, 1.2 equiv) over three minutes. The mixture was warmed to ambient temperature over three hours and stirred for an additional 14 hours. The mixture was diluted with ethyl acetate and washed with aqueous saturated sodium bicarbonate. The organic layer was dried with magnesium sulfate, filtered and partially concentrated in vacuo to ~30 mL, which was then treated with water. The resulting precipitate was filtered, collected and dried in vacuo, providing the titled compound.

Step 5 Preparation of 4-chloro-1-(cyclopropylmethyl)-1H-benzotriazol-5-ol

4-Chloro-1-(cyclopropylmethyl)-5-methoxy-1H-benzotriazole (10.5 g, 44.2 mmol) was dissolved in dichloromethane (200 mL), cooled to 0° C. and treated with boron tribromide (88 mL, 1 M dichloromethane solution, 88 mmol, 2 equiv).

The ice bath was removed and the mixture was stirred for 4 hours at ambient temperature. The mixture was treated with water (10 mL) and then treated with sodium hydroxide (1 N aqueous) until pH>10. After stirring for an additional 30 minutes, ammonium chloride (aqueous saturated) was added until the pH of the mixture was adjusted to pH 6-7. The aqueous mixture was extracted exhaustively with dichloromethane containing 5% methanol and the combined organic extracts were dried with sodium sulfate, filtered and concentrated in vacuo, providing the titled compound as a light brown solid.

Step 6 Preparation of 4-chloro-1-(cyclopropylmethyl)-1H-benzotriazol-5-yl trifluoromethanesulfonate 4-Chloro-1-(cyclopropylmethyl)-1H-benzotriazol-5-ol (2.91 g, 13.0 mmol) was suspended in dichloromethane (40 mL), cooled to 0° C. and treated with N,N-diisopropylethylamine (4.55 mL, 26.0 mmol, 2 equiv). The mixture was treated with trifluoromethanesulfonic anhydride (2.86 mL, 16.9 mmol, 1.3 equiv) and stirred for 30 minutes. The mixture was poured into ammonium chloride (100 mL, aqueous saturated) and extracted with dichloromethane (2×150 mL). The combined organic extracts were dried with sodium sulfate, filtered and concentrated in vacuo. The residue was purified by silica gel gradient chromatography (100:0 to 1:1; hexanes: ethyl acetate), providing the titled compound as a light brown solid.

Step 7 Preparation of {4-[4-chloro-1-(cyclopropylmethyl)-1H-benzotriazol-5-yl]phenyl}methanol 4-Chloro-1-(cyclopropylmethyl)-1H-benzotriazol-5-yl trifluoromethanesulfonate (1.1 g, 3.1 mmol) was dissolved in a mixture of 1,4-dioxane and water (15 mL:3.0 mL) and treated with [4-(hydroxymethyl)phenyl]boronic acid (0.70 g, 4.6 mmol), potassium phosphate (2.0 g, 9.2 mmol) and palladium(0) tetrakis(triphenylphosphine) (0.18 g, 0.15 mmol). The mixture was placed into a preheated oil bath at 90° C. for 1 hour. The mixture was cooled to ambient temperature, poured into sodium bicarbonate (150 mL, aqueous saturated) and extracted with ethyl acetate (2×250 mL). The combined organic extracts were dried with sodium sulfate, filtered and concentrated in vacuo. The residue was purified by silica gel chromatography (100:0 to 0:100; hexane:ethyl acetate) to afford the titled compound.

Step 8 Preparation of 4-[4-chloro-1-(cyclopropylmethyl)-1H-benzotriazol-5-yl]benzyl methanesulfonate {4-[4-Chloro-1-(cyclopropylmethyl)-1H-benzotriazol-5-yl]phenyl}methanol (0.71, 2.3 mmol) was dissolved in dichloromethane (7 mL) and treated with N,N-diisopropylethylamine (0.79 mL, 4.5 mmol). The mixture was cooled to 0° C. and treated with methanesulfonyl chloride (0.21 mL, 2.7 mmol) and after 1 hour, the mixture was treated with additional methanesulfonyl chloride (50 uL). After stirring for an additional 30 minutes, the mixture was poured into ammonium chloride (50 mL, aqueous saturated) and extracted with dichloromethane (2×100 mL). The combined organic extracts were dried with sodium sulfate, filtered and concentrated in vacuo, providing the titled compound.

Step 9 Preparation of 1-{4-[1-(cyclopropylmethyl)-1H-benzotriazol-5-yl]benzyl}-3-methylimidazolidine-2,4-dione Employing the procedures described in Example 2, substituting 4-chloro-1-(cyclopropylmethyl)-1H-benzotriazol-5-yl trifluoromethanesulfonate for 1-(cyclopropylmethyl)-4-(trifluoromethyl)-1H-benzotriazol-5-yltrifluoromethanesulfonate, the titled compound was obtained: $^1$H-NMR (400 MHz, CDCl$_3$) δ 7.53 (1H, d J=8.6 Hz), 7.52 (2H, d, J=8.2 Hz), 7.47 (1H, d, J=8.7 Hz), 7.38 (2H, d, J=8.2 Hz), 4.65 (2H, s), 4.56 (2H, d, J=7.2 Hz), 3.83 (2H, s), 3.08 (3H, s), 1.48-1.38 (1H, m), 0.72-0.67 (2H, m), 0.54-0.50 (2H, m) ppm; high resolution mass spectrometry (ES+) m/z 410.1373 [(M+H)$^+$; calculated for C$_{21}$H$_{21}$ClN$_5$O$_2$: 410.1378].

The following compounds were prepared according to the general procedures described in Examples 1, 2, and 29. The starting materials are either commercially available, known in the literature or may be prepared from commercially available reagents using conventional reactions well known in the art.

| Ex. | STRUCTURE | NAME | HRMS/LRMS |
|---|---|---|---|
| 30 | 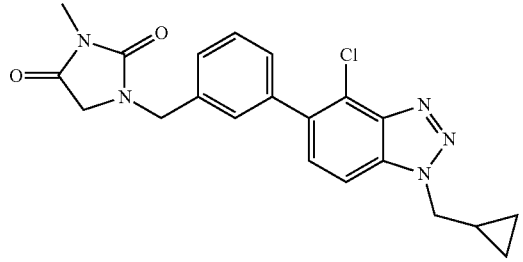 [SMILES: CN1C(=O)CN(Cc2cccc(-c3ccc4c(nnn4CC4CC4)c3Cl)c2)C1=O] | 1-{3-[4-chloro-1-(cyclopropylmethyl)-1H-benzotriazol-5-yl]benzyl}-3-methylimidazolidine-2,4-dione | C$_{21}$H$_{21}$ClN$_5$O$_2$ [M + H] Calc'd 410.1376 found 410.1376 |

| Ex. | STRUCTURE | NAME | HRMS/LRMS |
|---|---|---|---|
| 31 | 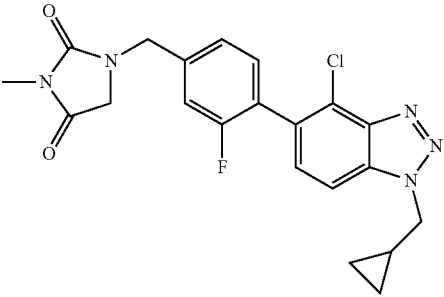 [SMILES: CN1C(=O)CN(Cc2ccc(-c3ccc4c(nnn4CC4CC4)c3Cl)c(F)c2)C1=O] | 1-{4-[4-chloro-1-(cyclopropylmethyl)-1H-benzotriazol-5-yl]-3-fluorobenzyl}-3-methylimidazolidine-2,4-dione | $C_{21}H_{20}ClFN_5O_2$ [M + H] Calc'd 428.1284 found 428.1295 |
| 32 | 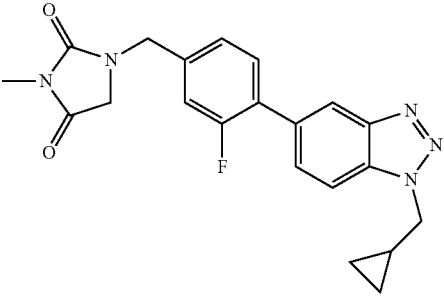 [SMILES: CN1C(=O)CN(Cc2ccc(-c3ccc4c(c3)nnn4CC3CC3)c(F)c2)C1=O] | 1-{4-[1-(cyclopropylmethyl)-1H-benzotriazol-5-yl]-3-fluorobenzyl}-3-methylimidazolidine-2,4-dione | $C_{21}H_{21}FN_5O_2$ [M + H] Calc'd 394.1674 found 394.1674 |
| 33 | 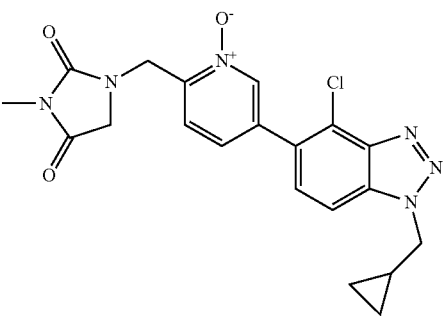 [SMILES: CN1C(=O)CN(Cc2ccc(-c3ccc4c(nnn4CC4CC4)c3Cl)c[n+]2[O-])C1=O] | 1-({5-[4-chloro-1-(cyclopropylmethyl)-1H-benzotriazol-5-yl]-1-oxidopyridin-2-yl}methyl)-3-methylimidazolidine-2,4-dione | $C_{20}H_{21}ClN_6O_3$ [M + H] Calc'd 427.1283, found 427.1287 |
| 34 | 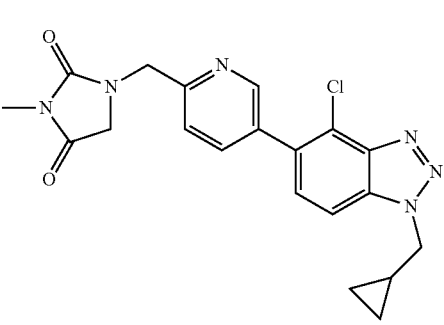 [SMILES: CN1C(=O)CN(Cc2ccc(-c3ccc4c(nnn4CC4CC4)c3Cl)cn2)C1=O] | 1-({5-[4-chloro-1-(cyclopropylmethyl)-1H-benzotriazol-5-yl]pyridin-2-yl}methyl)-3-methylimidazolidine-2,4-dione | $C_{20}H_{20}ClN_6O_2$ [M + H] Calc'd 411.1333, found 411.1349 |
| 35 | 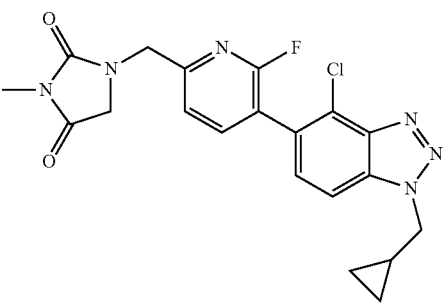 [SMILES: CN1C(=O)CN(Cc2ccc(-c3ccc4c(nnn4CC4CC4)c3Cl)c(F)n2)C1=O] | 1-({5-[4-chloro-1-(cyclopropylmethyl)-1H-benzotriazol-5-yl]-6-fluoropyridin-2-yl}methyl)-3-methylimidazolidine-2,4-dione | $C_{20}H_{19}ClFN_6O_2$ [M + H] Calc'd 429.1239, found 429.1249 |

| Ex. | STRUCTURE | NAME | HRMS/LRMS |
|---|---|---|---|
| 36 | 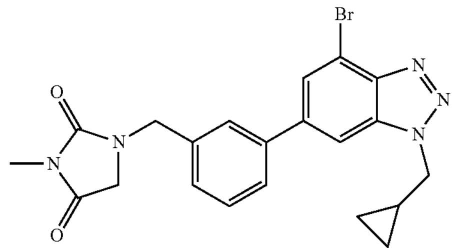 [SMILES: CN1C(=O)CN(Cc2cccc(-c3cc(Br)c4nnn(CC5CC5)c4c3)c2)C1=O] | 1-{3-[4-bromo-1-(cyclopropylmethyl)-1H-benzotriazol-6-yl]benzyl}-3-methylimidazolidine-2,4-dione | $C_{21}H_{19}BrN_5O_2$ [M + H] Calc'd 456.3 found 456.0 |

Example 37

5-[4-(Azidomethyl)phenyl]-4-chloro-1-(cyclopropylmethyl)-1H-benzotriazole

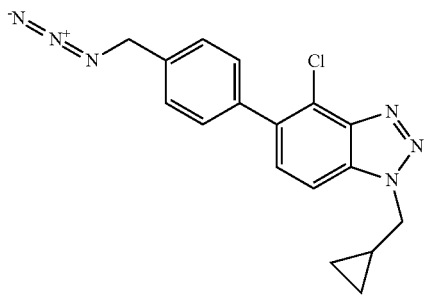

Employing the procedures described in Example 5, substituting 4-[1-(cyclopropylmethyl)-4-chloro-1H-benzotriazole-5-yl]benzyl methanesulfonate (Example 29) for 4-[1-(cyclopropylmethyl)-4-(trifluoromethyl)-1H-benzotriazole-5-yl] benzyl methanesulfonate (Step 1), the titled compound was obtained: $^1$H-NMR (400 MHz, d$^6$-DMSO) δ 8.02 (1H, d, J=8.6 Hz), 7.61 (1H, d, J=8.4 Hz), 7.57 (2H, d, J=8.0 Hz), 7.52 (2H, d, J=8.0 Hz), 4.68 (2H, d, J=7.2 Hz), 4.56 (2H, s), 1.45-1.37 (1H, m), 0.60-0.56 (2H, m), 0.52-0.49 (2H, m) ppm; high resolution mass spectrometry (ES+) m/z 339.1117 [(M+H)$^+$; calculated for $C_{17}H_{16}ClN_6$: 339.1119].

Example 38

1-{4-[4-Chloro-1-(cyclopropylmethyl)-1H-benzotriazol-5-yl]phenyl}methanamine

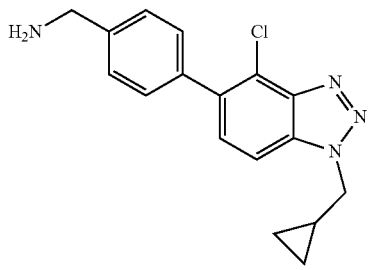 [SMILES: NCc1ccc(-c2ccc3c(nnn3CC3CC3)c2Cl)cc1]

Employing the procedures described in Example 5, substituting 5-[4-(azidomethyl)phenyl]-1-(cyclopropylmethyl)-4-chloro-1H-benzotriazole (Example 37) for 5-[4-(azidomethyl)phenyl]-1-(cyclopropylmethyl)-4-(trifluoromethyl)-1H-benzotriazole (Step 2), the titled compound was obtained: $^1$H-NMR (400 MHz, d$^6$-DMSO) δ 8.00 (1H, d, J=8.8 Hz), 7.57 (1H, d, J=8.8 Hz), 7.48-7.44 (2H, m), 7.27 (1H, br s), 6.67 (1H, br s), 4.67 (2H, d, J=7.2 Hz), 3.80 (2H, s), 1.44-1.36 (1H, m), 0.59-0.56 (2H, m), 0.51-0.48 (2H, m) ppm; high resolution mass spectrometry (ES+) m/z 313.1217 [(M+H)$^+$; calculated for $C_{17}H_{18}ClN_4$: 313.1215].

Example 39

(2R)—N-{4-[4-chloro-1-(cyclopropylmethyl)-1H-benzotriazol-5-yl]benzyl}-2-hydroxypropanamide

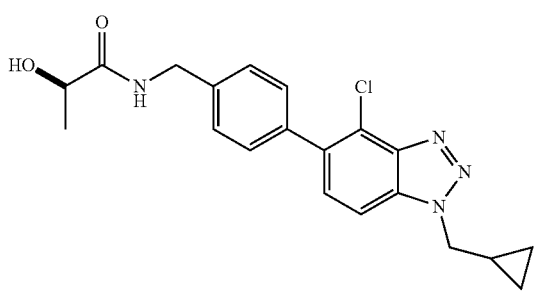

Employing the procedures described in Example 5, substituting 1-{4-[1-(cyclopropylmethyl)-4-chloro-1H-benzotriazol-5-yl]phenyl}methanamine (Example 38) for 1-{4-[1-(cyclopropylmethyl)-4-(trifluoromethyl)-1H-benzotriazol-5-yl]phenyl}methanamine (Step 3), the titled compound was obtained: $^1$H-NMR (400 MHz, d$^6$-DMSO) δ 8.32 (1H, t, J=6.3 Hz), 8.00 (1H, d, J=8.6 Hz), 7.57 (1H, d, J=8.9 Hz), 7.47 (2H, d, J=8.2 Hz), 7.39 (2H, d, J=8.2 Hz), 4.67 (2H, d, J=7.5 Hz), 4.41-4.33 (2H, m), 4.05 (qd, J=6.7, 4.7 Hz), 1.44-1.36 (1H, m), 1.27 (3H, d, J=6.9 Hz), 0.59-0.56 (2H, m), 0.51-0.48 (2H, m) ppm; high resolution mass spectrometry (ES+) m/z 385.1432 [(M+H)$^+$; calculated for $C_{20}H_{22}ClN_4O_2$: 385.1426].

The following compounds were prepared according to the general procedure described in Example 39, substituting the appropriate acid for L-lactic acid. The starting materials are either commercially available, known in the literature or may be prepared from commercially available reagents using conventional reactions well known in the art.

| Ex. | STRUCTURE | NAME | HRMS/LRMS |
|---|---|---|---|
| 40 | 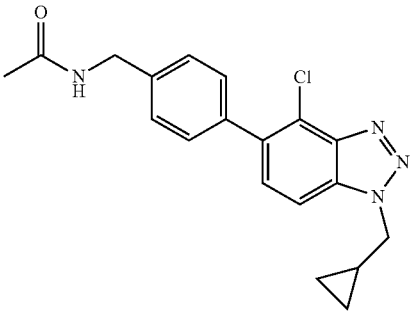 [SMILES: CC(=O)NCc1ccc(-c2ccc3c(nnn3CC3CC3)c2Cl)cc1] | N-{4-[4-chloro-1-(cyclopropylmethyl)-1H-benzotriazol-5-yl]benzyl}acetamide | C₁₉H₂₀ClN₄O [M + H] Calc'd 355.1320 Found 355.1322 |
| 41 | 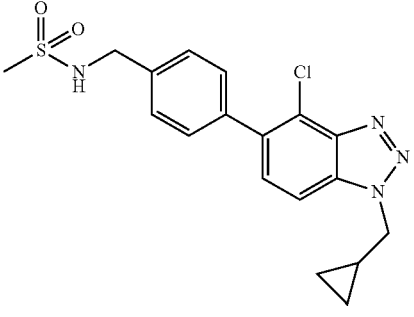 [SMILES: CS(=O)(=O)NCc1ccc(-c2ccc3c(nnn3CC3CC3)c2Cl)cc1] | N-{4-[4-chloro-1-(cyclopropylmethyl)-1H-benzotriazol-5-yl]benzyl}methanesulfonamide | C₁₈H₂₀ClN₄O₂S [M + H] Calc'd 391.0990 found 391.0991 |
| 42 | 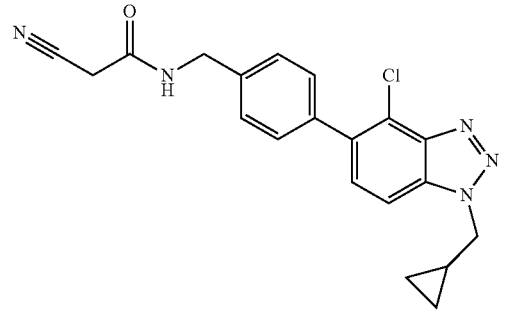 [SMILES: N#CCC(=O)NCc1ccc(-c2ccc3c(nnn3CC3CC3)c2Cl)cc1] | N-{4-[4-chloro-1-(cyclopropylmethyl)-1H-benzotriazol-5-yl]benzyl}-2-cyanoacetamide | C₂₀H₁₉ClN₅O [M + H] Calc'd 380.1273 found 380.1272 |
| 43 | 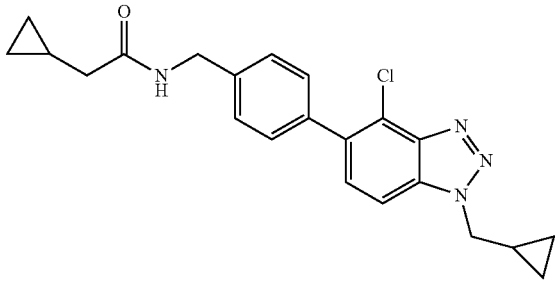 [SMILES: O=C(CC1CC1)NCc1ccc(-c2ccc3c(nnn3CC3CC3)c2Cl)cc1] | N-{4-[4-chloro-1-(cyclopropylmethyl)-1H-benzotriazol-5-yl]benzyl}-2-cyclopropylacetamide | C₂₂H₂₄ClN₄O [M + H] Calc'd 395.1633 found 395.1637 |
| 44 | 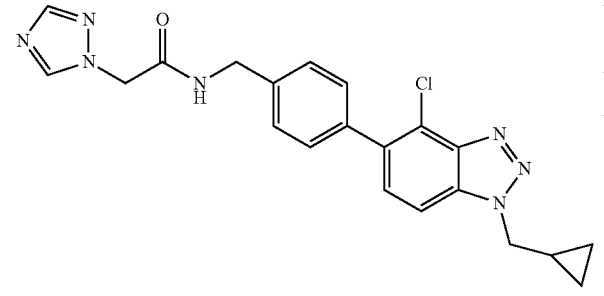 [SMILES: O=C(Cn1cncn1)NCc1ccc(-c2ccc3c(nnn3CC3CC3)c2Cl)cc1] | N-{4-[4-chloro-1-(cyclopropylmethyl)-1H-benzotriazol-5-yl]benzyl}-2-(1H-1,2,4-triazol-1-yl)acetamide | C₂₁H₂₁ClN₇O [M + H] Calc'd 422.1491 found 422.1492 |

| Ex. | STRUCTURE | NAME | HRMS/LRMS |
|---|---|---|---|
| 45 | 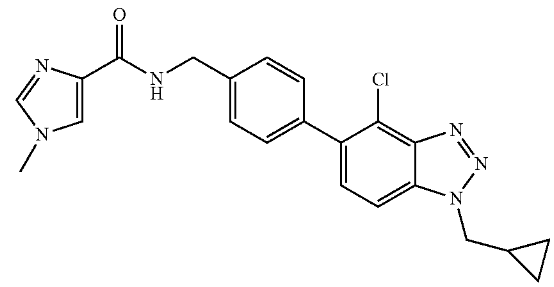 [SMILES: Cn1cnc(C(=O)NCc2ccc(-c3ccc4c(nnn4CC4CC4)c3Cl)cc2)c1] | N-{4-[4-chloro-1-(cyclopropylmethyl)-1H-benzotriazol-5-yl]benzyl}-1-methyl-1H-imidazole-4-carboxamide | $C_{22}H_{22}ClN_6O$ [M + H] Calc'd 421.1541 found 421.1549 |
| 46 | 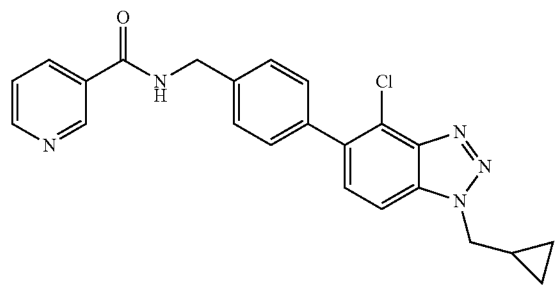 [SMILES: O=C(NCc1ccc(-c2ccc3c(nnn3CC3CC3)c2Cl)cc1)c1cccnc1] | N-{4-[4-chloro-1-(cyclopropylmethyl)-1H-benzotriazol-5-yl]benzyl}pyridine-3-carboxamide | $C_{23}H_{21}ClN_5O$ [M + H] Calc'd 418.1429 found 418.1433 |
| 47 | 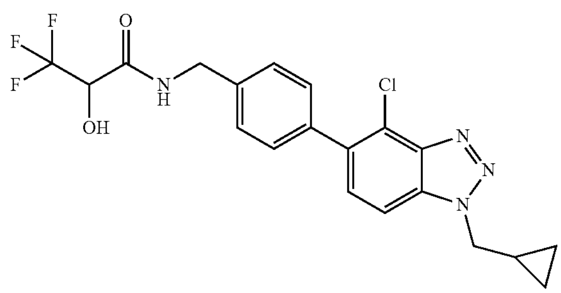 [SMILES: O=C(NCc1ccc(-c2ccc3c(nnn3CC3CC3)c2Cl)cc1)C(O)C(F)(F)F] | N-{4-[4-chloro-1-(cyclopropylmethyl)-1H-benzotriazol-5-yl]benzyl}-3,3,3-trifluoro-2-hydroxypropanamide | $C_{20}H_{19}ClF_3N_4O_2$ [M + H] Calc'd 439.1143 found 439.1150 |
| 48 | 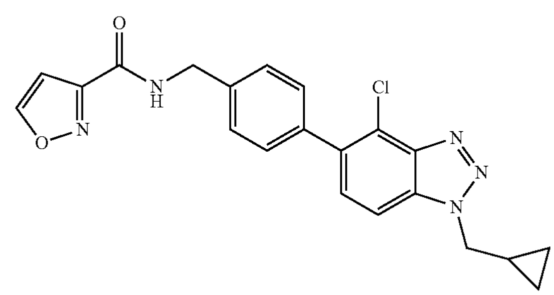 [SMILES: O=C(NCc1ccc(-c2ccc3c(nnn3CC3CC3)c2Cl)cc1)c1ccon1] | N-{4-[4-chloro-1-(cyclopropylmethyl)-1H-benzotriazol-5-yl]benzyl}isoxazole-3-carboxamide | $C_{21}H_{19}ClN_5O_2$ [M + H] Calc'd 408.1222 found 408.1222 |
| 49 | 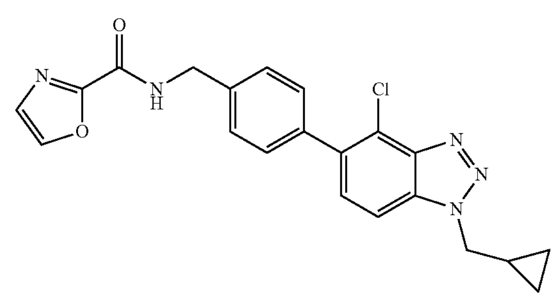 [SMILES: O=C(NCc1ccc(-c2ccc3c(nnn3CC3CC3)c2Cl)cc1)c1ncco1] | N-{4-[4-chloro-1-(cyclopropylmethyl)-1H-benzotriazol-5-yl]benzyl}-1,3-oxazole-2-carboxamide | $C_{21}H_{19}ClN_5O_2$ [M + H] Calc'd 408.1222 found 408.1222 |

| Ex. | STRUCTURE | NAME | HRMS/LRMS |
|---|---|---|---|
| 50 | 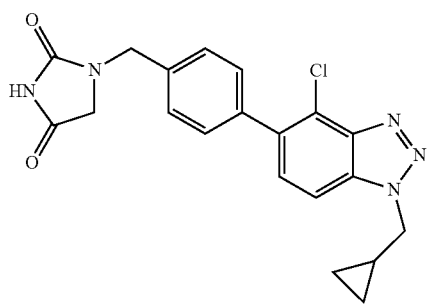 [SMILES: O=C1CN(Cc2ccc(-c3ccc4c(nnn4CC4CC4)c3Cl)cc2)C(=O)N1] | (2S)-N-{4-[4-chloro-1-(cyclopropylmethyl)-1H-benzotriazol-5-yl]benzyl}-2-hydroxypropanamide | $C_{20}H_{22}ClN_4O_2$ [M + H] Calc'd 385.1426 found 385.1430 |

Example 51

1-{4-[4-Chloro-1-(cyclopropylmethyl)-1H-benzotriazol-5-yl]benzyl}imidazolidine-2,4-dione Scheme for the Preparation of Example 51:

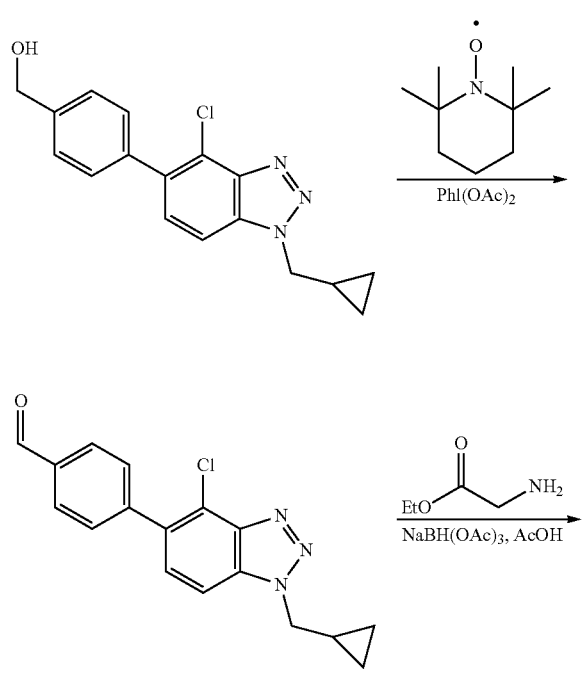

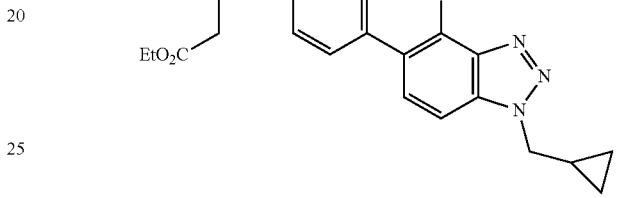

Step 1 Preparation of 4-[4-chloro-1-(cyclopropylmethyl)-1H-benzotriazol-5-yl]benzaldehyde {4-[4-Chloro-1-(cyclopropylmethyl)-1H-benzotriazol-5-yl]phenyl}methanol (Example 29, 50 mg, 0.16 mmol) was dissolved in dichloromethane (1.6 mL) and treated with diacetoxy(phenyl)-iodane (51 mg, 0.16 mmol) and (2,2,6,6-tetramethylpiperidin-1-yl)oxidanyl (2.5 mg, 0.016 mmol). The mixture was stirred at ambient tempuratures for 16 hours, diluted with dichloromethane and washed with sodium bicarbonate (2×30 ml, aqueous saturated). The organic extract was dried with sodium sulfate, filtered and concentrated in vacuo to afford the titled compound.

Step 2 Preparation of ethyl N-{4-[4-chloro-1-(cyclopropylmethyl)-1H-benzotriazol-5-yl]benzyl}glycinate 4-[4-Chloro-1-(cyclopropylmethyl)-1H-benzotriazol-5-yl]benzaldehyde (68 mg, 0.22 mmol) was dissolved in 1,2-dichloroethane (2.2 mL) and treated with ethyl aminoacetate hydrochloride (34 mg, 0.28 mmol) and acetic acid (25 uL, 0.44 mmol). The solution was stirred at ambient temperatures for 30 minutes and treated with sodium triacetoxyborohydride (51 mg, 0.24 mmol). The mixture was stirred at ambient temperature until complete, diluted with ethyl acetate (50 mL) and washed with sodium bicarbonate (2×30 mL, aqueous saturated). The organic extract was dried with sodium sulfate, filtered and concentrated in vacuo. The residue was purified by silica gel chromatography (100:0 to 97:3; dichloromethane:methanol) to afford the titled compound as a clear oil.

Step 3 Preparation of 1-{4-[4-chloro-1-(cyclopropylmethyl)-1H-benzotriazol-5-yl]benzyl}imidazolidine-2,4-dione Employing the procedures described in Example 4, substituting ethyl N-{4-[4-chloro-1-(cyclopropylmethyl)-1H-benzotriazol-5-yl]benzyl}glycinate for ethyl N-{4-[1-(cyclopropylmethyl)-4-(trifluoromethyl)-1H-benzotriazol-5-yl]benzyl}glycinate (Step 2) the titled compound was obtained: $^1$H-NMR (400 MHz, d$^6$-DMSO) δ 10.91 (1H, s); 8.01 (1H, d, J=8.6 Hz); 7.59 (1H, d, J=8.6 Hz); 7.52 (2H, d, J=8.2 Hz); 7.42 (2H, d, J=8.1 Hz); 4.67 (2H, d, J=7.2 Hz); 4.53 (2H, s); 3.93 (2H, s); 1.43-1.36 (1H, m); 0.60-0.54 (2H, m); 0.53-0.47 (2H, m) ppm; high resolution mass spectrometry (ES+) m/z 396.1240 [(M+H)$^+$; calculated for $C_{20}H_{19}ClN_5O_2$: 396.1222].

Example 52 tert-Butyl 4-{4-[4-chloro-1-(cyclopropylmethyl)-1H-benzotriazol-5-yl]benzyl}piperazine-1-carboxylate

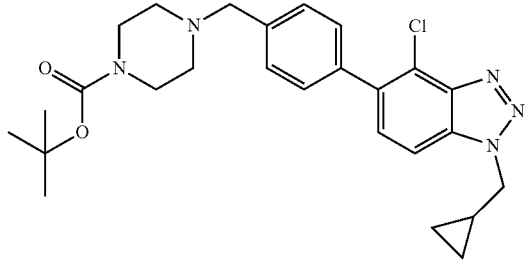 [SMILES: CC(C)(C)OC(=O)N1CCN(Cc2ccc(-c3ccc4c(nnn4CC4CC4)c3Cl)cc2)CC1]

Employing the procedures described in Example 4, substituting 4-[1-(cyclopropylmethyl)-4-chloro-1H-benzotriazole-5-yl]benzyl methanesulfonate for 1-(cyclopropylmethyl)-4-(trifluoromethyl)-1H-benzotriazol-5-yl methanesulfonate (Step 1), and, substituting tert-butyl piperazine-1-carboxylate for ethyl aminoacetate hydrochloride, the titled compound was obtained: $^1$H-NMR (400 MHz, d$^6$-DMSO) δ 8.04 (1H, d, J=8.6 Hz); 7.67-7.62 (4H, m); 7.60 (1H, d, J=8.5 Hz); 4.68 (2H, d, J=7.3 Hz); 4.41 (2H, br s); 2.56-2.48 (8H, m); 1.49-1.38 (1H, m); 1.42 (9H, s); 0.60-0.56 (2H, m); 0.52-0.49 (2H, m) ppm; high resolution mass spectrometry (ES+) m/z 482.2323 [(M+H)$^+$; calculated for $C_{26}H_{33}ClN_5O_2$: 482.2317].

The following compounds were prepared according to the general procedure described in Example 52, substituting the appropriate amine for tert-butyl piperazine-1-carboxylate. The starting materials are either commercially available, known in the literature or may be prepared from commercially available reagents using conventional reactions well known in the art.

| Ex. | STRUCTURE | NAME | HRMS/LRMS |
|---|---|---|---|
| 53 | 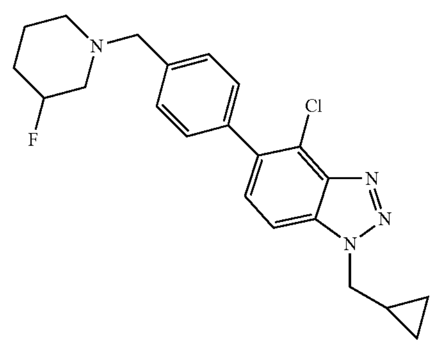 [SMILES: FC1CCCN(Cc2ccc(-c3ccc4c(nnn4CC4CC4)c3Cl)cc2)C1] | 4-chloro-1-(cyclopropylmethyl)-5-{4-[(3-fluoropiperidin-1-yl)methyl]phenyl}-1H-benzotriazole | $C_{22}H_{25}ClFN_4$ [M + H] calc. 399.1746 obs. 399.1743 |
| 54 | 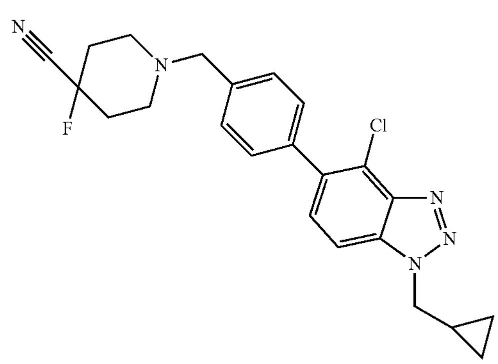 [SMILES: N#CC1(F)CCN(Cc2ccc(-c3ccc4c(nnn4CC4CC4)c3Cl)cc2)CC1] | 1-{4-[4-chloro-1-(cyclopropylmethyl)-1H-benzotriazol-5-yl]benzyl}-4-fluoropiperidine-4-carbonitrile | $C_{23}H_{24}ClFN_3$ [M + H] calc. 424.1699 obs. 424.1695 |

-continued

| Ex. | STRUCTURE | NAME | HRMS/LRMS |
|---|---|---|---|
| 55 | 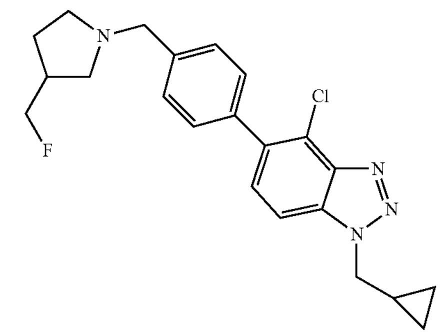 [SMILES: FCC1CCN(Cc2ccc(-c3ccc4c(nnn4CC4CC4)c3Cl)cc2)C1] | 4-chloro-1-(cyclopropylmethyl)-5-(4-{[3-(fluoromethyl)pyrrolidin-1-yl]methyl}phenyl)-1H-benzotriazole | $C_{22}H_{25}ClFN_4$ [M + H] calc. 399.1746 obs. 399.1742 |
| 56 | 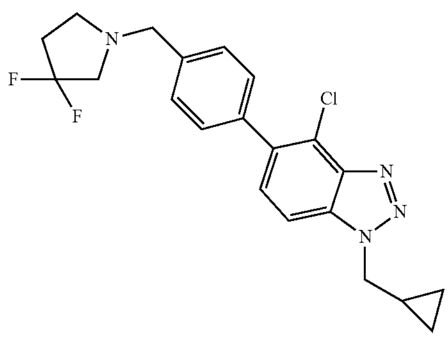 [SMILES: FC1(F)CCN(Cc2ccc(-c3ccc4c(nnn4CC4CC4)c3Cl)cc2)C1] | 4-chloro-1-(cyclopropylmethyl)-5-{4-[(3,3-difluoropyrrolidin-1-yl)methyl]phenyl}-1H-benzotriazole | $C_{21}H_{22}ClF_2N_4$ [M + H] calc. 403.1496 obs. 403.1490 |
| 57 | 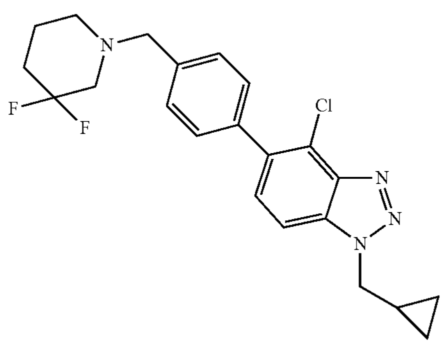 [SMILES: FC1(F)CCCN(Cc2ccc(-c3ccc4c(nnn4CC4CC4)c3Cl)cc2)C1] | 4-chloro-1-(cyclopropylmethyl)-5-{4-[(3,3-difluoropiperidin-1-yl)methyl]phenyl}-1H-benzotriazole | $C_{22}H_{24}ClF_2N_4$ [M + H] calc. 417.1652 obs. 417.1646 |
| 58 | 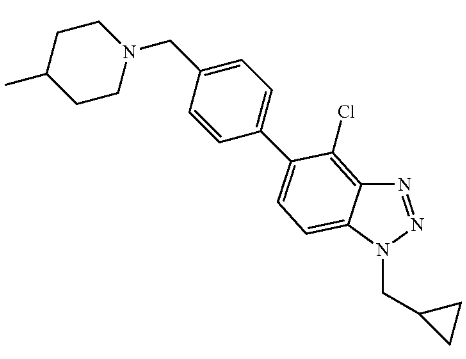 [SMILES: CC1CCN(Cc2ccc(-c3ccc4c(nnn4CC4CC4)c3Cl)cc2)CC1] | 4-chloro-1-(cyclopropylmethyl)-5-{4-[(4-methylpiperidin-1-yl)methyl]phenyl}-1H-benzotriazole | $C_{23}H_{28}ClN_4$ [M + H] calc. 395.1997 obs. 395.1992 |

-continued

| Ex. | STRUCTURE | NAME | HRMS/LRMS |
|---|---|---|---|
| 59 | 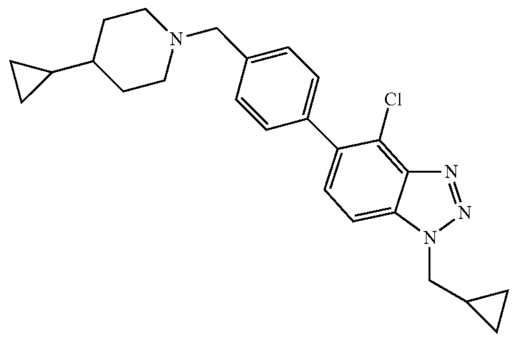 [SMILES: Clc1c(-c2ccc(CN3CCC(C4CC4)CC3)cc2)ccc2c1nnn2CC1CC1] | 4-chloro-1-(cyclopropylmethyl)-5-{4-[(4-cyclopropylpiperidin-1-yl)methyl]phenyl}-1H-benzotriazole | $C_{25}H_{30}ClN_4$ [M + H] calc. 421.2154 obs. 421.215 |
| 60 | 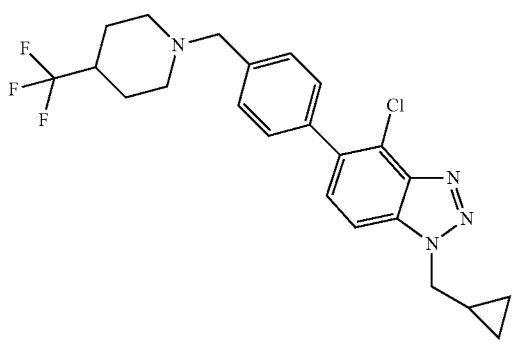 [SMILES: FC(F)(F)C1CCN(Cc2ccc(-c3ccc4c(nnn4CC4CC4)c3Cl)cc2)CC1] | 4-chloro-1-(cyclopropylmethyl)-5-(4-{[4-(trifluoromethyl)piperidin-1-yl]methyl}phenyl)-1H-benzotriazole | $C_{23}H_{25}ClF_3N_4$ [M + H] calc. 449.1714 obs. 449.171 |
| 61 | 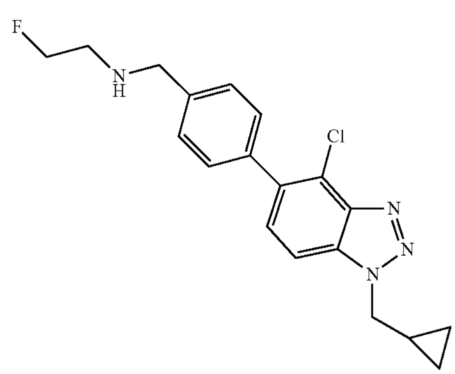 [SMILES: FCCNCc1ccc(-c2ccc3c(nnn3CC3CC3)c2Cl)cc1] | N-{4-[4-chloro-1-(cyclopropylmethyl)-1H-benzotriazol-5-yl]benzyl}-2-fluoroethanamine | $C_{19}H_{21}ClFN_4$ [M + H] calc. 359.1433 obs. 359.1429 |
| 62 | 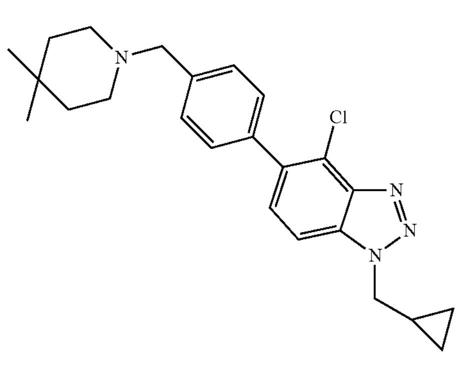 [SMILES: CC1(C)CCN(Cc2ccc(-c3ccc4c(nnn4CC4CC4)c3Cl)cc2)CC1] | 4-chloro-1-(cyclopropylmethyl)-5-{4-[(4,4-dimethylpiperidin-1-yl)methyl]phenyl}-1H-benzotriazole | $C_{24}H_{30}ClN_4$ [M + H] calc. 409.2154 obs. 409.2148 |

-continued

| Ex. | STRUCTURE | NAME | HRMS/LRMS |
|---|---|---|---|
| 63 | 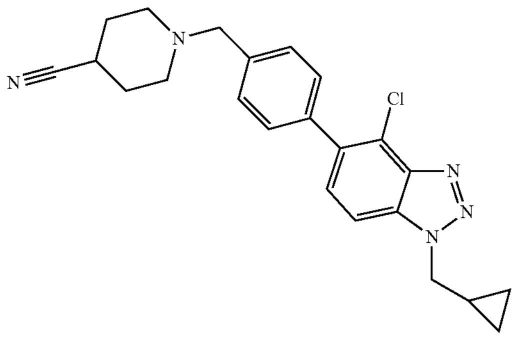 [SMILES: N#CC1CCN(Cc2ccc(-c3ccc4c(nnn4CC4CC4)c3Cl)cc2)CC1] | 1-{4-[4-chloro-1-(cyclopropylmethyl)-1H-benzotriazol-5-yl]benzyl}piperidine-4-carbonitrile | $C_{23}H_{25}ClN_5$ [M + H] calc. 406.1793 obs. 406.179 |
| 64 | 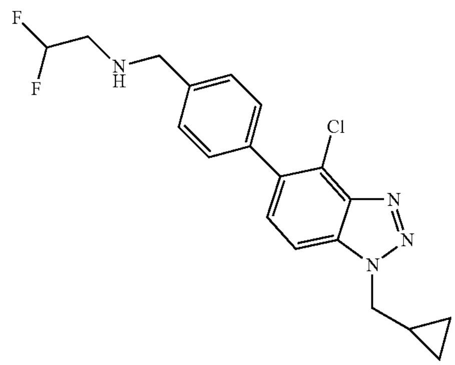 [SMILES: FC(F)CNCc1ccc(-c2ccc3c(nnn3CC3CC3)c2Cl)cc1] | N-{4-[4-chloro-1-(cyclopropylmethyl)-1H-benzotriazol-5-yl]benzyl}-2,2-difluoroethanamine | $C_{19}H_{20}ClF_2N_4$ [M + H] calc. 377.1339 obs. 377.1334 |
| 65 | 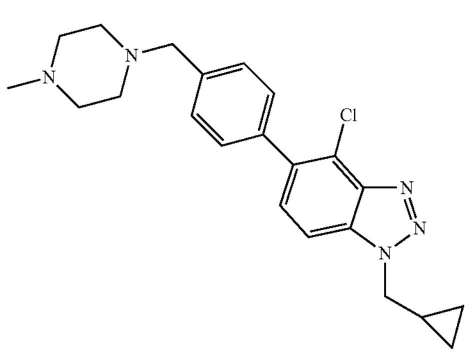 [SMILES: CN1CCN(Cc2ccc(-c3ccc4c(nnn4CC4CC4)c3Cl)cc2)CC1] | 4-chloro-1-(cyclopropylmethyl)-5-{4-[(4-methylpiperazin-1-yl)methyl]phenyl}-1H-benzotriazole | $C_{22}H_{27}ClN_5$ [M + H] calc. 396.195 obs. 396.1945 |
| 66 | 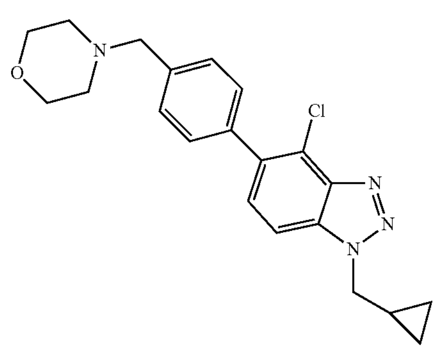 [SMILES: Clc1c(-c2ccc(CN3CCOCC3)cc2)ccc2c1nnn2CC1CC1] | 4-chloro-1-(cyclopropylmethyl)-5-[4-(morpholin-4-ylmethyl)phenyl]-1H-benzotriazole | $C_{21}H_{24}ClN_4O$ [M + H] calc. 383.1633 obs. 383.163 |

| Ex. | STRUCTURE | NAME | HRMS/LRMS |
|---|---|---|---|
| 67 | 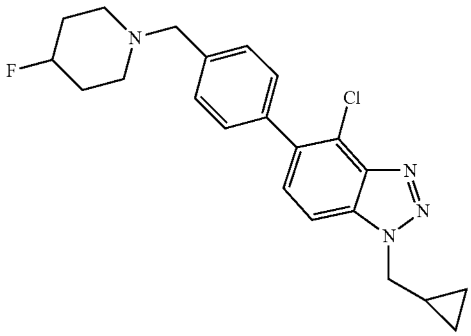 [SMILES: FC1CCN(Cc2ccc(-c3ccc4c(nnn4CC4CC4)c3Cl)cc2)CC1] | 4-chloro-1-(cyclopropylmethyl)-5-{4-[(4-fluoropiperidin-1-yl)methyl]phenyl}-1H-benzotriazole | C₂₂H₂₅ClFN₄ [M + H] calc. 399.1746 obs. 399.1743 |
| 68 | 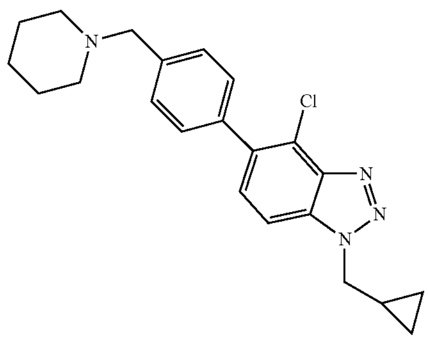 [SMILES: Clc1c(-c2ccc(CN3CCCCC3)cc2)ccc2c1nnn2CC1CC1] | 4-chloro-1-(cyclopropylmethyl)-5-[4-(piperidin-1-ylmethyl)phenyl]-1H-benzotriazole | C₂₂H₂₆ClN₄ [M + H] calc. 381.1841 obs. 381.1836 |
| 69 | 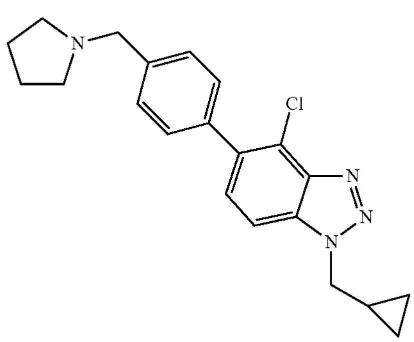 [SMILES: Clc1c(-c2ccc(CN3CCCC3)cc2)ccc2c1nnn2CC1CC1] | 4-chloro-1-(cyclopropylmethyl)-5-[4-(pyrrolidin-1-ylmethyl)phenyl]-1H-benzotriazole | C₂₁H₂₄ClN₄ [M + H] calc. 367.1684 obs. 367.1679 |
| 70 | 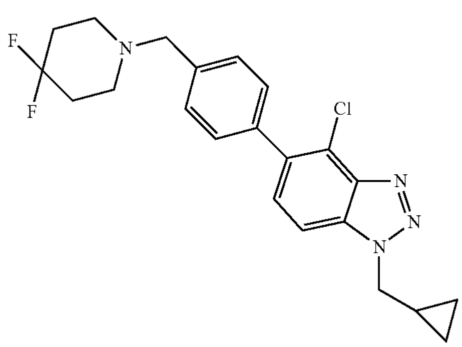 [SMILES: FC1(F)CCN(Cc2ccc(-c3ccc4c(nnn4CC4CC4)c3Cl)cc2)CC1] | 4-chloro-1-(cyclopropylmethyl)-5-{4-[(4,4-difluoropiperidin-1-yl)methyl]phenyl}-1H-benzotriazole | C₂₂H₂₄ClF₂N₄ [M + H] calc. 417.1652 obs. 417.1648 |

Example 71

4-Chloro-1-(cyclopropylmethyl)-5-[4-(piperazin-1-ylmethyl)phenyl]-1H-benzotriazole

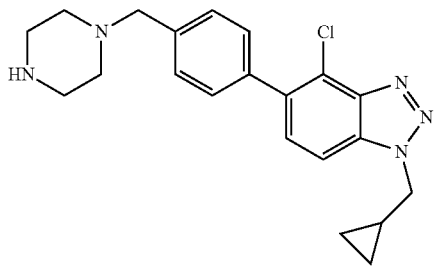 [SMILES: Clc1c(-c2ccc(CN3CCNCC3)cc2)ccc2c1nnn2CC1CC1]

tert-Butyl 4-{4-[4-chloro-1-(cyclopropylmethyl)-1H-benzotriazol-5-yl]benzyl}piperazine-1-carboxylate (Example 52, 430 mg, 0.89 mmol) was dissolved in a dichloromethane (8.9 mL) and methanol (8.9 mL), cooled to 0° C. and treated with a hydrochloric acid (2.2 mL, 4 M in dioxane, 8.9 mmol). The mixture was warmed to ambient temperature and treated with hydrochloric acid (200 μL, 12 N aqueous). The mixture was stirred at ambient temperatures until complete, at which time the mixture was treated with aqueous saturated sodium bicarbonate, diluted with water and extracted with ethyl acetate (3×40 mL). The combined organic extracts were dried with sodium sulfate, filtered and concentrated in vacuo. The residue was purified by silica gel chromatography (100:0 to 90:5; dichloromethane:methanol) to afford the product as a clear oil: $^1$H-NMR (400 MHz, CDCl$_3$) δ 7.51 (1H, d, J=1.9 Hz); 7.48-7.42 (5H, m); 4.56 (2H, d, J=7.0 Hz); 3.57 (2H, s); 2.93 (5H, t, J=4.8 Hz); 2.81 (3H, t, J=4.8 Hz); 1.49-1.38 (1H, m); 0.73-0.65 (2H, m); 0.57-0.48 (2H, m) ppm; high resolution mass spectrometry (ES+) m/z 382.1796 [(M+H)$^+$; calculated for C$_{21}$H$_{25}$ClN$_5$: 382.1793].

Example 72

3-(4-{4-[4-Chloro-1-(cyclopropylmethyl)-1H-benzotriazol-5-yl]benzyl}piperazin-1-yl)-3-oxopropanenitrile

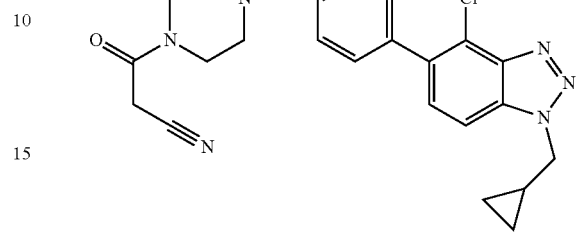

To a stirring solution of 4-chloro-1-(cyclopropylmethyl)-5-[4-(piperazin-1-ylmethyl)phenyl]-1H-benzotriazole (Example 71, 15 mg, 0.039 mmol) in dichloromethane (530 uL) was added cyanoacetic acid (6.7 mg, 0.079 mmol) and (benzotriazol-1-yloxy)tripyrrolidinophosphonium hexafluorophosphate (31 mg, 0.059 mmol) and diisopropylethylamine (34 uL, 0.20 mmol). After stirring for 2 hours at ambient temperature, the mixture was concentrated in vacuo and the residue was purified by preparative reverse phase HPLC (95:5 to 5:95; water containing 0.1% trifluoroacetic acid:acetonitrile containing 0.1% trifluoroacetic acid) to afford the titled compound: $^1$H-NMR (400 MHz, d$^6$-DMSO) δ 8.01 (1H, d, J=8.5 Hz), 7.66 (2H, d, J=7.7 Hz), 7.62 (2H, d, J=7.7 Hz), 7.60 (1H, d, J=8.6 Hz), 4.68 (2H, d, J=7.4 Hz), 4.39 (1H, br s), 2.57-2.46 (10H, m), 1.75-1.72 (2H, m), 1.49-1.38 (1H, m), 0.60-0.56 (2H, m), 0.52-0.49 (2H, m) ppm high resolution mass spectrometry (ES+) m/z 449.1862 [(M+H)$^+$; calculated for C$_{24}$H$_{26}$ClN$_6$O: 449.1851].

The following compounds were prepared according to the general procedure described in Example 72, substituting the appropriate acid for cyanoacetic acid. The starting materials are either commercially available, known in the literature or may be prepared from commercially available reagents using conventional reactions well known in the art.

| Ex. | STRUCTURE | NAME | HRMS/LRMS |
|---|---|---|---|
| 73 | 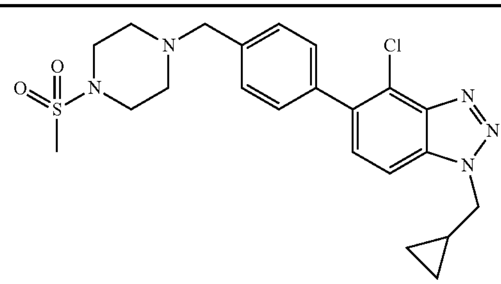 | 4-chloro-1-(cyclopropylmethyl)-5-(4-{[4-(methylsulfonyl)piperazin-1-yl]methyl}phenyl)-1H-benzotriazole | C$_{22}$H$_{26}$ClN$_5$O$_2$S [M + H] Calc'd 460.1571, found 460.1580 |
| 74 | 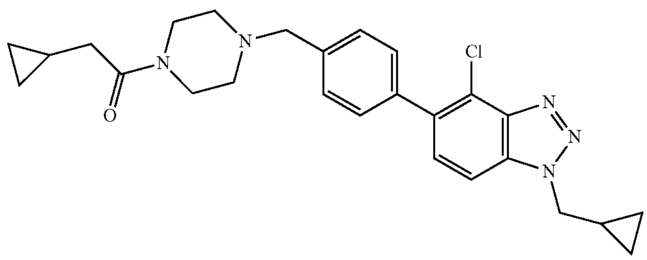 [SMILES: O=C(CC1CC1)N1CCN(Cc2ccc(-c3ccc4c(nnn4CC4CC4)c3Cl)cc2)CC1] | 4-chloro-5-(4-{[4-(cyclopropylacetyl)piperazin-1-yl]methyl}phenyl)-1-(cyclopropylmethyl)-1H-benzotriazole | C$_{26}$H$_{31}$ClN$_5$O [M + H] Calc'd 464.2213, found 464.2226 |

-continued

| Ex. | STRUCTURE | NAME | HRMS/LRMS |
|---|---|---|---|
| 75 | 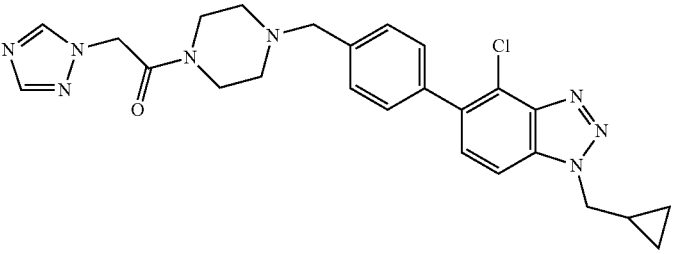 [SMILES: O=C(Cn1cncn1)N1CCN(Cc2ccc(-c3ccc4c(nnn4CC4CC4)c3Cl)cc2)CC1] | 4-chloro-1-(cyclopropylmethyl)-5-(4-{[4-(1H-1,2,4-triazol-1-ylacetyl)piperazin-1-yl]methyl}phenyl)-1H-benzotriazole | $C_{25}H_{28}ClN_8O$ [M + H] Calc'd 491.2071, found 491.2085 |
| 76 | 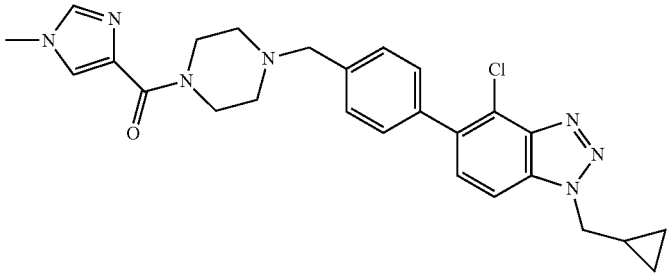 [SMILES: Cn1cnc(C(=O)N2CCN(Cc3ccc(-c4ccc5c(nnn5CC5CC5)c4Cl)cc3)CC2)c1] | 4-chloro-1-(cyclopropylmethyl)-5-[4-({4-[(1-methyl-1H-imidazol-4-yl)carbonyl]piperazin-1-yl}methyl)phenyl]-1H-benzotriazole | $C_{26}H_{29}ClN_7O$ [M + H] Calc'd 490.2118, found 490.2137 |
| 77 | 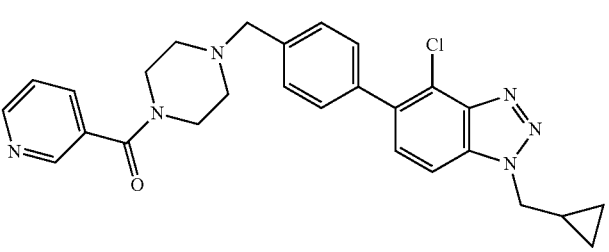 [SMILES: O=C(c1cccnc1)N1CCN(Cc2ccc(-c3ccc4c(nnn4CC4CC4)c3Cl)cc2)CC1] | 4-chloro-1-(cyclopropylmethyl)-5-(4-{[4-(pyridin-3-ylcarbonyl)piperazin-1-yl]methyl}phenyl-1H-benzotriazole | $C_{27}H_{28}ClN_6O$ [M + H] Calc'd 487.2009, found 487.2027 |
| 78 | 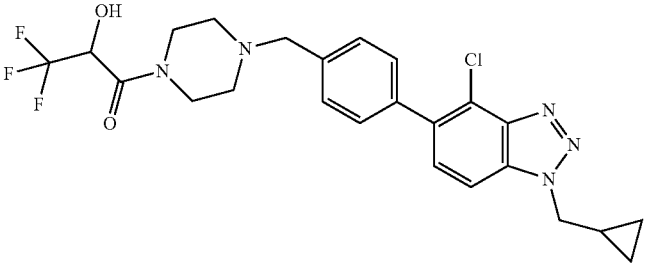 [SMILES: O=C(C(O)C(F)(F)F)N1CCN(Cc2ccc(-c3ccc4c(nnn4CC4CC4)c3Cl)cc2)CC1] | 3-(4-{4-[4-chloro-1-(cyclopropylmethyl)-1H-benzotriazol-5-yl]benzyl}piperazin-1-yl)-1,1,1-trifluoro-3-oxopropan-2-ol | $C_{24}H_{26}ClF_3N_5O_2$ [M + H] Calc'd 508.1724, found 508.1738 |
| 79 | 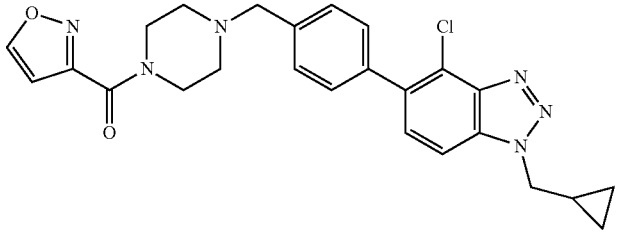 [SMILES: O=C(c1ccon1)N1CCN(Cc2ccc(-c3ccc4c(nnn4CC4CC4)c3Cl)cc2)CC1] | 4-chloro-1-(cyclopropylmethyl)-5-(4-{[4-(isoxazol-3-ylcarbonyl)piperazin-1-yl]methyl}phenyl)-1H-benzotriazole | $C_{25}H_{26}ClN_6O_2$ [M + H] Calc'd 477.1802, found 477.1814 |
| 80 | 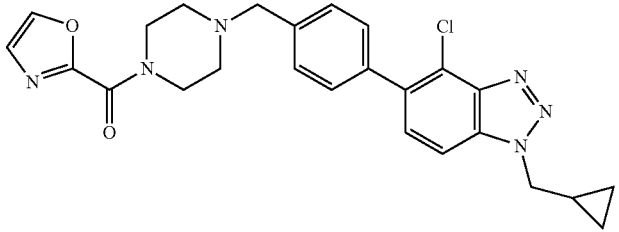 [SMILES: O=C(c1ncco1)N1CCN(Cc2ccc(-c3ccc4c(nnn4CC4CC4)c3Cl)cc2)CC1] | 4-chloro-1-(cyclopropylmethyl)-5-(4-{[4-(1,3-oxazol-2-ylcarbonyl)piperazin-1-yl]methyl}phenyl)-1H-benzotriazole | $C_{25}H_{25}ClN_6O_2$ [M + H] Calc'd 477.1802, found 477.1819 |

| Ex. | STRUCTURE | NAME | HRMS/LRMS |
|---|---|---|---|
| 81 | 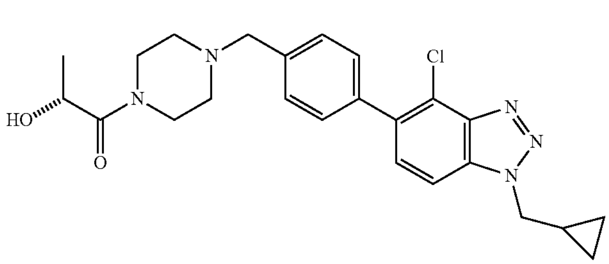 [SMILES: C[C@@H](O)C(=O)N1CCN(Cc2ccc(-c3ccc4c(nnn4CC4CC4)c3Cl)cc2)CC1] | (2S)-1-(4-{4-[4-chloro-1-(cyclopropylmethyl)-1H-benzotriazol-5-yl]benzyl}piperazin-1-yl)-1-oxopropan-2-ol | $C_{24}H_{29}ClN_5O_2$ [M + H] Calc'd 454.2005, found 454.2023 |
| 82 | 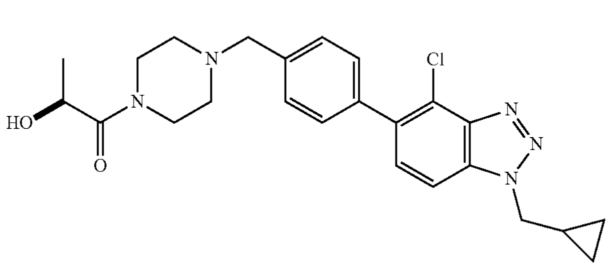 [SMILES: C[C@H](O)C(=O)N1CCN(Cc2ccc(-c3ccc4c(nnn4CC4CC4)c3Cl)cc2)CC1] | (2R)-1-(4-{4-[4-chloro-1-(cyclopropylmethyl)-1H-benzotriazol-5-yl]benzyl}piperazin-1-yl)-1-oxopropan-2-ol | $C_{24}H_{29}ClN_5O_2$ [M + H] Calc'd 454.2005, found 454.2019 |

Example 83

Ethyl N-({4-[4-chloro-1-(cyclopropylmethyl)-1H-benzotriazol-5-yl]benzyl}carbamoyl)glycinate

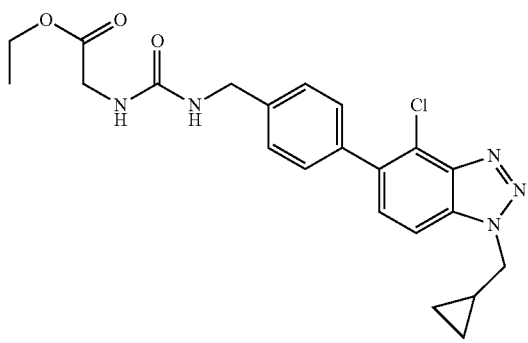 [SMILES: CCOC(=O)CNC(=O)NCc1ccc(-c2ccc3c(nnn3CC3CC3)c2Cl)cc1]

Scheme for the Preparation of Example 83:

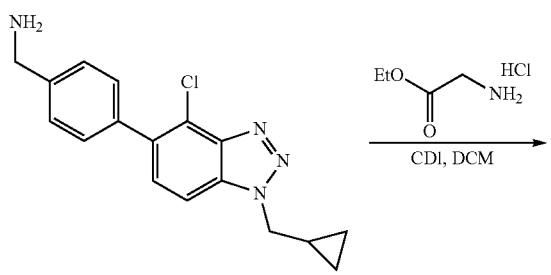

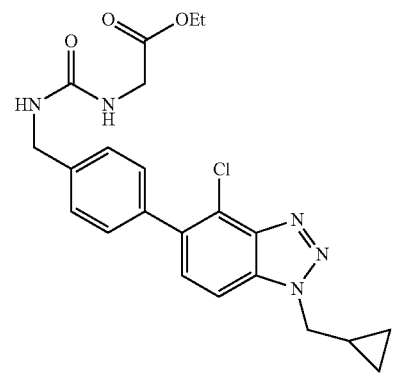

1-{4-[4-Chloro-1-(cyclopropylmethyl)-1H-benzotriazol-5-yl]phenyl}methanamine (58 mg, 1.8 mmol) was dissolved in dichloromethane (1.8 mL) and treated with carbonyldiimidazole (0.15 g, 0.93 mmol, 5 equiv). The mixture was stirred at ambient temperatures for 2 hours and then treated with ethyl aminoacetate hydrochloride (0.26 g, 1.8 mmol, 10 equiv). The mixture was stirred until complete, diluted with dichloromethane (30 mL) and washed with sodium bicarbonate (2×30 mL, aqueous saturated). The organic layer was dried with sodium sulfate, filtered and concentrated in vacuo. The residue was purified by preparative reverse phase HPLC (85:15 to 35:65; water containing 0.1% trifluoroacetic acid: acetonitrile containing 0.1% trifluoroacetic acid) to afford the titled compound: $^1$H-NMR (400 MHz, CDCl$_3$) δ 7.53-7.40 (6H, m); 4.55 (2H, dd, J=6.9, 3.8 Hz); 4.49 (2H, m); 4.25-4.17 (2H, m); 4.02 (2H, s); 1.47-1.38 (1H, m); 1.27 (3H, t, J=6.6 Hz); 0.71-0.66 (2H, m); 0.54-0.49 (2H, m) ppm; high resolution mass spectrometry (ES+) m/z 442.1660 [(M+H)$^+$; calculated for $C_{22}H_{25}ClN_5O_3$: 442.1640].

Example 84

3-{4-[4-Chloro-1-(cyclopropylmethyl)-1H-benzotriazol-5-yl]benzyl}imidazolidine-2,4-dione

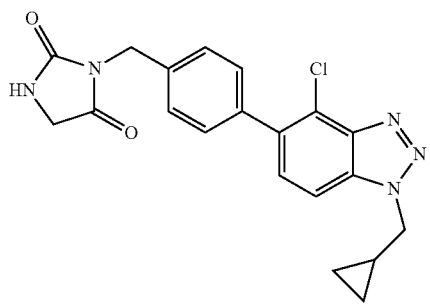 [SMILES: O=C1CNC(=O)N1Cc1ccc(-c2ccc3c(nnn3CC3CC3)c2Cl)cc1]

Scheme for the Preparation of Example 84:

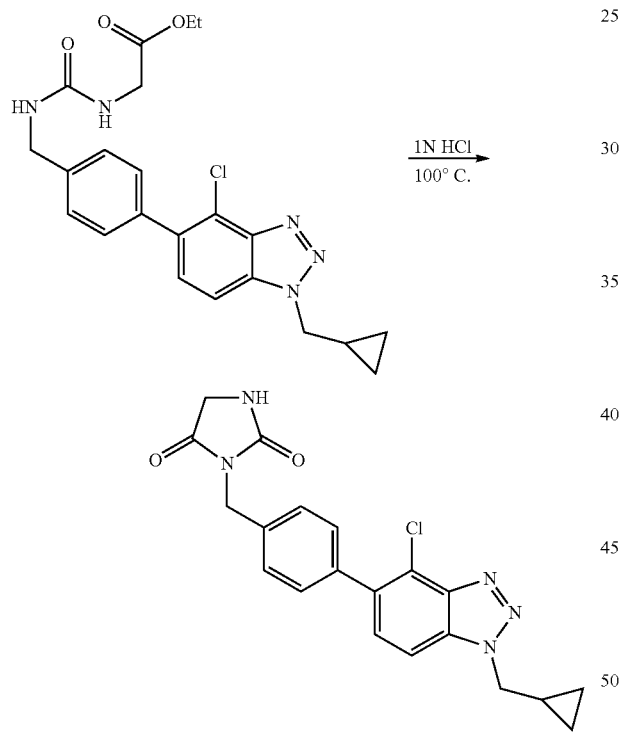

Ethyl N-({4-[4-chloro-1-(cyclopropylmethyl)-1H-benzotriazol-5-yl]benzyl}carbamoyl)glycinate (Example 83, 30 mg, 0.068 mmol) was dissolved in hydrochloric acid (1.4 mL, 1 N aqueous) and placed into an oil-bath preheated at 100° C. for 1.5 hours. The mixture was cooled to ambient temperature, treated with sodium bicarbonate (aqueous saturated) and extracted with ethyl acetate (3×30 mL). The combined organic extracts were dried with sodium sulfate, filtered and concentrated in vacuo. The residue was purified by preparative reverse phase HPLC (85:15 to 36:64; water containing 0.1% trifluoroacetic acid:acetonitrile containing 0.1% trifluoroacetic acid) to afford the titled compound: $^1$H-NMR (400 MHz, d$^6$-DMSO) δ 8.17 (1H, s); 8.00 (1H, d, J=8.5 Hz); 7.58 (1H, d, J=8.6 Hz); 7.49 (2H, d, J=8.2 Hz); 7.41 (2H, d, J=8.2 Hz); 4.67 (2H, d, J=7.2 Hz); 4.62 (2H, s); 4.02 (2H, s); 1.43-1.37 (1H, m); 0.59-0.55 (2H, m); 0.51-0.48 (2H, m) ppm; high resolution mass spectrometry (ES+) m/z 396.1242 [(M+H)$^+$; calculated for $C_{20}H_{19}ClN_5O_2$: 396.1222].

Example 85

3-{4-[4-Chloro-1-(cyclopropylmethyl)-1H-benzotriazol-5-yl]benzyl}-1-methylimidazolidine-2,4-dione

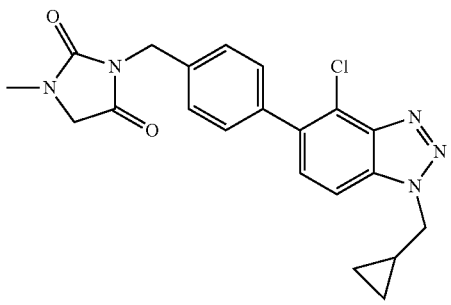 [SMILES: CN1CC(=O)N(Cc2ccc(-c3ccc4c(nnn4CC4CC4)c3Cl)cc2)C1=O]

Scheme for the Preparation of Example 85:

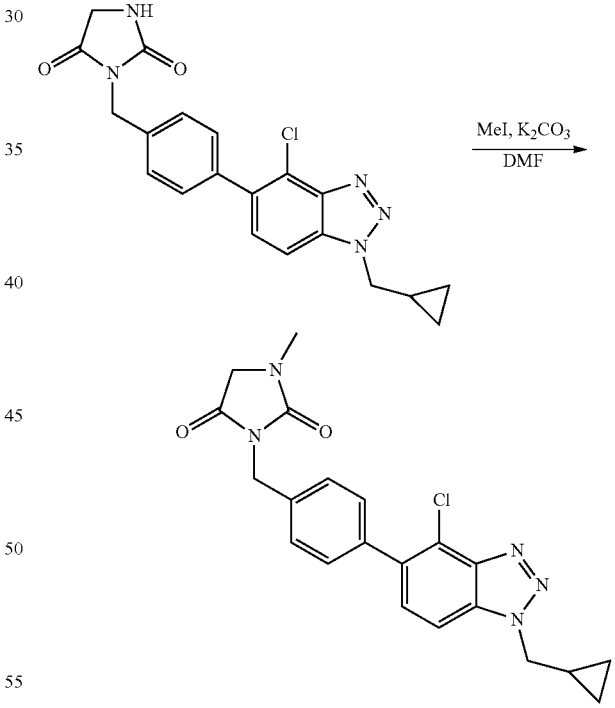

3-{4-[4-Chloro-1-(cyclopropylmethyl)-1H-benzotriazol-5-yl]benzyl}imidazolidine-2,4-dione (Example 84, 19 mg, 0.048 mmol) was dissolved in N,N-dimethylformamide and treated with potassium carbonate (8.6 mg, 0.062 mmol, 1.3 equiv) and iodomethane (5.4 µL, 0.086 mmol, 1.8 equiv). After stirring at ambient temperature for 1 hour, additional iodomethane (5.4 µL, 0.086 mmol, 1.8 equiv) and potassium carbonate (8.6 mg, 0.062 mmol, 1.3 equiv) were added and the mixture was placed into a preheated oil bath at 50° C. for 2.5 hours. The mixture was cooled to ambient temperature, diluted with ethyl acetate (30 mL) and washed with sodium bicarbonate (2×20 mL, aqueous saturated). The organic extract was dried with sodium sulfate, filtered and concentrated in vacuo. The residue was purified by preparative reverse phase HPLC (85:15 to 36:64; water with 0.05% trifluoroacetic acid:acetonitrile with 0.05% trifluoroacetic acid) to afford the titled compound: $^1$H-NMR (400 MHz, d$^6$-DMSO) δ 7.53 (1H, d, J=6.5 Hz); 7.51 (2H, d, J=6.7 Hz); 7.48 (2H, d, J=2.7 Hz); 7.45 (1H, d, J=2.9 Hz); 4.73 (2H, s); 4.55 (2H, d, J=7.2 Hz); 3.92 (2H, s); 3.02 (3H, s); 1.47-1.39 (1H, m); 0.72-0.67 (2H, m); 0.54-0.50 (2H, m) ppm; high resolution mass spectrometry (ES+) m/z 410.1380 [(M+H)$^+$; calculated for $C_{21}H_{21}ClN_5O_2$: 410.1378].

What is claimed is:

1. A compound of Formula I or Formula II

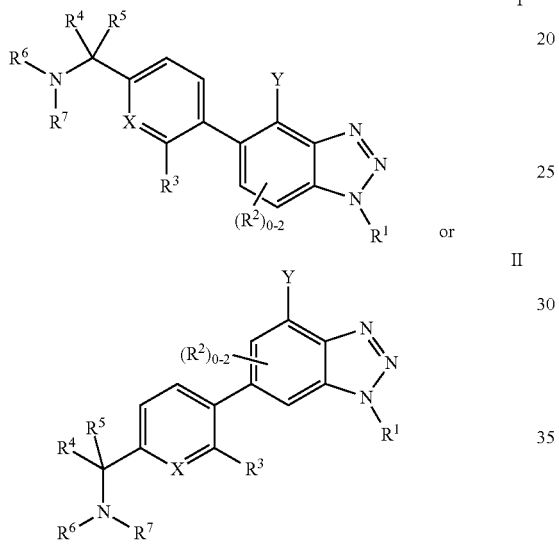

or a pharmaceutically acceptable salt thereof, wherein:

R$^1$ is selected from the group consisting of:
(1) $C_{2-8}$alkyl,
(2) $C_{2-8}$alkenyl,
(3) $C_{2-8}$alkynyl,
(4) $C_{3-6}$cycloalkyl-$(CH_2)_p$—, wherein p is 1, 2, 3 or 4, and
(5) benzyl, wherein groups (1) to (5) above are optionally substituted with 1 to 3 R$^a$ groups;

each R$^a$ and R$^2$ is independently selected from the group consisting of: halo, OH, $C_{1-4}$alkyl, $C_{1-4}$alkoxy, CF$_3$, —OCF$_3$ and —CN;

Y is selected from the group consisting of: H, halo, CN, $C_{1-4}$alkyl, $C_{2-4}$alkenyl and $CH_3$—$S(O)_q$—, wherein said $C_{1-4}$alkyl and $C_{2-4}$alkenyl are optionally substituted with hydroxy, oxo and one or more fluoro groups as allowed by valence;

X is C(R$^8$) or N, or the N-oxide thereof;

R$^3$ is selected from H or halogen;

R$^4$ and R$^5$ are independently selected from H and $C_{1-4}$alkyl, optionally substituted with hydroxy, or R$^4$ and R$^5$ may be joined together to form carbonyl;

R$^6$ is selected from the group consisting of H, —C(O)—R$^9$ and —S(O)$_r$—R$^9$, and R$^7$ is H or $C_{1-4}$alkyl, or R$^6$ and R$^7$ and the nitrogen atom to which they are attached may be joined together to form a 5-membered non-aromatic ring optionally containing one or two additional heteroatoms selected from N, S or O, said ring optionally substituted with one or two oxo groups and one to three substituents independently selected from halo, CN, R$^9$, —O—R$^9$, —C(O)—R$^9$—C(O)—O—R$^9$ and —S(O)$_t$—R$^9$, or R$^6$ and R$^7$ and the nitrogen atom to which they are attached may be joined together to form a 6-membered non-aromatic ring optionally containing one or two additional heteroatoms selected from N or S, said ring optionally substituted with one or two oxo groups and one to three substituents independently selected from halo, CN, R$^9$, —O—R$^9$, —C(O)—R$^9$—C(O)—O—R$^9$ and —S(O)$_t$—R$^9$, or R$^6$ and R$^7$ and the nitrogen atom to which they are attached are joined together to form morpholine which is optionally substituted with one to three substituents independently selected from halo, CN, R$^9$, —O—R$^9$, —C(O)—R$^9$, —C(O)—O—R$^9$ and —S(O)$_t$—R$^9$, or R$^6$ and R$^7$ and the nitrogen atom to which they are attached may be joined together to form azide;

R$^8$ is selected from H and $C_{1-4}$alkyl;

each R$^9$ independently represents: (1) H, $C_{1-6}$alkyl, $C_{2-6}$alkenyl, $C_{2-6}$alkynyl, $C_{3-10}$cycloalkyl, $C_{3-10}$cycloalkyl$C_{1-4}$alkyl, $C_{3-10}$cycloalkenyl or $C_{3-10}$cycloalkenyl$C_{1-4}$alkyl, any of which except H optionally bear OH, CN, CF$_3$ and $C_{1-4}$alkoxy and up to 5 halogen atoms; (2) phenyl, benzyl or heteroaryl, optionally bridged with a methylene, any of which optionally bear up to 3 substituents independently selected from halogen, OH, oxo, CN, CF$_3$, $C_{1-4}$alkyl, $C_{1-4}$hydroxyalkyl, $C_{3-6}$cycloalkyl, phenyl, heteroaryl, $C_{1-4}$alkoxy, acetyl, amino, carbamoyl, $CO_2$—$C_{1-4}$alkyl, $C_{1-4}$alkylamino and di($C_{1-4}$alkyl) amino; and (3) Het, optionally bridged with a methylene and said Het optionally bearing up to 3 substituents independently selected from halogen, OH, oxo, CN, CF$_3$, $C_{1-4}$alkyl, $C_{1-4}$hydroxyalkyl, $C_{3-6}$cycloalkyl, phenyl, heteroaryl, $C_{1-4}$alkoxy, acetyl, amino, carbamoyl, $CO_2$—$C_{1-4}$alkyl, $C_{1-4}$alkylamino and di($C_{1-4}$alkyl)amino;

each "heteroaryl" independently defined as 5- or 6-membered aromatic monocyclic or 9- or 10-membered aromatic bicyclic ring systems, in which at least one ring atom is selected from N or N-oxide, O and S;

each "Het" independently defined as nonaromatic or partially aromatic mono- or bicyclic heterocyclic systems of up to 10 ring atoms, in which at least one ring atom is selected from N, O and S, where the sulfur atom may be in the form of the S-oxide or S,S-dioxide; and q, r and t are independently 0, 1 or 2.

2. The compound according to claim 1, or a pharmaceutically acceptable salt thereof, wherein R$^1$ is cyclopropylmethyl, 2-methylpropyl or 2,2-dimethylpropyl.

3. The compound according to claim 1, or a pharmaceutically acceptable salt thereof, wherein R$^2$ is not present.

4. The compound according to claim 1, or a pharmaceutically acceptable salt thereof, wherein Y is hydrogen, chloro, bromo, methylsulfanyl, methylsulfinyl, methylsulfonyl, cyano, methyl, ethyl, propyl, isopropyl, prop-2-en-1-yl, formyl, hydroxymethyl, fluoromethyl, difluoromethyl and trifluoromethyl.

5. The compound according to claim 1, or a pharmaceutically acceptable salt thereof, wherein X is N.

6. The compound according to claim 5, or a pharmaceutically acceptable salt thereof, wherein $R^3$ is F.

7. The compound according to claim 1, or a pharmaceutically acceptable salt thereof, wherein X is $C(R^8)$, $R^3$ is H or F, and $R^8$ is H.

8. The compound according to claim 1, or a pharmaceutically acceptable salt thereof, wherein $R^6$ is selected from the group consisting of H, —C(O)—$R^9$ and —S(O)$_r$—$R^9$, and $R^7$ is H.

9. The compound according to claim 1, or a pharmaceutically acceptable salt thereof, wherein $R^6$ and $R^7$ and the nitrogen atom to which they are attached are joined together to form a 5- or 6-membered non-aromatic ring optionally containing one or two additional heteroatoms selected from N or S N, said ring optionally substituted with one or two oxo groups and one to three substituents independently selected from halo, CN, $R^9$, —O—$R^9$, —C(O)—$R^9$, —C(O)—O—$R^9$ and —S(O)$_r$—$R^9$.

10. The compound according to claim 1, or a pharmaceutically acceptable salt thereof, wherein $R^6$ and $R^7$ and the nitrogen atom to which they are attached are joined together to form 3-methylimidazolidine-2,4-dione.

11. The compound according to claim 1, or a pharmaceutically acceptable salt thereof, wherein $R^6$ and $R^7$ and the nitrogen atom to which they are attached are joined together to form pyrrolidine, piperidine, piperazine or morpholine, each of which is optionally substituted with one to three substituents independently selected from halo, CN, $R^9$, —O—$R^9$, —C(O)—$R^9$, —C(O)—O—$R^9$ and —S(O)$_r$—$R^9$.

12. The compound according to claim 1, or a pharmaceutically acceptable salt thereof, wherein $R^4$ and $R^5$ are H.

13. The compound according to claim 1, or a pharmaceutically acceptable salt thereof, of Formula I wherein:
$R^1$ is cyclopropylmethyl, 2-methylpropyl or 2,2-dimethylpropyl;
$R^2$ is not present;
Y is hydrogen, chloro, bromo, methylsulfanyl, methylsulfinyl, methylsulfonyl, cyano, methyl, ethyl, propyl, isopropyl, prop-2-en-1-yl, formyl, hydroxymethyl, fluoromethyl, difluoromethyl and trifluoromethyl;
$R^3$ is H or F;
$R^4$ and $R^5$ are H;
$R^6$ and $R^7$ and the nitrogen atom to which they are attached are joined together to form 3-methylimidazolidine-2,4-dione, or $R^6$ and $R^7$ and the nitrogen atom to which they are attached are joined together to form pyrrolidine, piperidine, piperazine or morpholine, each of which is optionally substituted with one to three substituents independently selected from halo, CN, $R^9$, —O—$R^9$, —C(O)—$R^9$, —C(O)—O—$R^9$ and —S(O)$_r$—$R^9$;
$R^8$ is H;
each $R^9$ independently represents: (1) $C_{1-4}$alkyl, cyclopropyl and cyclopropylmethyl, any of which optionally bear OH, CN and up to 5 halogen atoms, and (2) triazolyl, imidazolyl, isoxazolyl or pyridyl, each optionally bridged with a methylene, and each optionally substituted with methyl.

14. The compound according to claim 1, or a pharmaceutically acceptable salt thereof, of Formula I wherein:
$R^1$ is cyclopropylmethyl, 2-methylpropyl or 2,2-dimethylpropyl;
$R^2$ is not present;
Y is hydrogen, chloro, bromo, methylsulfanyl, methylsulfinyl, methylsulfonyl, cyano, methyl, ethyl, propyl, isopropyl, prop-2-en-1-yl, formyl, hydroxymethyl, fluoromethyl, difluoromethyl and trifluoromethyl;
$R^3$ is H or F;
$R^4$ and $R^5$ are H;
$R^6$ is selected from the group consisting of H, —C(O)—$R^9$ and —S(O)$_r$—$R^9$;
$R^7$ and $R^8$ are H;
each $R^9$ independently represents: (1) $C_{1-4}$alkyl, cyclopropyl and cyclopropylmethyl, any of which optionally bear OH, CN and up to 5 halogen atoms, and (2) triazolyl, imidazolyl, isoxazolyl or pyridyl, each optionally bridged with a methylene, and each optionally substituted with methyl.

15. A compound according to claim 1 selected from the following group:

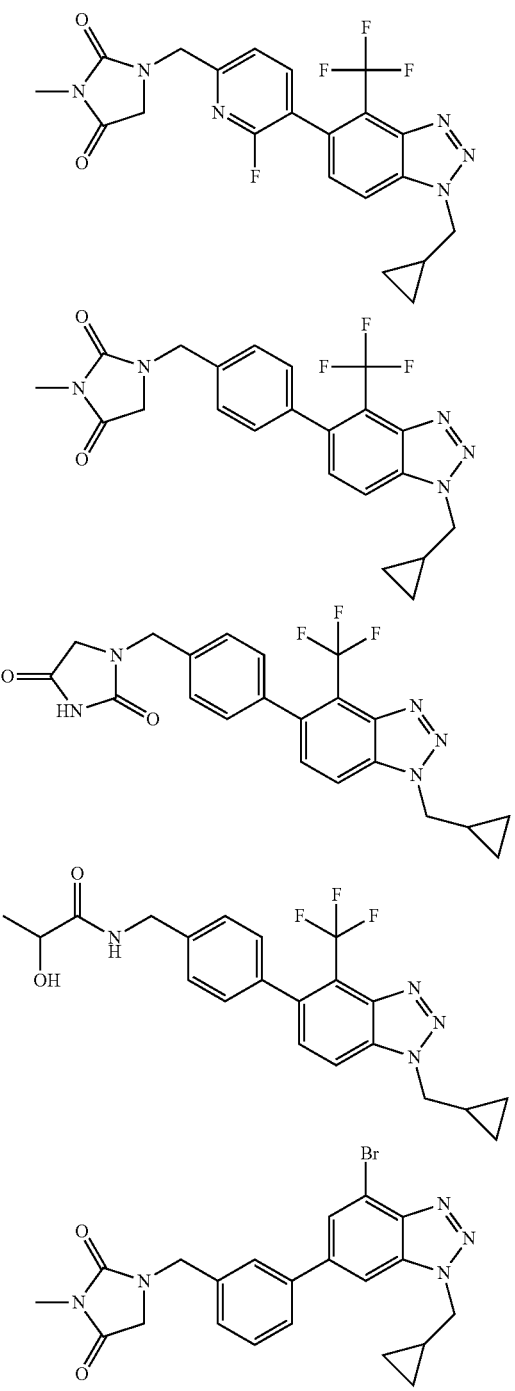

83
-continued
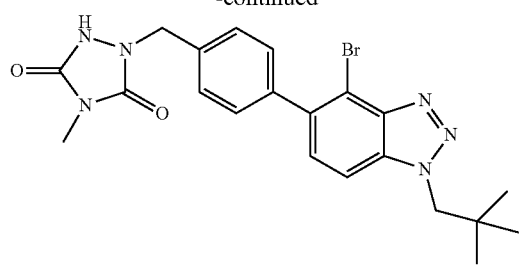
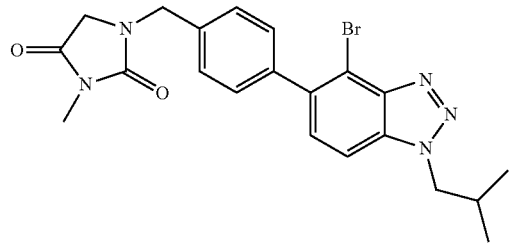
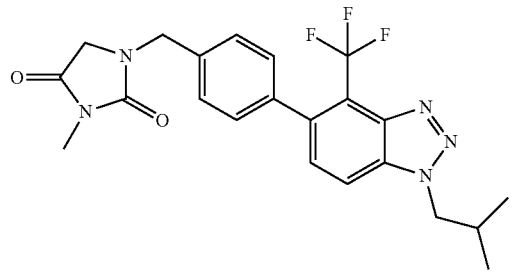
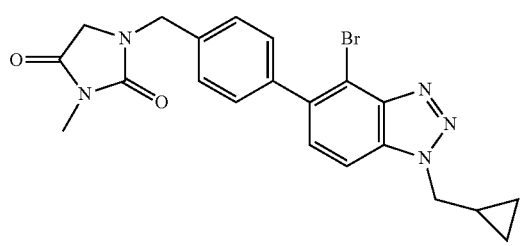
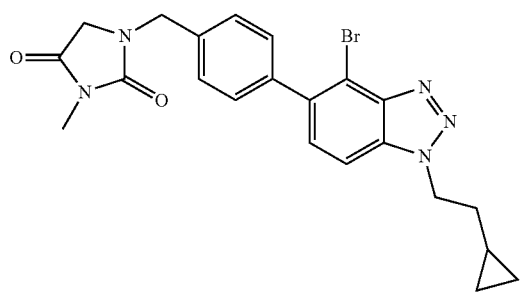
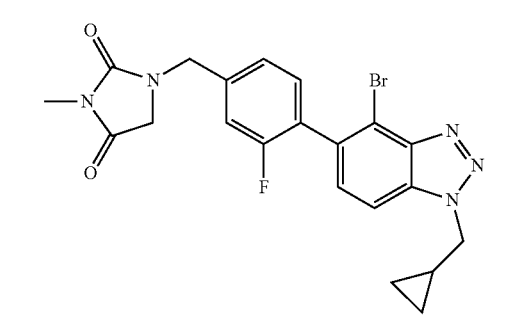
84
-continued
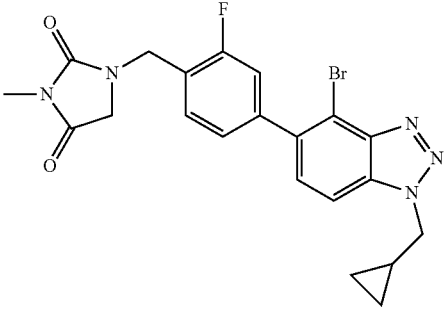
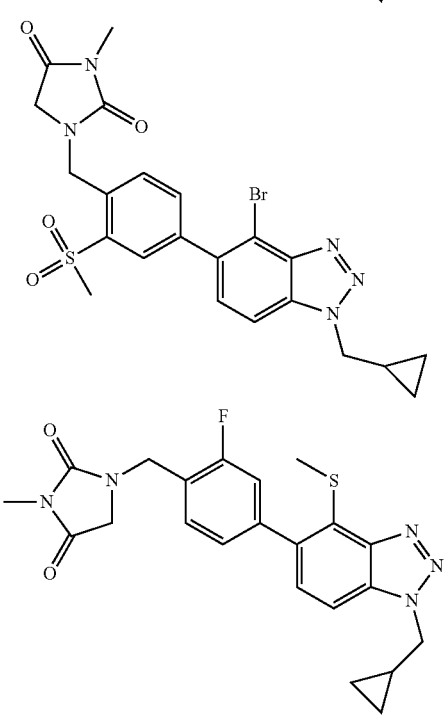
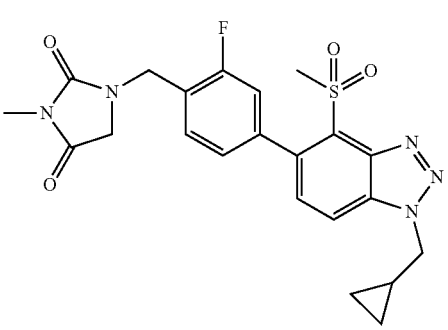
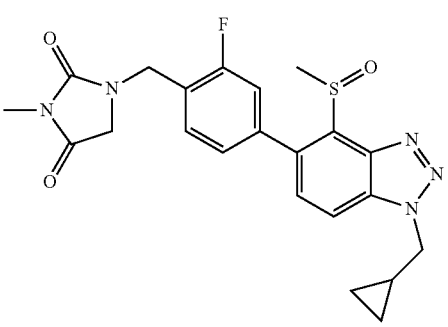

85
-continued
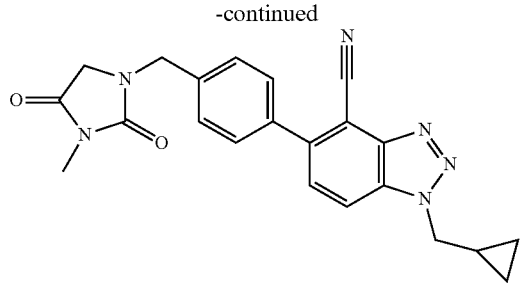
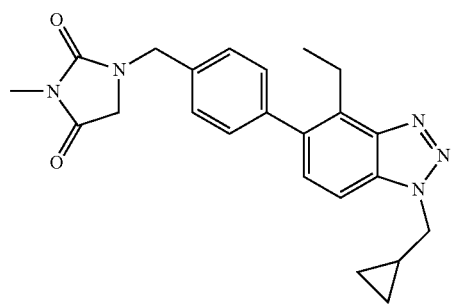
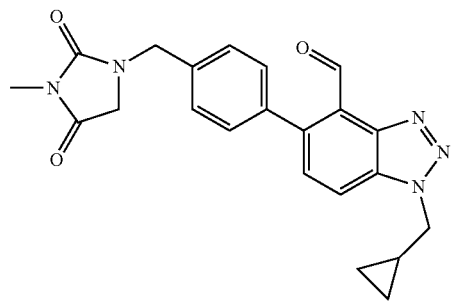
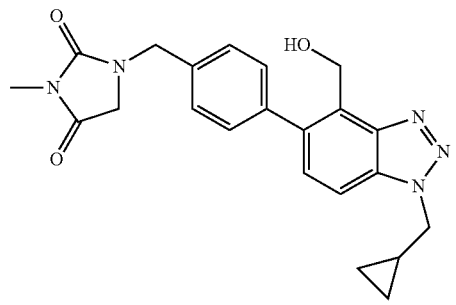
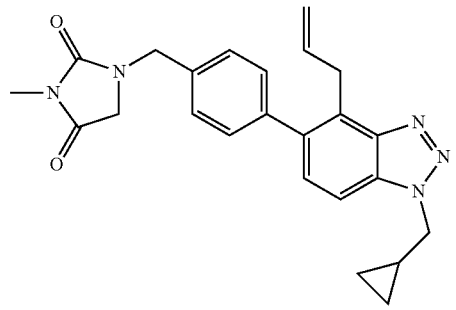
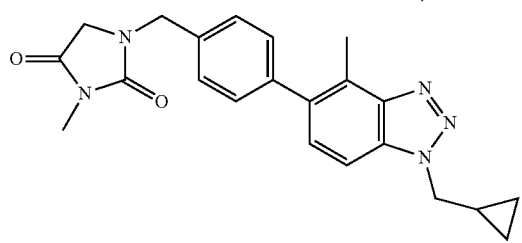
86
-continued
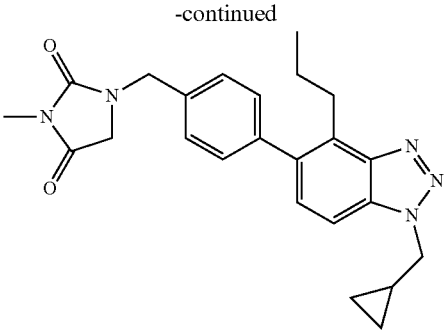
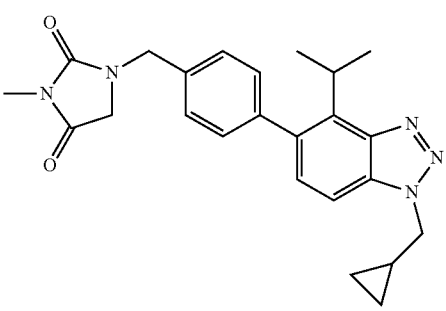
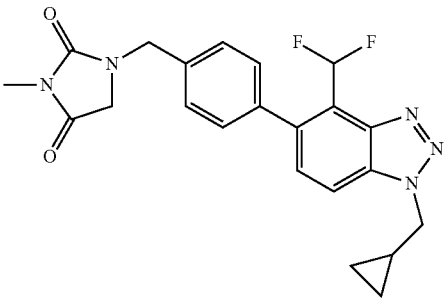
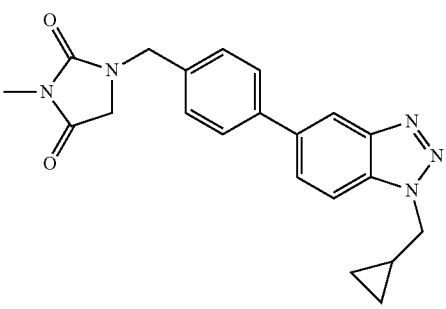
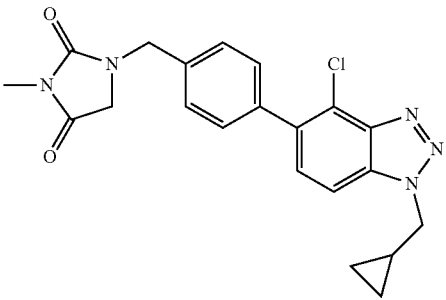

87
-continued
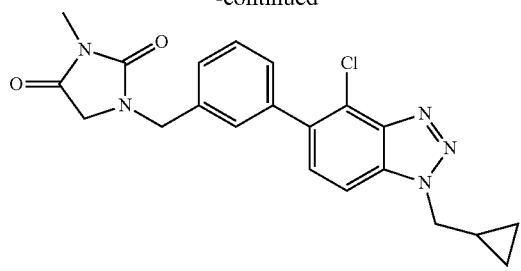
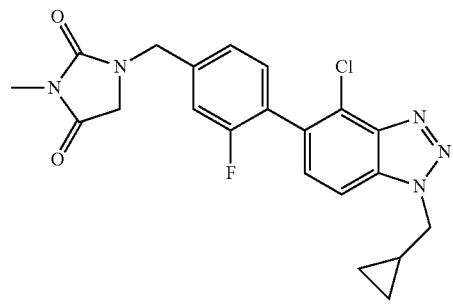
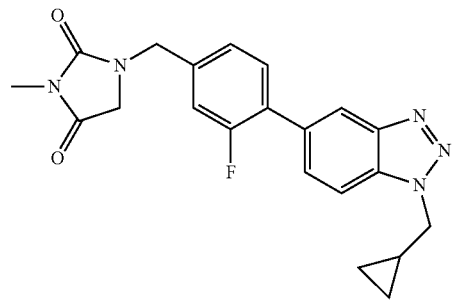
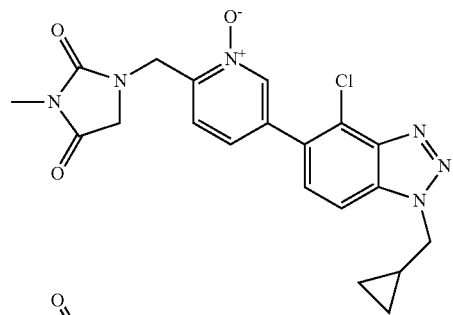
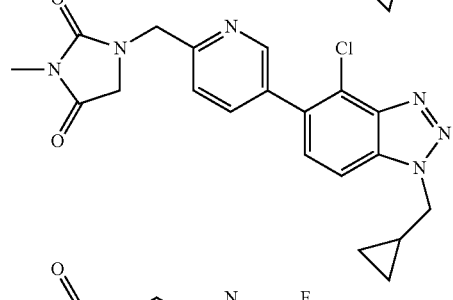
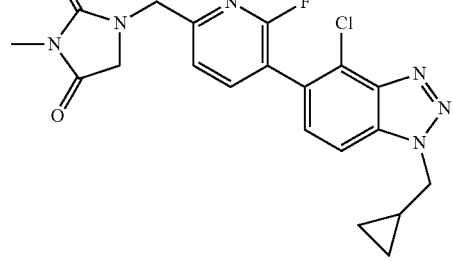
88
-continued
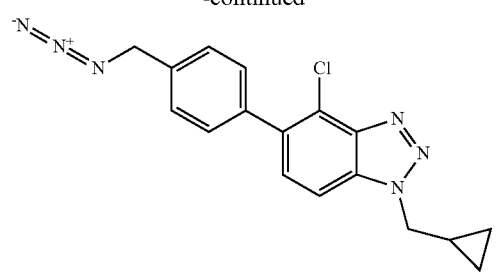
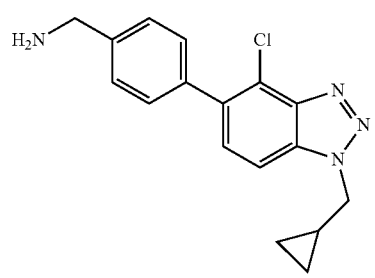
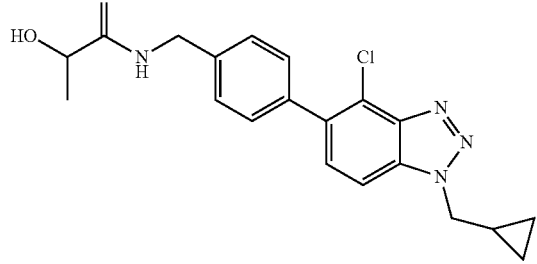
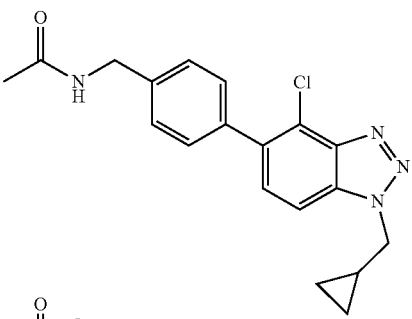
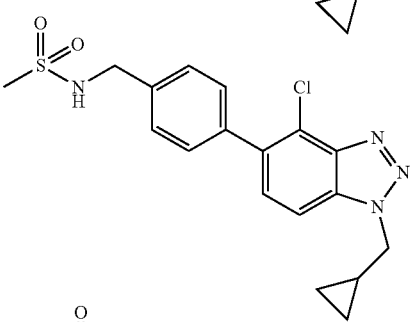
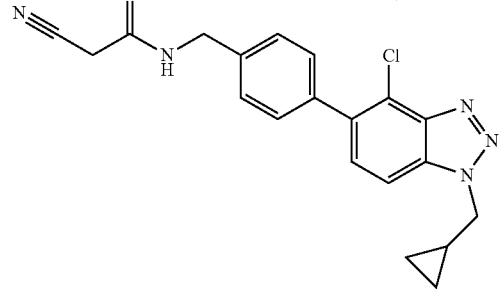

| 89 -continued | 90 -continued |
|---|---|
| 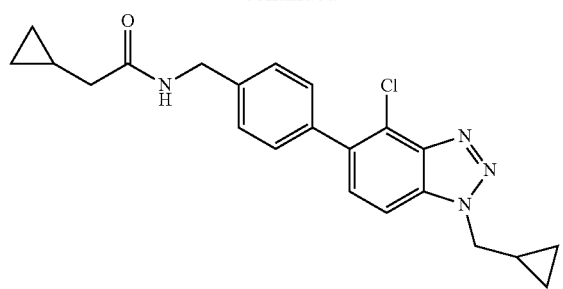 | 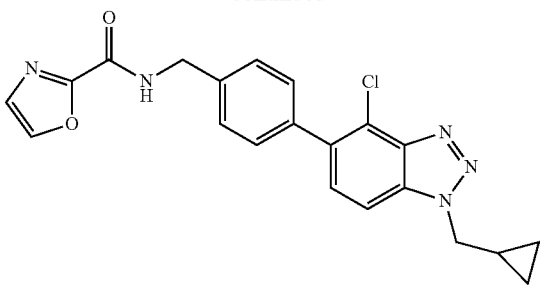 |
| 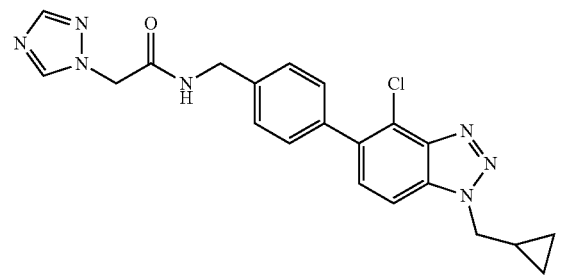 | 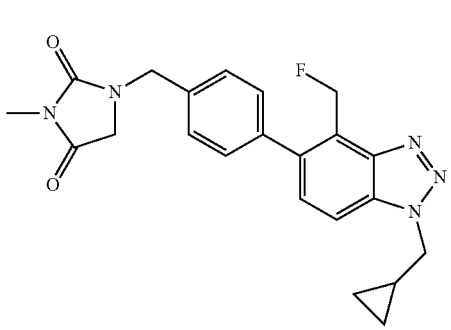 |
| 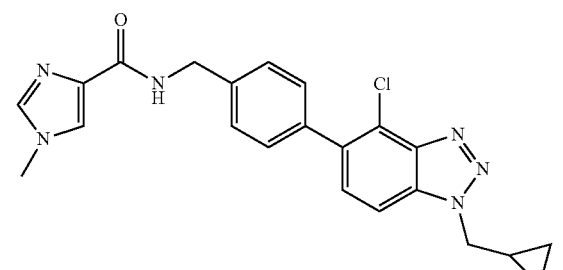 | 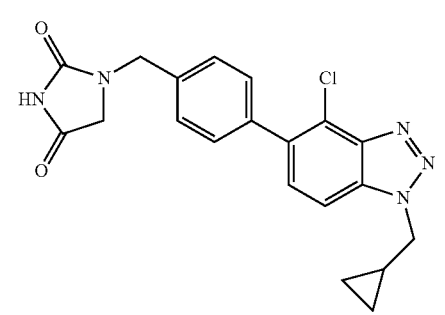 |
| 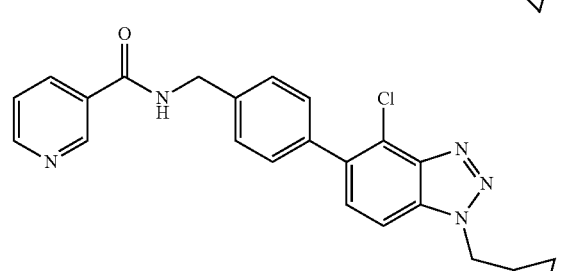 | 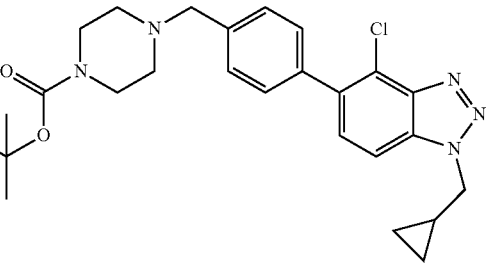 |
| 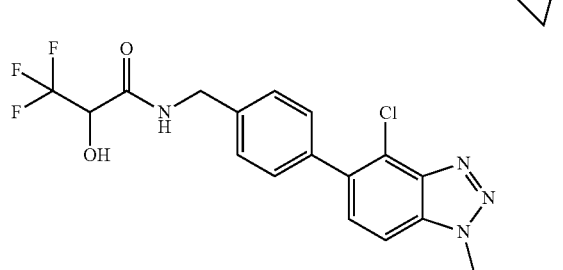 | 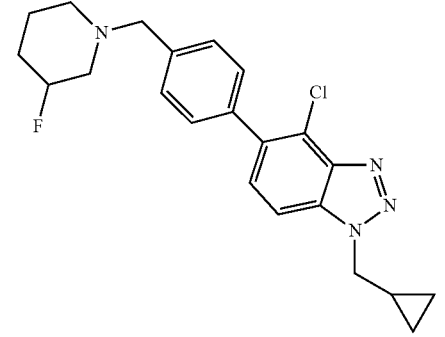 |
| 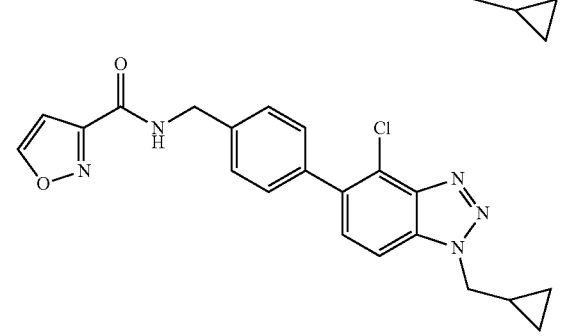 | |

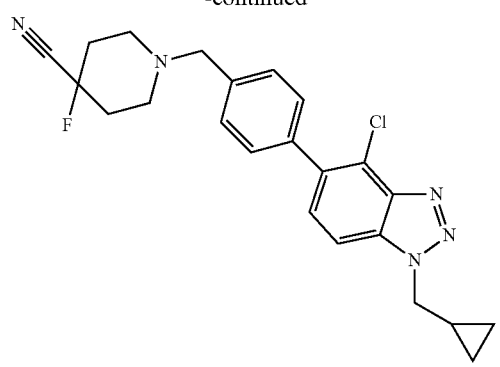
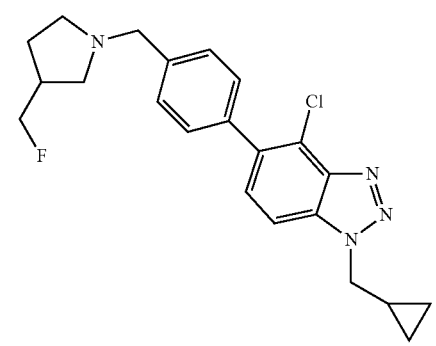
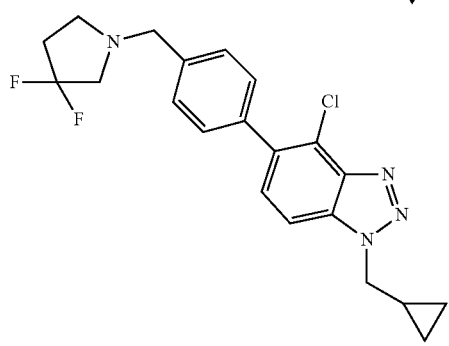
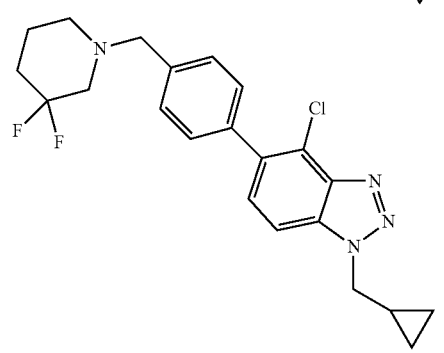
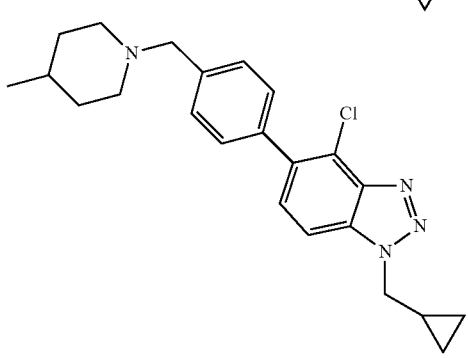
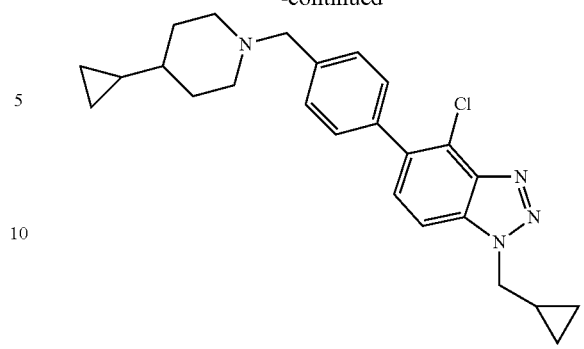
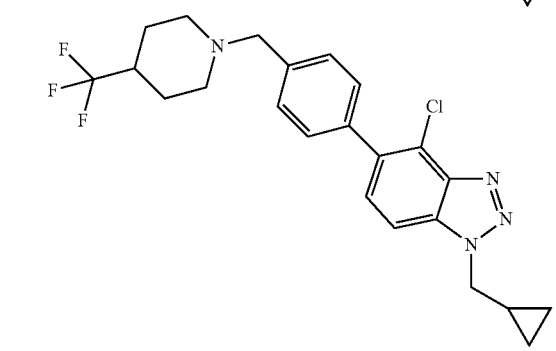
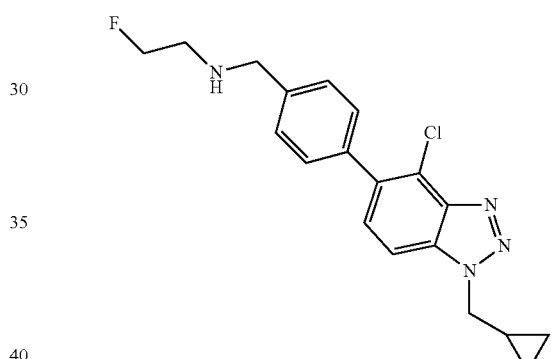
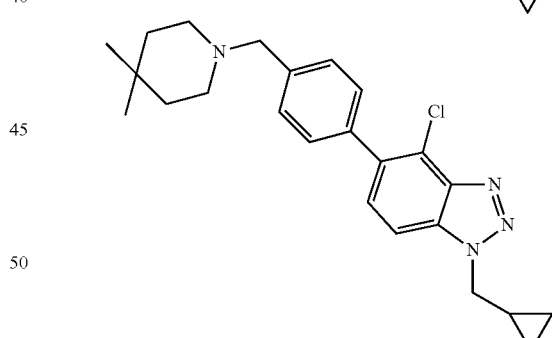
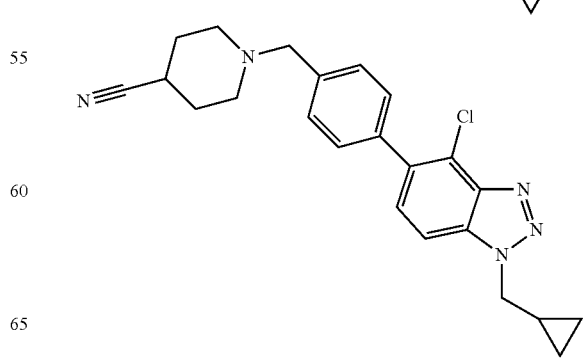

93
-continued
94
-continued
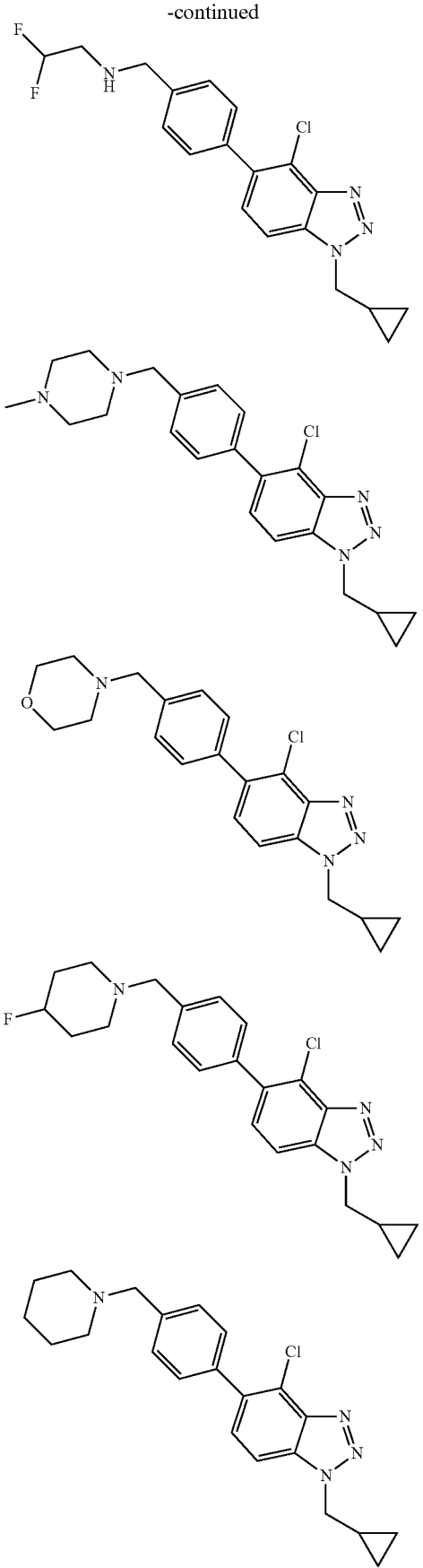
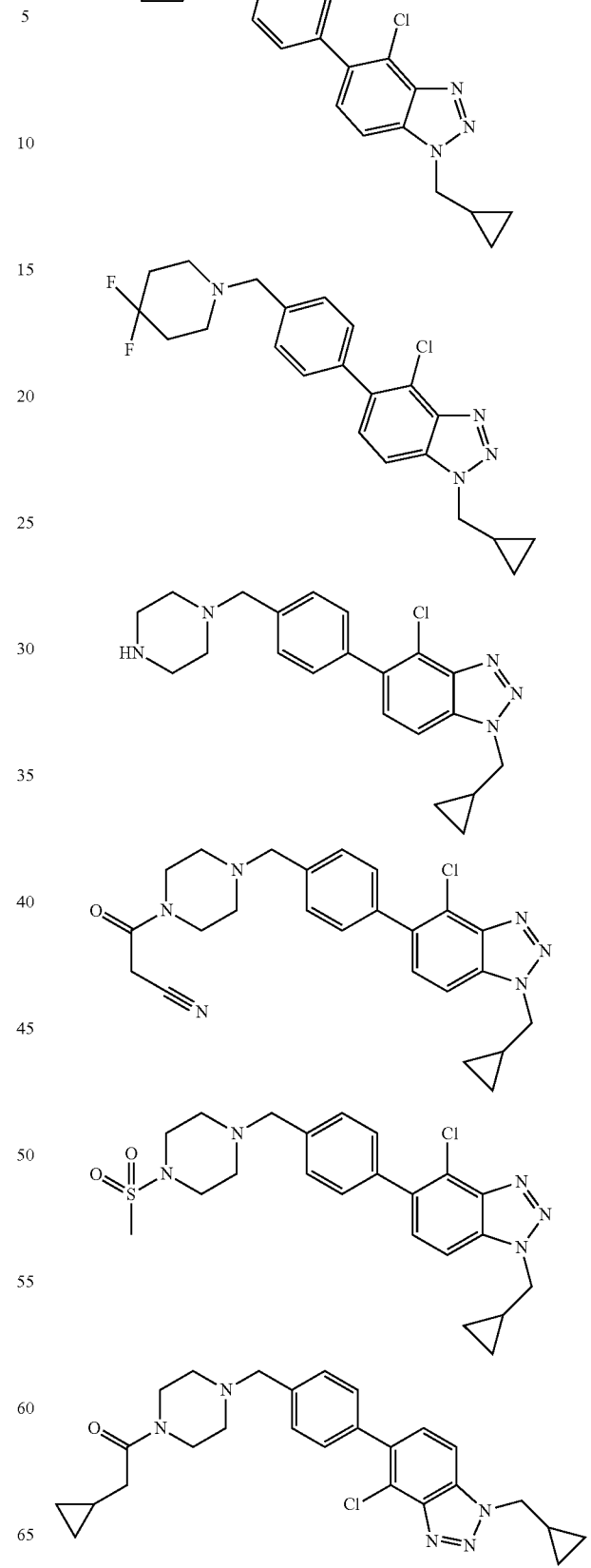

-continued
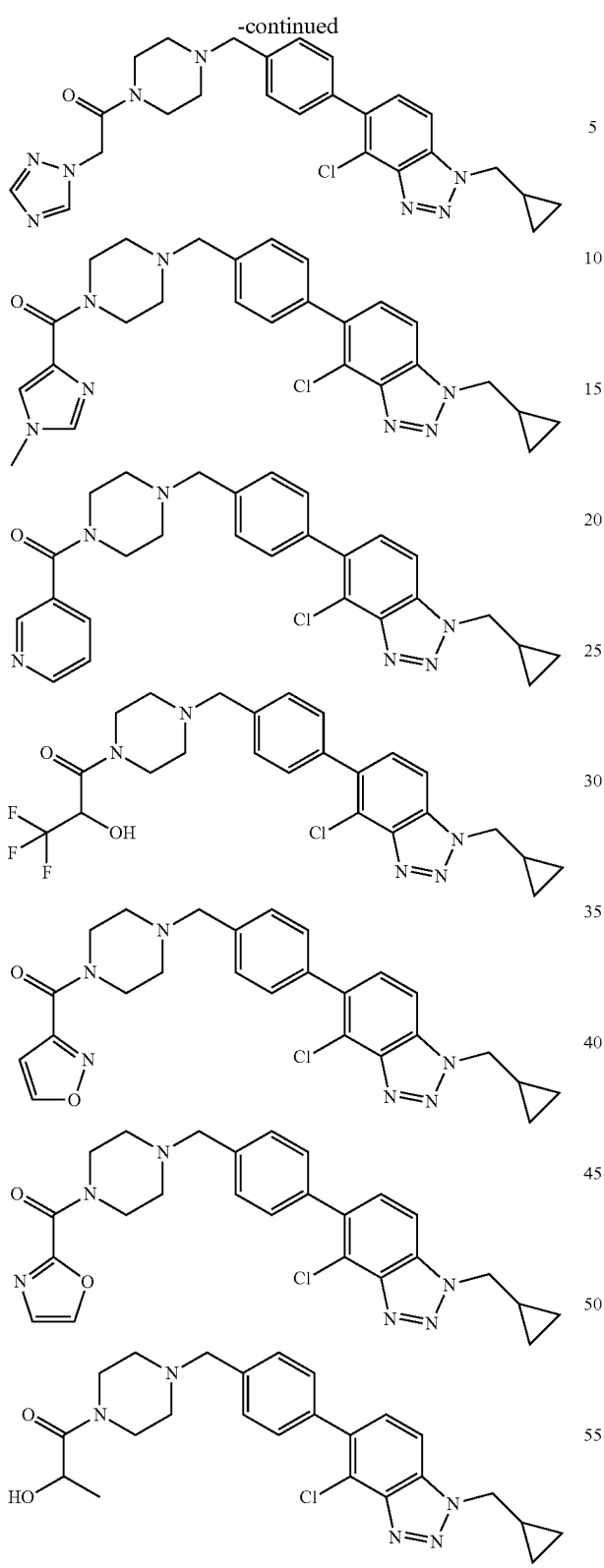
-continued
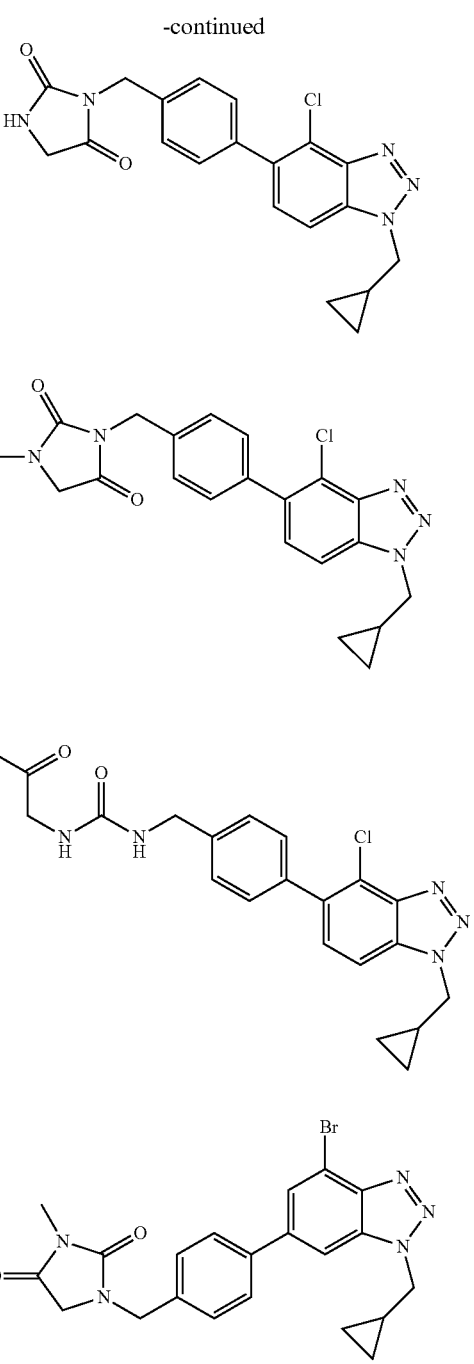
or a pharmaceutically acceptable salt of any of the foregoing compounds.
16. A pharmaceutical composition comprising a compound according to claim 1, or a pharmaceutically acceptable salt thereof, in combination with a pharmaceutically acceptable carrier.
* * * * *